US006852834B2

(12) United States Patent
Chilkoti

(10) Patent No.: US 6,852,834 B2
(45) Date of Patent: Feb. 8, 2005

(54) FUSION PEPTIDES ISOLATABLE BY PHASE TRANSITION

(76) Inventor: Ashutosh Chilkoti, 915 Englewood Ave., Durham, NC (US) 27701

(*) Notice: Subject to any disclaimer, the term of this patent is extended or adjusted under 35 U.S.C. 154(b) by 112 days.

(21) Appl. No.: 09/812,382

(22) Filed: Mar. 20, 2001

(65) Prior Publication Data

US 2001/0034050 A1 Oct. 25, 2001

Related U.S. Application Data

(60) Provisional application No. 60/190,659, filed on Mar. 20, 2000.

(51) Int. Cl.$^7$ .................. C07K 1/100; A23J 1/100; C12P 21/08; C12N 9/02; C12N 9/82

(52) U.S. Cl. .................. 530/350; 530/412; 530/387.3; 530/351; 530/303; 530/307; 530/306; 530/308; 530/311; 530/399; 530/302; 530/301; 435/189; 435/229; 435/227; 435/213; 435/226; 435/183

(58) Field of Search .................. 530/300, 412, 530/387.3, 357, 303, 307, 306, 308, 311, 399, 302, 301; 435/189, 229, 227, 213, 226, 183

(56) References Cited

U.S. PATENT DOCUMENTS

| | | | |
|---|---|---|---|
| 4,783,523 A | 11/1988 | Urry et al. | |
| 4,870,055 A | 9/1989 | Urry et al. | |
| 4,898,926 A | 2/1990 | Urry | |
| 5,028,419 A | 7/1991 | Pigiet | 424/71 |
| 5,235,041 A | 8/1993 | Cappello et al. | 530/353 |
| 5,243,038 A | 9/1993 | Ferrari et al. | 536/23.1 |
| 5,496,712 A | 3/1996 | Cappello et al. | 435/69.1 |
| 5,514,581 A | 5/1996 | Ferrari et al. | 435/252.3 |
| 5,527,610 A | 6/1996 | Urry | |
| 5,641,648 A | 6/1997 | Ferrari et al. | 435/69.1 |
| 5,646,016 A | 7/1997 | McCoy et al. | 435/69.7 |
| 5,770,697 A | 6/1998 | Ferrari et al. | 530/353 |
| 5,773,249 A | 6/1998 | Cappello et al. | 435/69.1 |
| 5,792,506 A | 8/1998 | Buchanan et al. | 426/656 |
| 5,830,713 A | 11/1998 | Ferrari et al. | 435/91.1 |
| 5,854,387 A | 12/1998 | Urry et al. | |
| 5,900,405 A | 5/1999 | Urry | |
| 5,919,657 A | 7/1999 | Hillman et al. | 435/69.1 |
| 5,952,034 A | 9/1999 | Buchanan et al. | 426/656 |
| 5,972,406 A | 10/1999 | Urry et al. | 426/549 |
| 5,985,261 A | 11/1999 | White et al. | 424/85.1 |
| 6,004,782 A | 12/1999 | Daniell et al. | 435/71.2 |
| 6,013,857 A | 1/2000 | Deboer et al. | 800/15 |
| 6,018,030 A | 1/2000 | Ferrari et al. | 530/353 |
| 6,140,072 A | 10/2000 | Ferrari et al. | 435/69.1 |
| 6,184,348 B1 | 2/2001 | Ferrari et al. | 530/350 |
| 6,328,996 B1 | 12/2001 | Urry | 424/499 |
| 6,355,776 B1 | 3/2002 | Ferrari et al. | 530/350 |

FOREIGN PATENT DOCUMENTS

WO    WO96/32406    10/1996

OTHER PUBLICATIONS

Urry, D.W., et al., Phase–structure Transitions of the Elastin Polypentapeptide–water system within the framework of composition–temperature studies, *Biopolymers*, 24:2345–2346, (1985).

Porath, J. et al., Immobilized metal ion affinity chromatography, *Prot. Expr. Purif.*, 3:262–282 (1992).

Homgren, A., Thioredoxin, *Annu. Rev. Biochem*, 54:237–271 (1985).

Smith, P.K., et al., Measurement of protein using bicinchonic acid, *Anal. Biochem*, 150:76–85 (1986).

Holmgren, A. et al., Enzymatic reduction–oxidation of protein disulfides by thioredoxin, *Methods Enzymol*, 107:295–300 (1984).

Meyer, D. and Chilkoti, Purification of Recombinant Proteins by Fusion with Thermally Responsive Polypeptides, *Nat. Biotechnol*, 17:1112–1115 (1999).

McPherson, D., et al., Production and purification of a recombinant elastomeric polypeptide, G–(VPGVG)$_{19}$–VPGV from *Eschericia coli, Biotechnol, Prog.*, 8:347–352 (1992).

Urry, D.W., Entropic Elastic Processes in Protein Mechanisms. I. Elastic Structure Due to an Inverse Temperature Transition and Elasticity Due to Internal Chain Dynamics, *Journal of Protein Chemistry*, vol. 7, No. 1, pp. 1–34 (1988).

Urry, D.W., Free Energy Transduction in Polypeptides and Proteins Based on Inverse Temperature Transitions, *Prog. Biophys. Molec. Biol.*, vol. 57, pp. 23–57, (1992).

Urry, D.W., Physical Chemistry of Biological Free Energy Transduction as Demonstrated by Elastic Protein–Based Polymers, *J. Phys. Chem. B*, vol. 101, No. 51, pp. 11007–11028, (1997).

McPherson, et al., Product Purification by Reversible Phase Transition Following *Escherichia coli* Expression of Genes Encoding up to 251 Repeats of the Elastomeric Pentapeptide GVGVP, *Protein Expression and Purification*, 7, pp. 51–57, (1996).

(List continued on next page.)

*Primary Examiner*—Rebecca E. Prouty
*Assistant Examiner*—Malgorzata A. Walicka
(74) *Attorney, Agent, or Firm*—Yongzhi Yang; Tristan Fuierer; Steven Hultquist

(57) ABSTRACT

Genetically-encodable, environmentally-responsive fusion proteins comprising ELP peptides. Such fusion proteins exhibit unique physico-chemical and functional properties that can be modulated as a function of solution environment. The invention also provides methods for purifying the FPs, which take advantage of these unique properties, including high-throughput purification methods that produce high yields (e.g., milligram levels) of purified proteins, thereby yielding sufficient purified product for multiple assays and analyses. The high throughput purification technique is simpler and less expensive than current commercial high throughput purification methods, since it requires only one transfer of purification intermediates to a new multiwell plate.

41 Claims, 20 Drawing Sheets

OTHER PUBLICATIONS

Hoffman, A.S., Applications of Thermally Reversible Polymers and Hydrogels in Therapeutics and Diagnostics, *Journal of Controlled Release*, 6, pp. 297–305, (1987).

Chen, J.P., et al., Polymer–protein conjugates, II. Affinity precipitation separation of human immunogammaglobulin by a poly(N–isopropylacrylamide)–protein A conjugate, *Biomaterials*, 11:631–634 (1990).

Chilkoti, A., et al., Site–Specific Conjugation of a Temperature–Sensitive Polymer to a Genetically–Engineered Protein, *Bioconjugate Chemistry*, vol. 5, pp. 504–507, (1994).

Nilsson, B., et al., Fusion proteins in biotechnology and structural biology, *Curr. Ipin. Struct. Biol.*, 2:569–575 (1992).

Uhlen, M. and Moks, Tomas, Gene Fusions for Purpose of Expression: An Introduction, *Methods of Enzymology*, vol. 185, pp. 129–143 (1990).

Maina, C.V., et al., An *Eschericia coli* vector to express and purify foreign proteins by fusion to and separation from maltose–binding protein, *Gene*, 74:365–373 (1988).

Smith, D.B., et al., Single–step purification of polypeptides expressed in *Escherichia coli* as fusions with glutathione S–transferase, *Gene*, 67:31–40 (1988).

Tsao, Kwe–Lan, et al., A versatile plasmid expression vector for the production of biotinylated proteins by site–specific, enzymatic modification in *Escherichia coli*, *Gene*, 169:59–64 (1996).

Smith, P.A., et al., A plasmid expression system for quantitative in vivo biotinylation of thioredoxin fusion proteins in *Escherichia coli*, Nucleic Acids Research, vol. 26, No. 6 (1998).

LaVallie, E.R., et al., A Thioredoxin Gene Fusion Expression System That Circumvents Inclusion Body Formation in the *E. coli* Cytoplasm, *Bio/Technology*, vol. 11, pp. 187–193 (1993).

Ong, E. et al., The cellulose–binding domains of cellulases: tools for biotechnology, *Trends. Biotechnol.*, 7:239–243 (1989).

Smith, Michele C. et al., Chelating Peptide–immobilized Metal Ion Affinity Chromatography, *The Journal of Biological Chemistry*, vol. 263, No. 15, pp. 7211–7215, (1988).

Kim, Jin–Soo et al., Ribonuclease S–peptide as a carrier in fusion proteins, *Protein Science*, 2:348–356, (1993).

Su, Xinzhuan, et al., production ffo Recombinant Porcine IumorNecrosis Factor Alpha in a Novel *E. coli* Expression System, *Biotechniques*, 13:756–765 (1992).

Nilsson, J. et al., Affinity Fusion Strategies for Detection, Purification, and Immobilization of Recombinant Proteins, *Protein Expression and Purification*, 11:1–16 (1997).

Hauck, M. L. et al., Local Hyperthermia Improves Uptake of a Chimeric Monoclonal Antibody in a Subcutaneous Xenograft Model, *Clin. Cancer Res.*, 3:63–70 (1997).

Cope, D.A. et al., Enhanced Delivery of a Monoclonal Antibody $F(ab^1)_2$ Fragment to Subcutaneous Human Glioma Xenografts Using Local Hyperthermia, *Cancer Res.*, 50:1803–1809, (1990).

Vertesy, L. et al., Tendamistat (HOE 467), a tight–binding α–amylase inhibitor from *Streptomyces tendae* 4158, *Eur. J. Biochem*, 141:505–512, (1984).

Urry, D.W., et al., Temperature of Polypeptide Inverse Temperature Transition Depends on Mean Residue Hydrophobicity, *J. Am. Chem. Soc.*, 113:4346–4348, (1991).

Kobatake, Eiry, et al., "Design and Gene Engineering Synthesis of an Extremely Thermostable Protein with Biological Activity," Biomacromolecules 2000, 1: 382–386.

Meyer, Dan E., et al., "Protein Purificaiton by Fusion with an Environmentally Responsive Elastin–Like Polypeptide: Effect of Polypeptide Length on the Purification of Thioredoxin," Biotechnol. Prog. 2001, 17 (4): 720–728.

Meyer, Dan E., et al. "Targeting a Genetically Engineered Elastin–like Polypeptide to Solid Tumors by Local Hypothermia," Cancer Res Feb. 15, 2000; 61(4): 1548–54.

Meyer, Dan E., et al. "Drug targeting using thermally responsive polymers and local hyperthermia," Journal of Controlled Release Jul. 6, 2001; 74: 213–24.

FIG.10

ELP GENE (10-mer BASE SEQUENCE)

```
    |EcoR I                      |PflM I
A ATT CAT ATG GGC CAC GGC GTG GGT GTT CCG GGT GTT CCG GGC GTG GGT GTT CCG GGC GGT GCA GGT GTT
         V   G   H   G   V   G   V   P   G   V   P   G   V   G   V   P   G   G   A   G   V

CCT GGT GTA GGT GTG CCG GGT GTT GGT GTG CCG GGT GTT GGT GTA CCA GGT GCC GGT GTT CCG GGT GCA GGC
 P   G   V   G   V   P   G   V   G   V   P   G   V   G   V   P   G   A   G   V   P   G   A   G
                                                |Bgl I              |HinD III

GTT CCG GGT GGC GGT GTG CCG GGC CTG AAA TGA TA
 V   P   G   G   G   V   P   G   L   K
```

FUSION PEPTIDES ISOLATABLE BY PHASE TRANSITION

This application claims benefit of 60/190,659 filed Mar. 20, 2000.

1. FIELD OF THE INVENTION

The invention provides a new generation of genetically-encodable, environmentally-responsive fusion proteins comprising elastin-like peptides (ELPs). The fusion proteins of the invention (referred to herein as "FPs") exhibit unique physico-chemical and functional properties that can be modulated as a function of solution environment. The invention also provides methods for purifying the FPs, including high-throughput purification techniques, which take advantage of these unique properties.

2. BACKGROUND OF THE INVENTION

ELPs, as explained more fully in the Detailed Description a the Invention hereof (Section 5) are oligomeric repeats of the pentapeptide Val-Pro-Gly-X-Gly (Sequence ID No. 1), here the guest residue X is any amino acid. ELPs undergo a reversible inverse temperature transition. They are highly soluble in water below the inverse transition temperature ($T_t$), but undergo a sharp (2–3° C. range) phase transition when the temperature is raised above their $T_t$, leading to desolvation and aggregation of the polypeptide.[1,2,3] In previous work, McPherson et al. have exploited the inverse transition to purify recombinant poly(GVGVP) polypeptide. Previous studies have also shown that protein conjugates of poly(N-isopropylacrylamide), a synthetic polymer that undergoes a similar thermally-reversible phase transition, also retain the transition behavior of the free polymer.[5,6,7]

Recombinant DNA techniques have facilitated the expression of proteins for diverse applications in medicine and biotechnology. However, the purification of recombinant proteins is often complicated and problematic. In the last decade, a number of protein expression systems have been developed to simplify protein purification.[8,9] Such systems often operate by expressing a recombinant protein fused with a carrier protein or peptide. A number of fusion protein systems using different carrier proteins are now commercially available, particularly for *E. coli* expression. Examples include maltose binding protein,[10] glutathione S-transferase,[11] biotin carboxyl carrier protein,[12,13] thioredoxin,[13,14] and cellulose binding domain.[15] Similarly, vectors that allow fusion of the target protein to short peptide tags such as oligohistidine,[16] S-peptide,[17] and the FLAG peptide[18] are also available.

Fusion protein expression simplifies the separation of recombinant protein from cell extracts by one-step purification by affinity chromatography using an immobilized, moderate-affinity ligand specific to the carrier protein.[19] Although useful for laboratory scale purification, the scale-up of affinity chromatography can represent a major cost of the final protein product at the preparative scale.

Additionally, chromatography represents a major bottleneck in high throughput purification of proteins. The full implications of the human genome project will not be realized until all the proteins encoded in the genome can be expressed and studied in detail. Current chromatographic technologies cannot be easily multiplexed to efficiently purify the wide diversity of proteins encoded in the human genome. These limitations of current bioseparation techniques, therefore, provide a compelling rationale for the development of nonchromatographic methods for the purification of soluble, recombinant proteins. Likewise, non-chromatographic purification methods would also be attractive as technically simple, reliable, and broadly applicable methods for bench top, milligram-scale purification of single proteins.

More economical and technically simple methods for purification of soluble proteins, which do not involve scale-up of chromatographic procedures, are therefore desirable.

The inventor has surprisingly discovered that incorporation of ELPs in fusion proteins, enables non-chromatographic, thermally-stimulated phase separation of recombinant proteins. These FPs undergo a phase transition similar to that of free ELPs. This surprising discovery is useful in the purification of fusion proteins incorporating one or more ELP tags.

Elastin-like polypeptides (ELPs) are thermally responsive polypeptides that undergo reversible aggregation above a critical temperature. An ELP is a polypeptide with the repeating pentapeptide sequence Val-Pro-Gly-Xaa-Gly (where the guest residue Xaa can be any amino acid, except Pro, in any fraction). Below the inverse transition temperature ($T_t$), ELPs are structurally disordered and soluble in aqueous solutions, but when the temperature is raised above their $T_t$, they undergo a sharp (2–3° C. range) disorder-to-order transition, leading to desolvation and aggregation of the polypeptide. These ELP aggregates can have sufficient mass that they can be removed from solution by centrifugation, but because the inverse transition is reversible, they can be completely resolubilized in buffer when the temperature is returned below the $T_t$ of the polypeptide.

By fusing a thermally responsive ELP to a target protein of interest, environmentally sensitive solubility can be imparted to the target protein. In the practice of the present invention, target proteins are expressed as soluble fusion proteins with N- or C-terminal ELP sequences in organisms such as *E. coli*, wherein the fusion proteins exhibit a soluble-insoluble phase transition. This inverse phase transition is exploited in the process of the invention to purify the fusion proteins from other soluble proteins produced by the organism, using a new nonchromatographic separation method for recombinant proteins, which the present inventor has termed "inverse transition cycling" (ITC).

The fundamental principle of ITC is remarkably simple. It involves rendering the ELP fusion protein insoluble in aqueous solution by triggering its inverse transition. This can be accomplished either by increasing the temperature above the $T_t$, or alternatively by depressing the $T_t$ below the solution temperature by the addition of NaCl to the solution. This results in aggregation of the ELP fusion protein, allowing it to be collected by centrifugation. The aggregated fusion protein can then be resolubilized in fresh buffer at a temperature below the $T_t$, thereby reversing the inverse transition, to yield soluble, functionally active, and purified fusion protein.

Free target protein then can be obtained, for example, by protease digestion at an engineered recognition site, located between the target protein and the ELP tag, followed by a final round of ITC to remove the cleaved ELP.

ITC has major advantages over other methods currently used for purification of recombinant proteins. It is technically simple, inexpensive, easily scaled up, and gentle, triggered by only modest alterations in temperature and/or ionic strength. The ITC technology is useful in the modulation of the physico-chemical properties of recombinant proteins and provides diverse applications in bioseparation, immunoassays, biocatalysis, and drug delivery.

The ITC methods of the invention exhibit significant advantages over currently used affinity purification methods in purifying recombinant fusion proteins. First, by circumventing chromatography, the expense associated with chromatographic resins and equipment is eliminated. Second, the separation and recovery conditions are gentle, requiring only a modest change in temperature or ionic strength. Third, the method is fast and technically simple, with only a few short centrifugation or filtration steps followed by resolubilization of the purified protein in a low ionic strength buffer. Finally, the equipment required, a temperature-controlled water bath and a centrifuge capable of operating at ambient temperature, are widely available. Additionally, ITC purification is independent of a specific expression vector or host and is exceptionally advantageous for use with eukaryotic expression systems, which readily over-express heterologous proteins in a soluble state.[20]

The ITC methodology of the invention also addresses a compelling need in the art for high-throughput purification techniques. The ITC purification technique of the invention is scalable in character, and can be appropriately scaled and multiplexed for concurrent, parallel laboratory purifications from numerous cell cultures.

Simultaneous purification of proteins from multiple cultures using the ITC methodology of the invention enables expedited structure-function studies of proteins as well as screening of proteins in pharmaceutical studies.

3. SUMMARY OF THE INVENTION

The invention generally provides a fusion protein (FP) exhibiting a phase transition, the fusion protein comprising: (a) one or more biological molecules; (b) one or more proteins exhibiting a phase transition joined to the biologically active molecule; and (c) optionally, a spacer sequence separating any of the protein(s) of (b) from any of the biological molecule(s) of (a).

The inventor has surprisingly discovered that such FPs retain the inverse transition behavior of the ELP carrier. The FPs thus provide a new generation of genetically-encodable, environmentally-responsive proteins whose physicochemical and functional properties can be modulated as a function of the solution environment. The inverse transition behavior of the FPs enables a one-step phase separation method for separating FPs from other soluble proteins.

The biological molecule component of the FP is preferably selected from the group consisting of proteins, lipids, and carbohydrates. More preferably, the biological molecule component comprises a protein, most preferably a biologically active protein, e.g., a therapeutic peptide or an enzyme useful in industrial biocatalysis.

The biological molecule component may also comprise an antibody or antibody fragment having affinity for a protein of interest. Upon binding to the protein of interest, the fusion protein preferably retains some or all of its phase transition character, so that the protein of interest may be isolated by inverse phase transition.

The phase transition of the FP is preferably mediated by one or more means selected from the group comprising: changing temperature; changing pH; addition of organic solutes and/or solvents; side-chain ionization or chemical modification; and changing pressure. The preferred means for mediating the phase transition is raising temperature.

The FPs of the invention comprise one or more proteins exhibiting a phase transition. These proteins preferably exhibit a β-turn structure, though such a structure is not strictly necessary. In a preferred mode, these proteins comprise oligomeric repeats of the pentapeptide Val-Pro-Gly-X-Gly, or VPGXG, wherein X is any natural or non-natural amino acid residue, and wherein X optionally varies among oligomeric repeats. Any two or more of the oligomeric repeats may be separated by one or more amino acid residues that do not eliminate the phase transition characteristic of the fusion protein. Preferably the ratio of Val-Pro-Gly-X-Gly oligomeric repeats to other amino acid residues of the ELP is greater than about 75%, more preferably the ratio is greater than about 85%, still more preferably the ratio is greater than about 95%.

The FPs optionally comprise spacer sequence(s) separating the one or more biological molecules from the one or more proteins exhibiting a phase transition. The spacer sequence, when present, preferably comprises a proteolytic cleavage site.

The FPs may be synthetically, e.g., recombinantly, produced.

The FPs of the invention may also comprise a signal peptide, which is preferably cleavable from the fusion protein by enzymatic cleavage. The signal peptide preferably directs secretion of the fusion protein from the cell, so that the FP may readily be isolated from the medium of an active culture of recombinant cells genetically modified to produce the FP.

In a preferred aspect, the invention provides a fusion protein exhibiting a phase transition, the fusion protein comprising: (a) one or more protein(s) of interest; (b) one or more protein(s) exhibiting a phase transition joined at a C- and/or N-terminus of a protein of (a); and (c) optionally, a spacer sequence separating the any of the protein(s) of (a) and/or (b).

In another preferred aspect, the invention provides a fusion protein exhibiting a phase transition, said fusion protein comprising: (a) one or more proteins of interest; (b) one or more β-turn protein(s) joined at a C- and/or N-terminus of any of the proteins of (a); and (c) optionally, a spacer sequence separating any of the protein(s) (a) and/or (b).

In yet another preferred aspect, the invention provides a fusion protein exhibiting a phase transition, the fusion protein comprising: (a) a protein of interest; (b) a protein exhibiting a phase transition joined at a C- and/or N-terminus of the protein of interest; and (c) optionally, a spacer sequence separating the protein or peptide of (a) from the protein of (c).

In another preferred aspect, the invention provides a fusion protein exhibiting a phase transition, said fusion protein comprising: (a) a protein of interest; (b) a protein exhibiting a β-turn joined at a C- and/or N-terminus of the protein of (a); and (c) optionally, a spacer sequence separating the protein of (a) from the protein of (c).

In a related aspect, the invention provides a polynucleotide comprising a nucleotide sequence encoding a fusion protein exhibiting a phase transition, said fusion protein comprising: (a) one or more proteins of interest; (b) one or more β-turn proteins exhibiting a phase transition joined at a C- and/or N-terminus of (a); and (c) optionally, a spacer sequence separating any of the protein(s) of (a) and/or (b). The polynucleotide may be provided as a component of an expression vector. The invention also provides a cell (prokaryotic or eukaryotic) transformed by such expression vector to express the fusion protein.

In a related aspect, the invention provides a method of producing one or more fusion proteins comprising: (a) transforming a host cell with the expression vector; and (b)

causing the host cell to express the fusion protein. In a preferred aspect, the fusion protein comprises a signal sequence directing secretion of the fusion protein from the cell so that the fusion protein may be isolated and/or partially purified from the culture medium.

The invention also provides a method for isolating and/or partially purifying one or more fusion proteins comprising: (a) expressing the fusion protein(s) by host cells as described in the preceding paragraph; (b) disrupting the cells to release the fusion proteins; and (c) isolating and/or partially purifying the proteins by a method comprising raising temperature.

In a preferred mode, the invention provides a method for isolating and/or partially purifying one or more fusion proteins from a culture comprising cells expressing such fusion proteins, the method comprising: (a) expressing the fusion proteins; (b) isolating the proteins by a method which comprises raising temperature.

The invention further provides a method of optimizing size of an ELP expression tag incorporated in a polynucleotide comprising a nucleotide sequence encoding a fusion protein exhibiting a phase transition, wherein the fusion protein comprises a protein of interest. Such method comprises the steps of (i) forming a multiplicity of polynucleotides comprising a nucleotide sequence encoding a fusion protein exhibiting a phase transition, wherein each of such multiplicity of polynucleotides includes a different-sized ELP expression tag, (ii) expressing corresponding fusion proteins from such multiplicity of polynucleotides, (iii) determining a yield of the desired protein for each of the corresponding fusion proteins, (iv) determining size of particulates for each of the corresponding fusion proteins in solution as temperature is raised above $T_t$, and (v) selecting an optimized size ELP expression tag according to predetermined selection criteria, e.g., for maximum recoverable protein of interest from among said multiplicity of polynucleotides, or for achieving a desired balance between yield and ease of isolation ability for each of the proteins of interest produced from the respective polynucleotides.

The ITC purification technique of the invention can be scaled down and multiplexed for concurrent, parallel laboratory scale purification from numerous cell cultures, to achieve simultaneous purification of proteins from multiple cultures. Such high-throughput purification application of the invention can be utilized, for example, to expedite both structure-function studies of proteins and the screening of proteins in pharmaceutical studies.

The invention provides in a further aspect a method of purification of fusion proteins to yield a protein of interest, by steps including forming a polynucleotide comprising a nucleotide sequence encoding a fusion protein exhibiting a phase transition, expressing the fusion protein in culture, and subjecting a fusion protein-containing material from the culture to processing involving centrifugation and inverse transition cycling to recover said protein of interest. In such methodology, the fusion protein-containing material from the culture may be the culture itself, or a subsequent processing fraction derived from the culture such as a lysed cellular suspension, cell pellets, supernatants, etc. The respective steps may be carried out on one or more microplates, as part of a high throughput purification arrangement for practicing the ITC method of the invention.

3.1 Definitions

The word "transform" is broadly used herein to refer to introduction of an exogenous polynucleotide sequence into a prokaryotic or eukaryotic cell by any means known in the art (including, for example, direct transmission of a polynucleotide sequence from a cell or virus particle as well as transmission by infective virus particles), resulting in a permanent or temporary alteration of genotype in an immortal or non-immortal cell line.

The term "protein" is used herein in a generic sense to include polypeptides of any length. The term "peptide" is used herein to refer to shorter polypeptides having less than 100 amino acid residues.

The term "functional equivalent" is used herein to refer to a protein that is an active analog, derivative, fragment, truncation isoform or the like of a native protein. A polypeptide is active when it retains some or all of the biological activity of the corresponding native polypeptide.

As used herein, "pharmaceutically acceptable" component (such as a salt, carrier, excipient or diluent) of a formulation according to the present invention is a component which (1)is compatible with the other ingredients of the formulation in that it can be combined with the FPs of the present invention without eliminating the biological activity of the FPs; and (2) is suitable for use with animals (including humans) without undue adverse side effects (such as toxicity, irritation, and allergic response). Side effects are "undue" when their risk outweighs the benefit provided by the pharmaceutical composition. Examples of pharmaceutically acceptable components include, without limitation, any of the standard pharmaceutical carriers such as phosphate buffered saline solutions, water, emulsions such as oil/water emulsions, microemulsions and various types of wetting agents.

As used herein, the term "native" used in reference to a protein indicates that the protein has the amino acid sequence of the corresponding protein as found in nature.

4. BRIEF DESCRIPTION OF THE DRAWINGS

Figure 4:
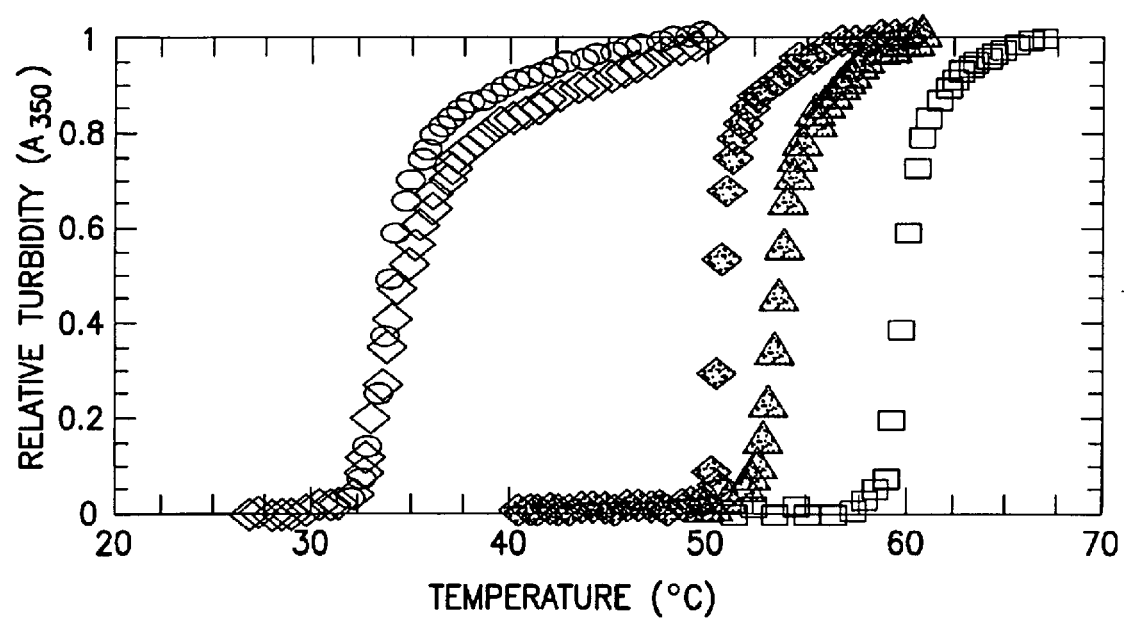

FIG. 4 is a plot showing the inverse transition characterization of free ELP (thrombin-cleaved and purified from thioredoxin-ELP) (♦); thioredoxin-ELP (▲); thioredoxin-ELP-tendamistat (○); ELP-tendamistat (cleaved and purified from thioredoxin-ELP-tendamistat) (◇); and thioredoxin-ELP (cleaved and purified from thioredoxin-ELP-tendamistat) (□). All fusions contained the same 90 pentapeptide ELP sequence. Profiles were obtained with protein concentrations of 25 $\mu$M in PBS using a 1.5° C. min$^{-1}$ heating rate.

Figure 5:
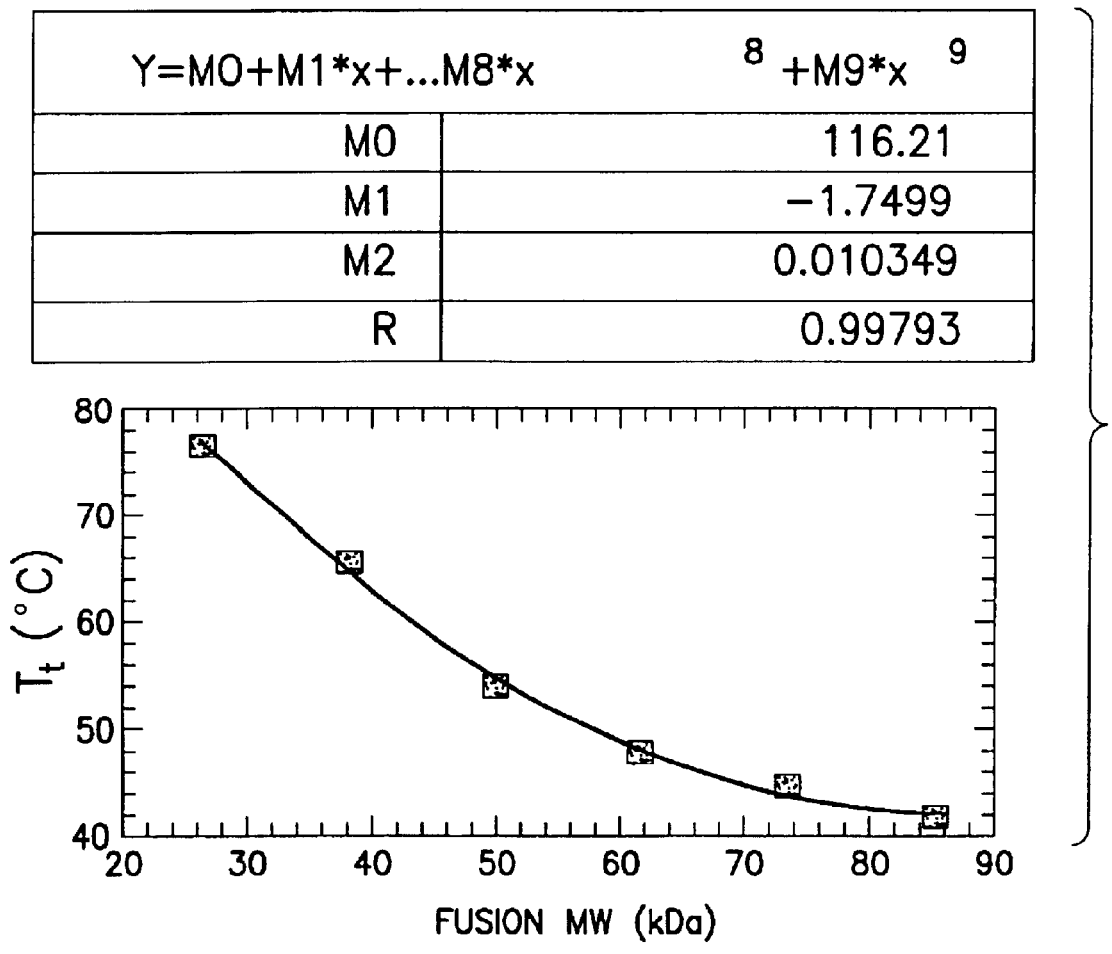

FIG. 5 is a plot showing transition temperature ($T_t$), defined as 50% maximal turbidity, as a function of molecular weight (MW) in kilodaltons (kDa) for thioredoxin-FPs.

Figure 6:
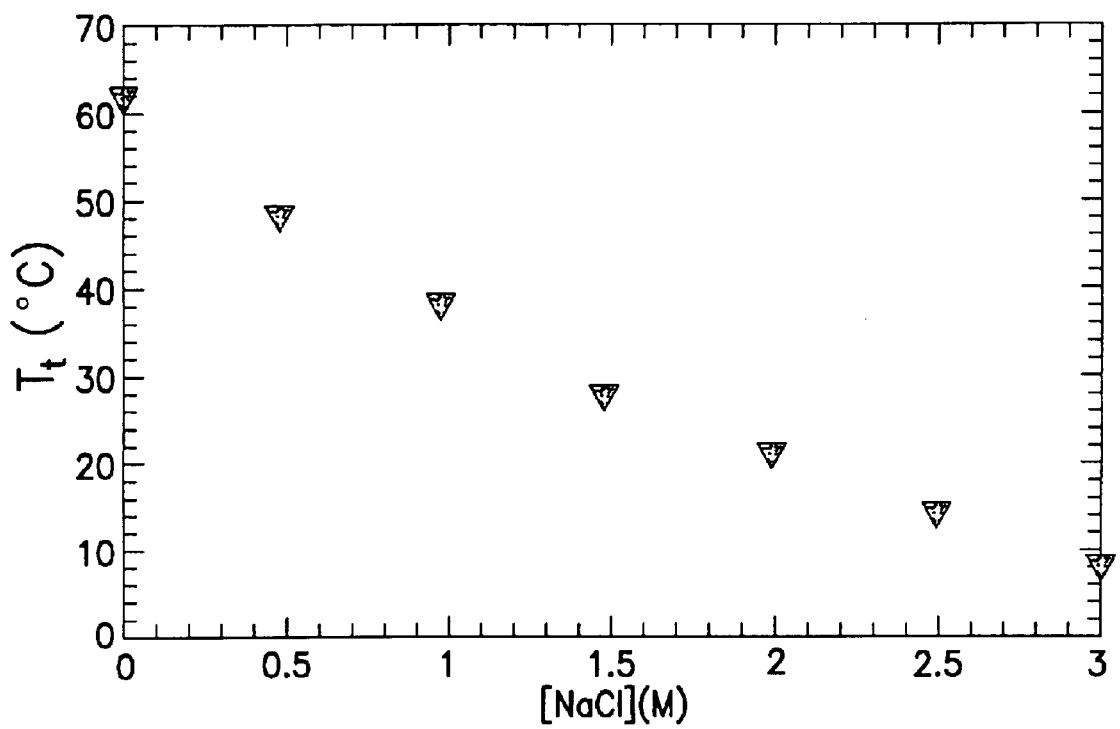

FIG. 6 is a plot of transition temperature as a function of NaCl molar concentration for the thioredoxin/60-mer FP (25 $\mu$M) in 50 mM phosphate buffer, pH 8.0.

Figure 7:
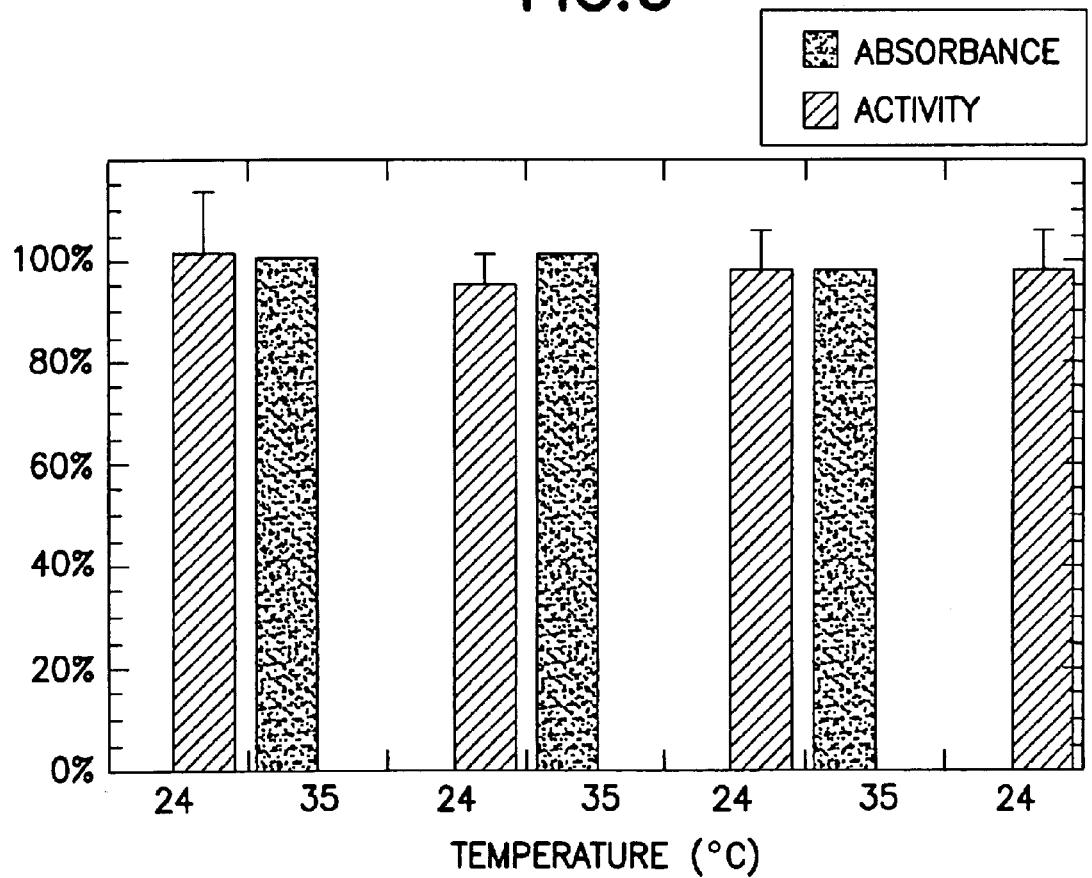

FIG. 7 is a graph of thioredoxin activity through 3 rounds of inverse transition cycling for the thioredoxin/60-mer fusion protein, wherein an increase in temperature resulted in aggregation of the fusion protein (monitored spectrophotometrically), reduction of temperature below $T_t$ caused the protein to disaggregate and the solution to clear, and thioredoxin activity, assayed after each cycle, was unaffected by the inverse transition cycling.

Figure 8:
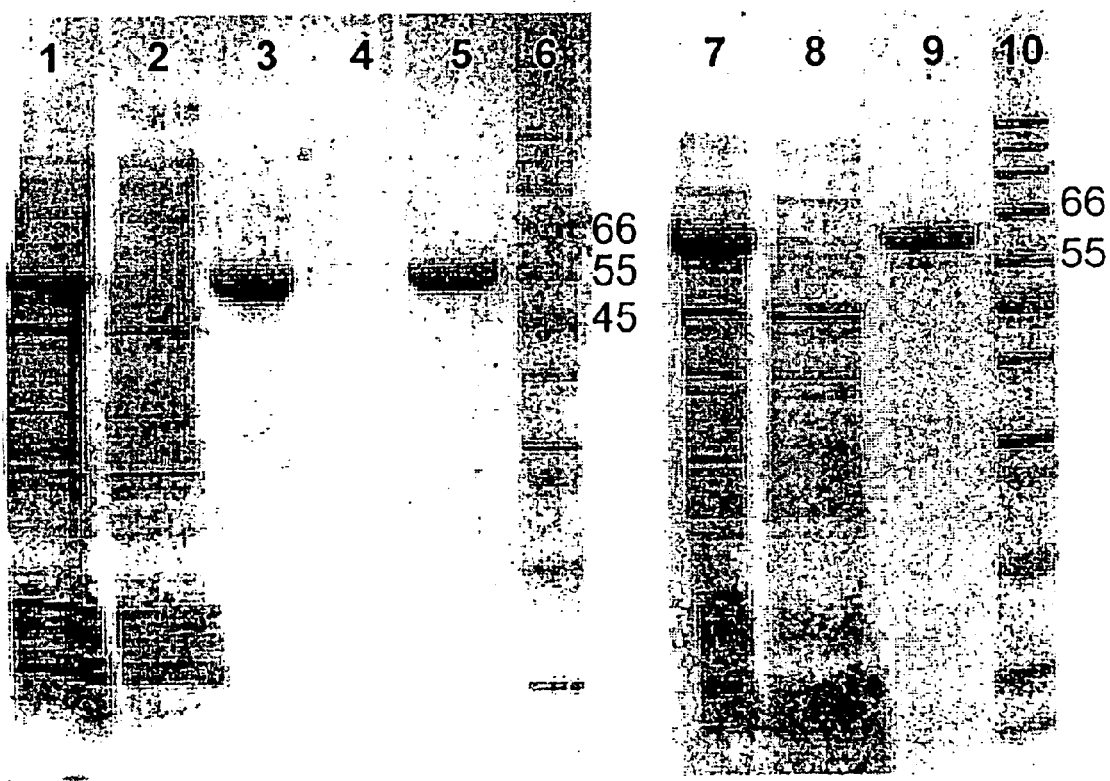

FIG. 8 is an SDS-PAGE characterization of inverse transition purification, showing each stage of purification for the thioredoxin/90-mer ELP fusion (49.9 kDa, lanes 1 through 5) and the thioredoxin/90-mer ELP/tendamistat (57.4 kDa, lanes 7 through 9): lanes 1 & 7, soluble lysate; lanes 2 & 8, discarded supernatant containing contaminating E. coli proteins; lanes 3 & 9: resolubilized pellet fraction containing purified fusion protein; lane 4, second round supernatant; lane 5: second round pellet; lanes 6 and 10: molecular weight markers (kDa).

Figure 9:
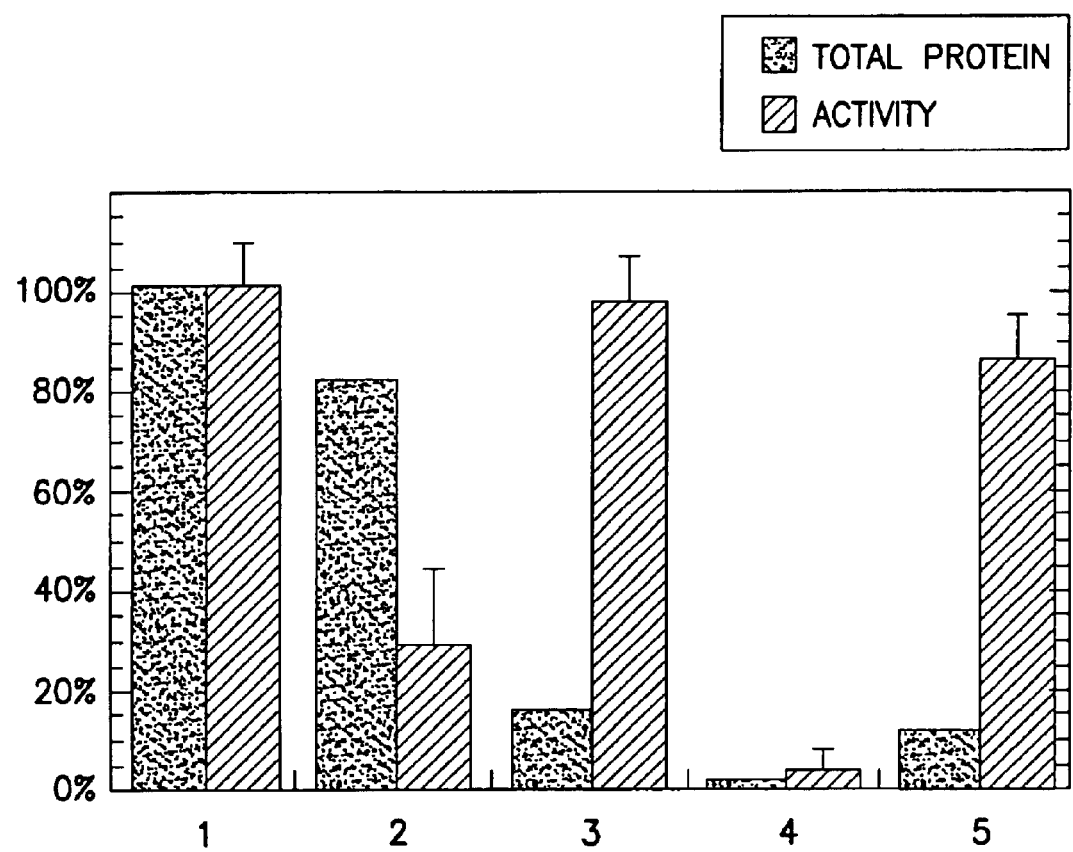

FIG. 9 is a graph of total protein and thioredoxin activity for each stage of purification of the thioredoxin/90-mer ELP, wherein values were normalized to those determined for the soluble lysate.

FIG. 10 shows DNA and corresponding amino acid sequences for the 10 pentapeptide ELP gene.

Figure 11:
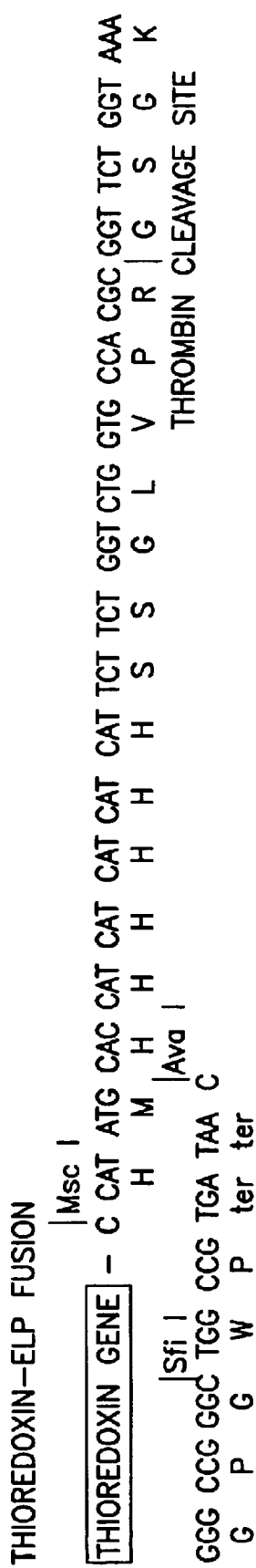

FIG. 11 shows the modified pET-32b vector for production of thioredoxin-ELP fusions.

Figure 12:
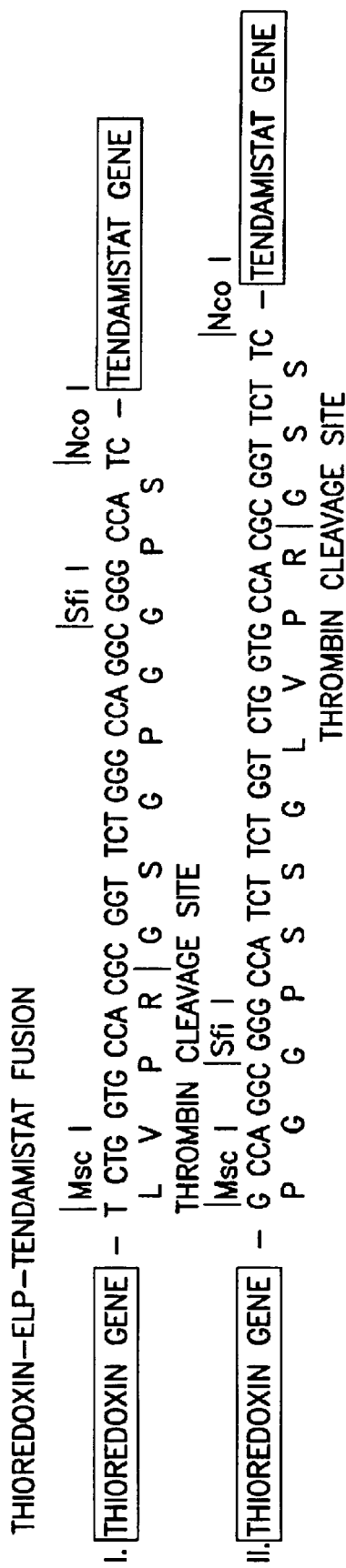

FIG. 12 shows the modified pET-32a vectors for the production of the thioredoxin-ELP-tendamistat fusion with alternate thrombin recognition sites.

Figure 13:
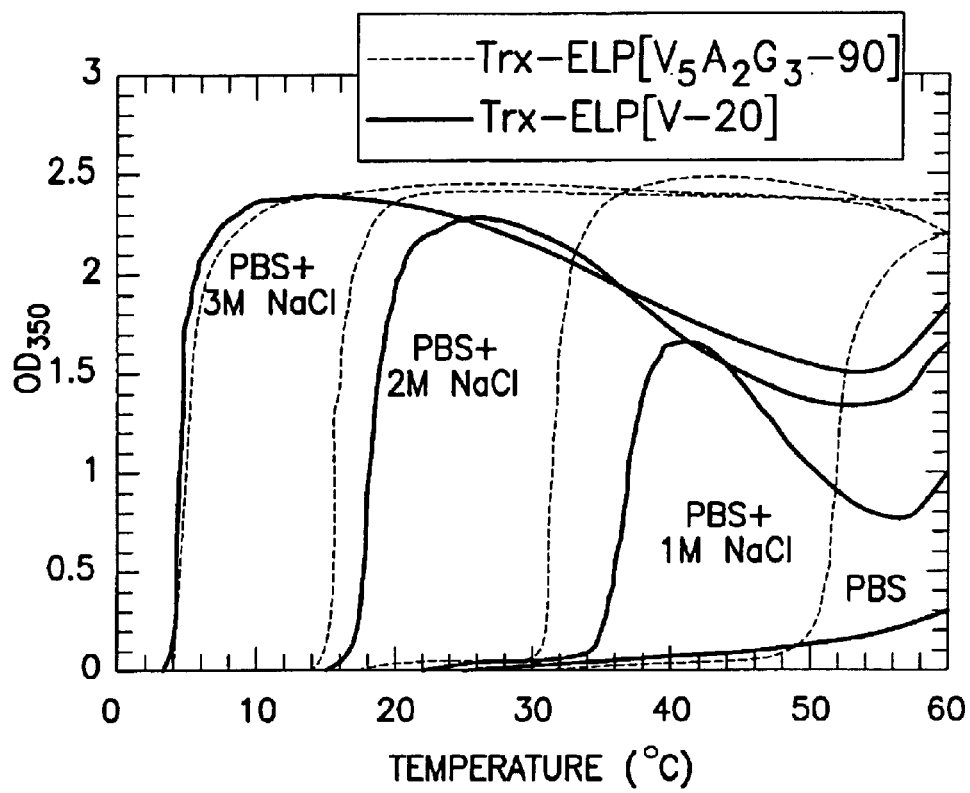

FIG. 13 is a graph of optical density at 350 nm as a function of temperature for solutions of the thioredoxin-ELP fusion proteins.

Figure 14:
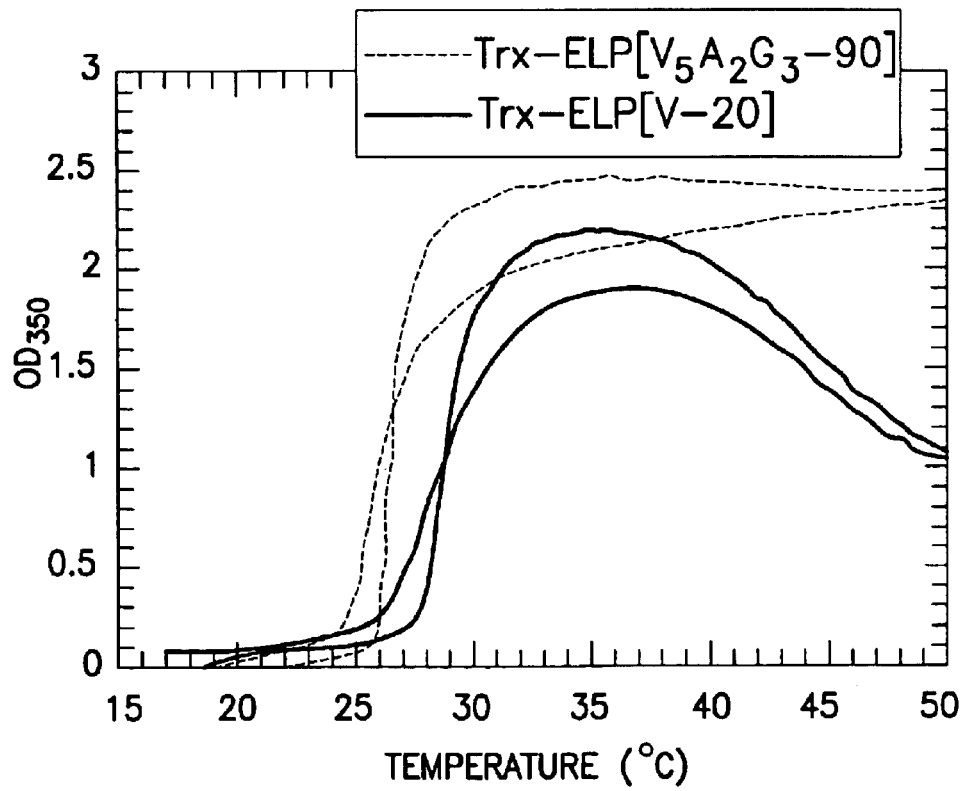

FIG. 14 is a graph showing the heating and cooling turbidity profiles for the solution conditions used in ITC purification, for solutions of thioredoxin-ELP[V-20] (solid lines) and thioredoxin-ELP[V$_5$A$_2$G$_3$-90] (dashed lines) at lysate protein concentrations in PBS with 1.3 M NaCl.

Figure 15:
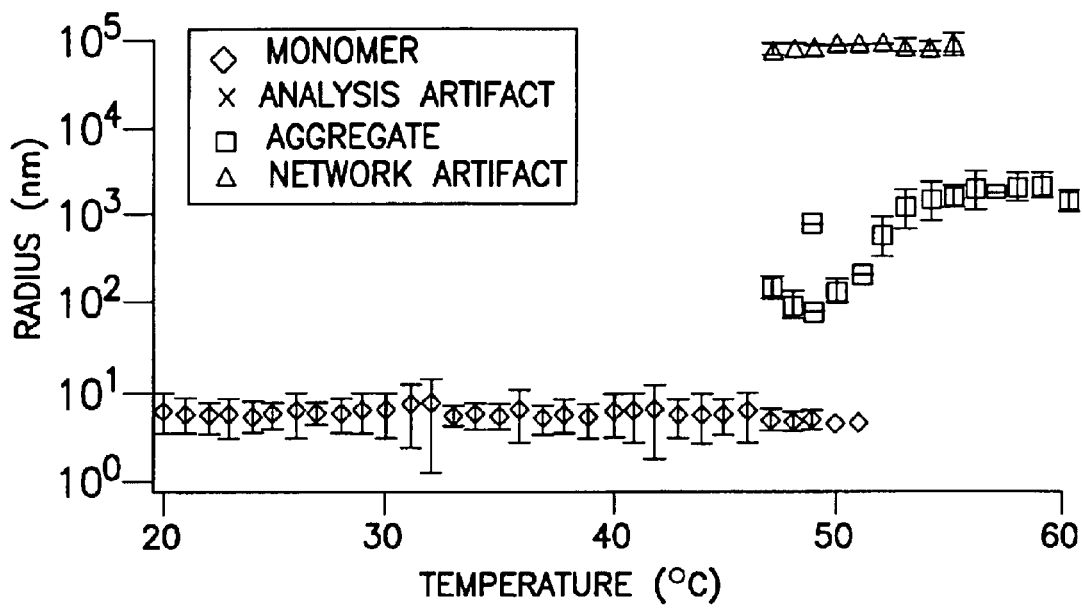
Figure 16:
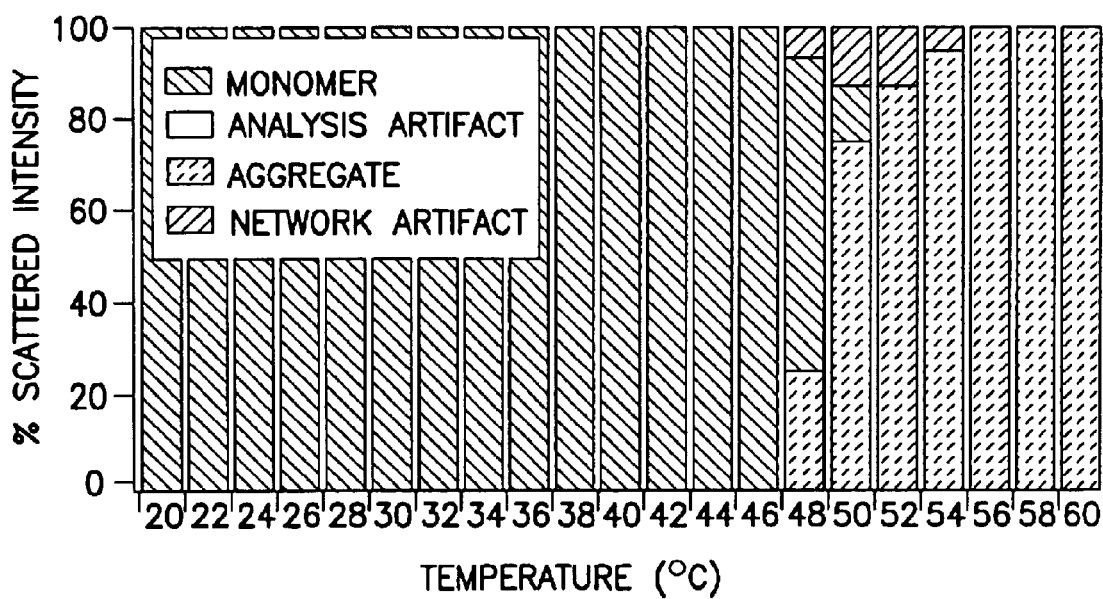
Figure 17:
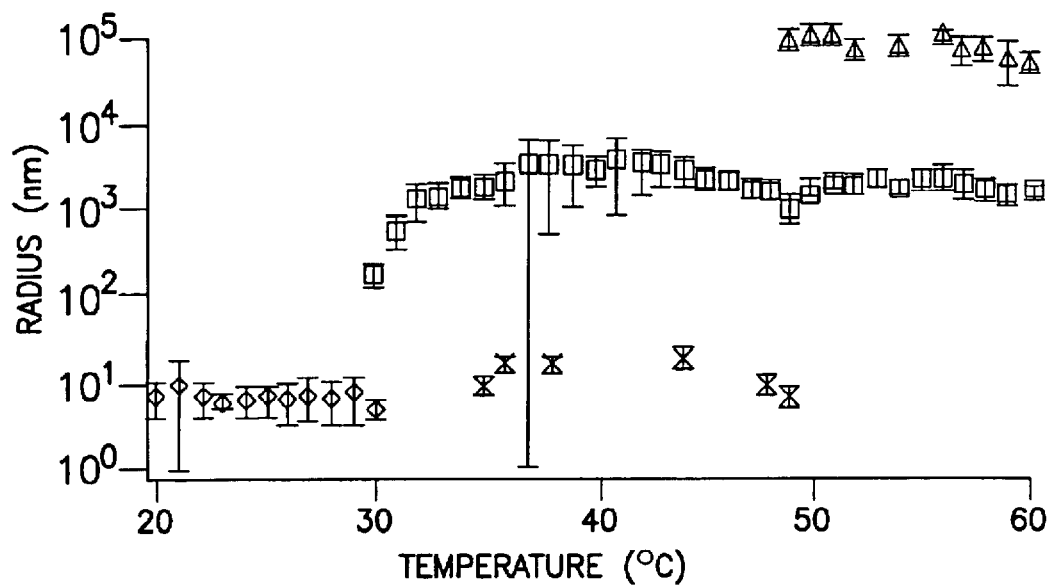
Figure 18:
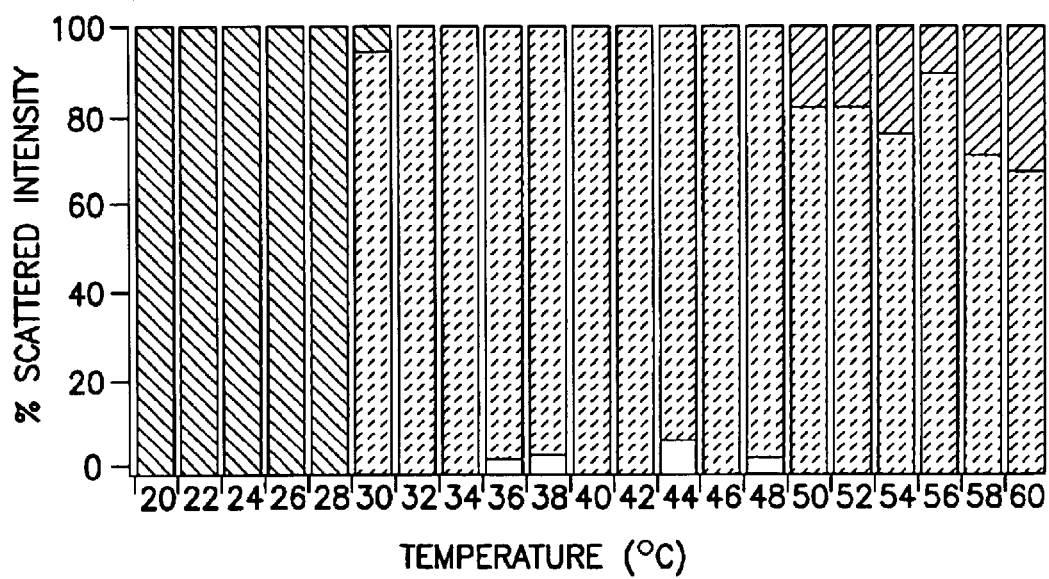
Figure 19:
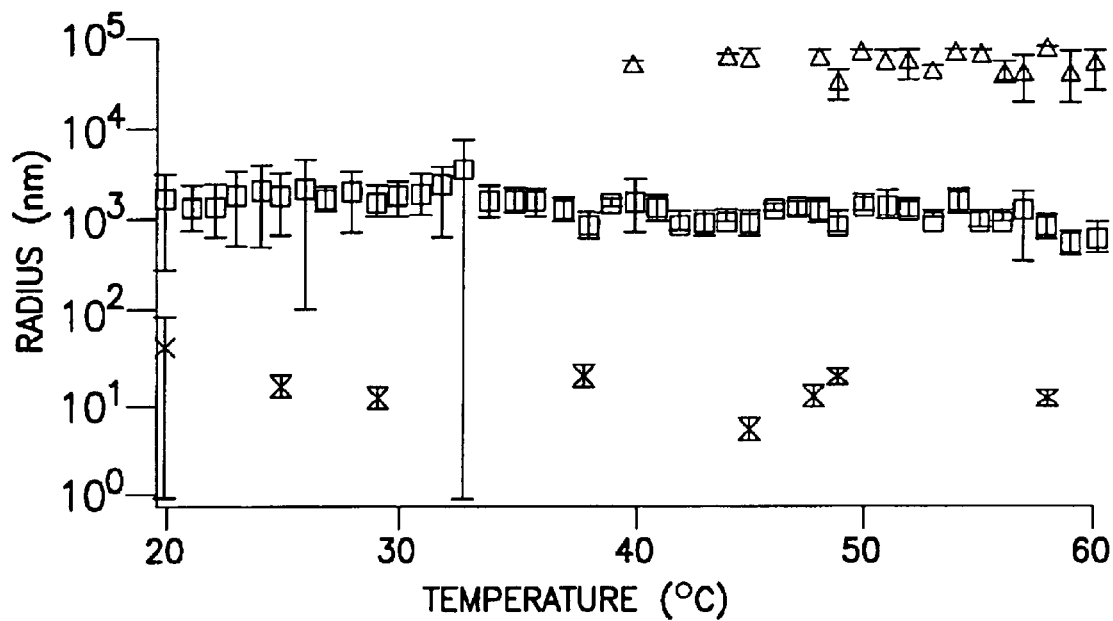
Figure 20:
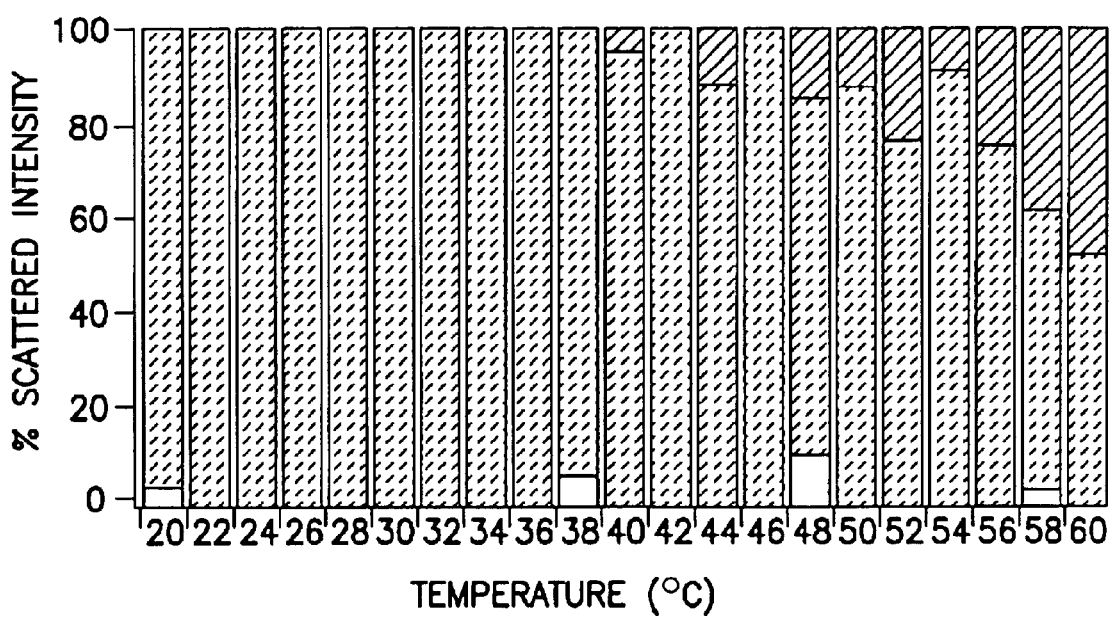

FIGS. 15–20 illustrate the effect of temperature on the particle size distribution of ELP[V$_5$A$_2$G$_3$-90] in PBS (FIGS. 15 and 16), PBS+1 M NaCl (FIGS. 17 and 18), and PBS+2 M NaCl (FIGS. 19 and 20). FIGS. 15, 17 and 19 show the effect of temperature on particle sizes of monomers (diamonds) and aggregates (squares). Analysis artifacts (stars) and network contributions (triangles), which may result from the coordinated slow movements of a network of smaller particles, are also shown (see text for discussion). FIGS. 16, 18 and 20 show the percentage of the scattered intensity attributed to each type of particle as a function of temperature.

Figure 21:
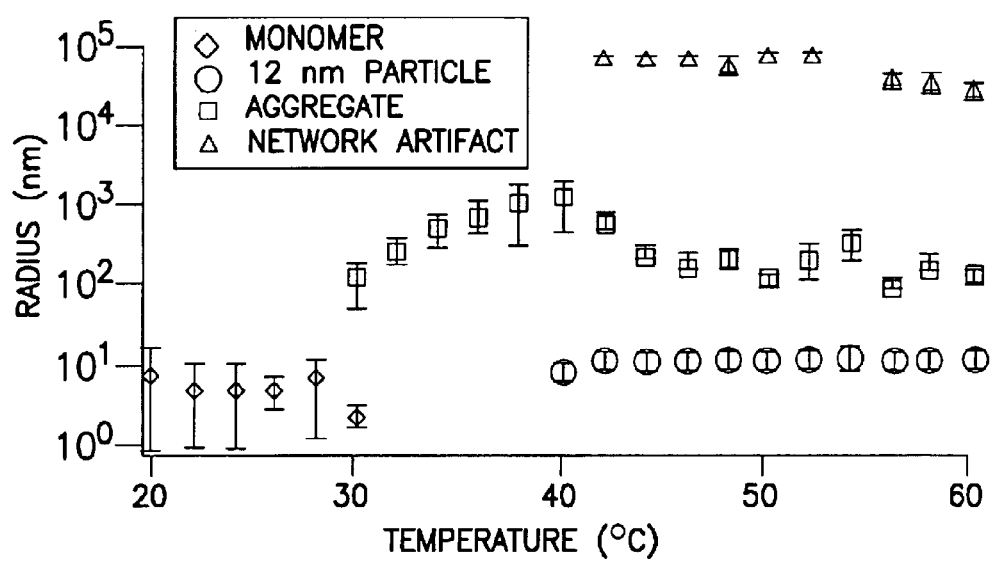
Figure 22:
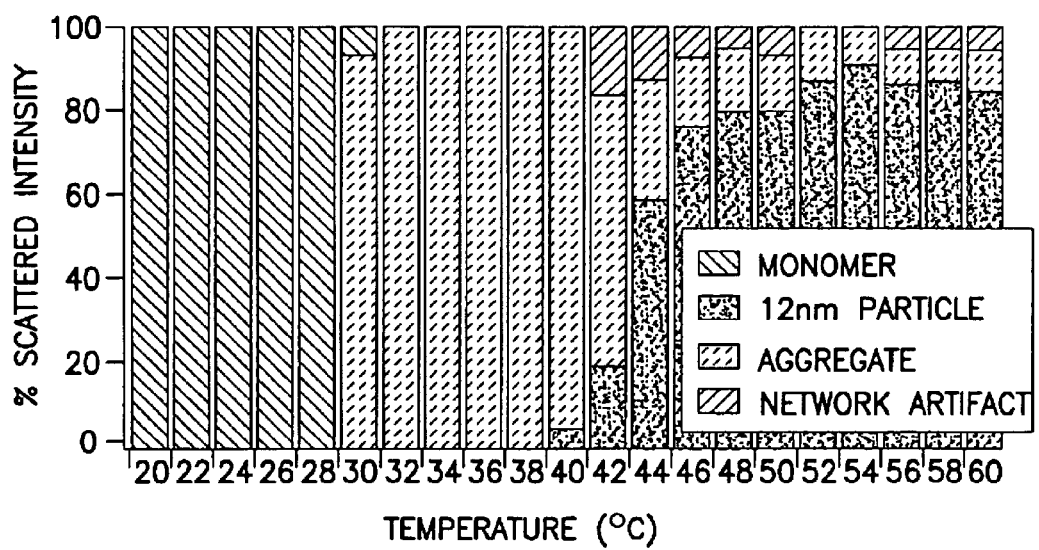
Figure 23:
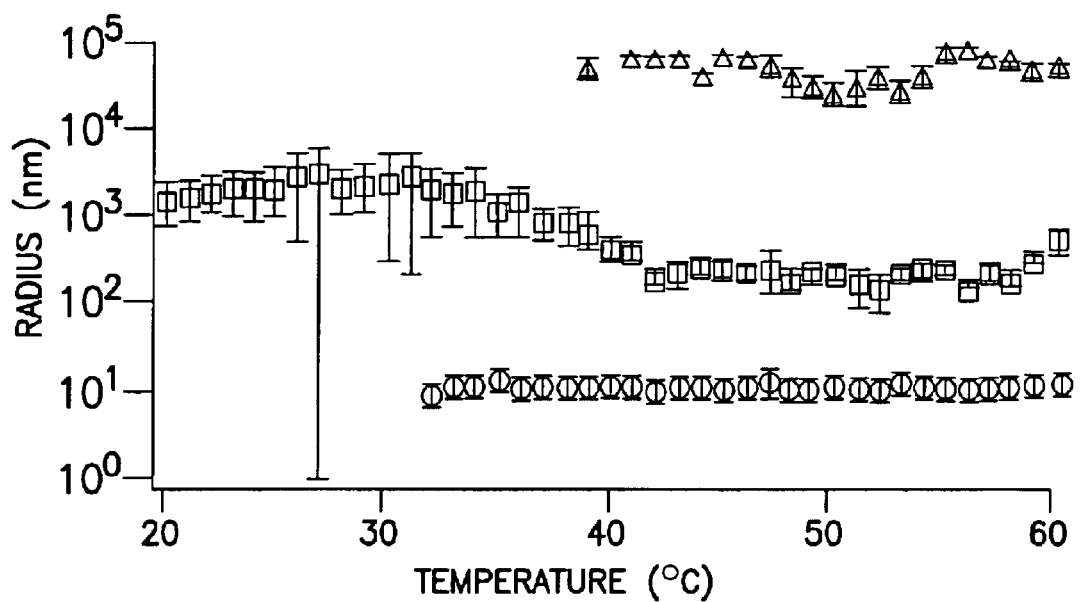
Figure 24:
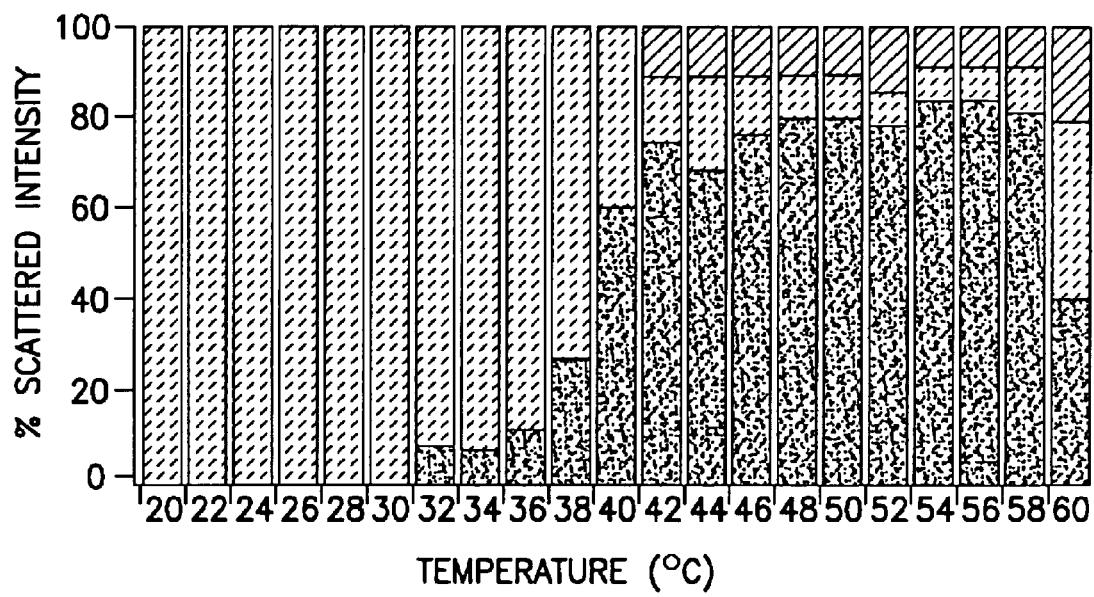

FIGS. 21–24 show the effect of temperature on the particle size distribution of ELP[V-20] in PBS+1 M NaCl (FIGS. 21 and 22) and PBS+2 M NaCl (FIGS. 23 and 24). FIGS. 21 and 23 show the effect of temperature on particle sizes of monomers (diamonds), 12 nm particles (circles), and larger aggregates (squares). Network contributions are also shown (triangles). FIGS. 22 and 24 show the percentage of the scattered intensity attributed to each type of particle as a function of temperature.

Figure 25:
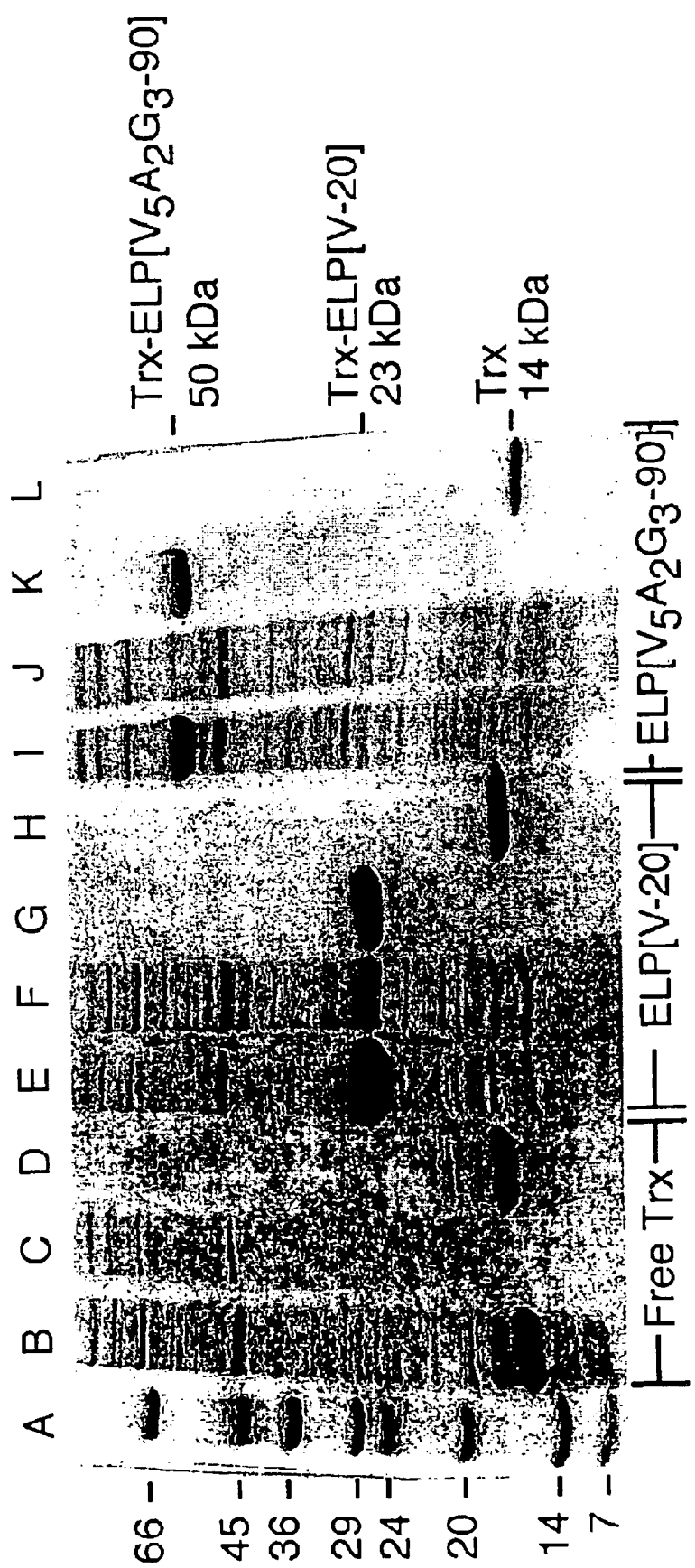

FIG. 25 shows SDS-PAGE analysis of ITC purification. Lane A shows a molecular weight marker, labeled in kDa. Lanes B-D show IMAC purification of free thioredoxin (His$_6$), and Lanes E-H and I-L show ITC purification of thioredoxin-ELP[V-20] and thioredoxin-ELP[V$_5$A$_2$G$_3$-90], respectively. Lanes B, E, and I are the soluble cell lysate. Lanes C and D are the IMAC column flow-through and elution product, respectively. For ITC purification, lanes F and J are the supernatant after inverse transition and centrifugation; lanes G and K are the pellet containing the target protein, after redissolving in PBS; and lanes H and L are the purified target protein thioredoxin, after cleavage with thrombin and separation from its ELP tag by a second round of ITC.

Figure 26:
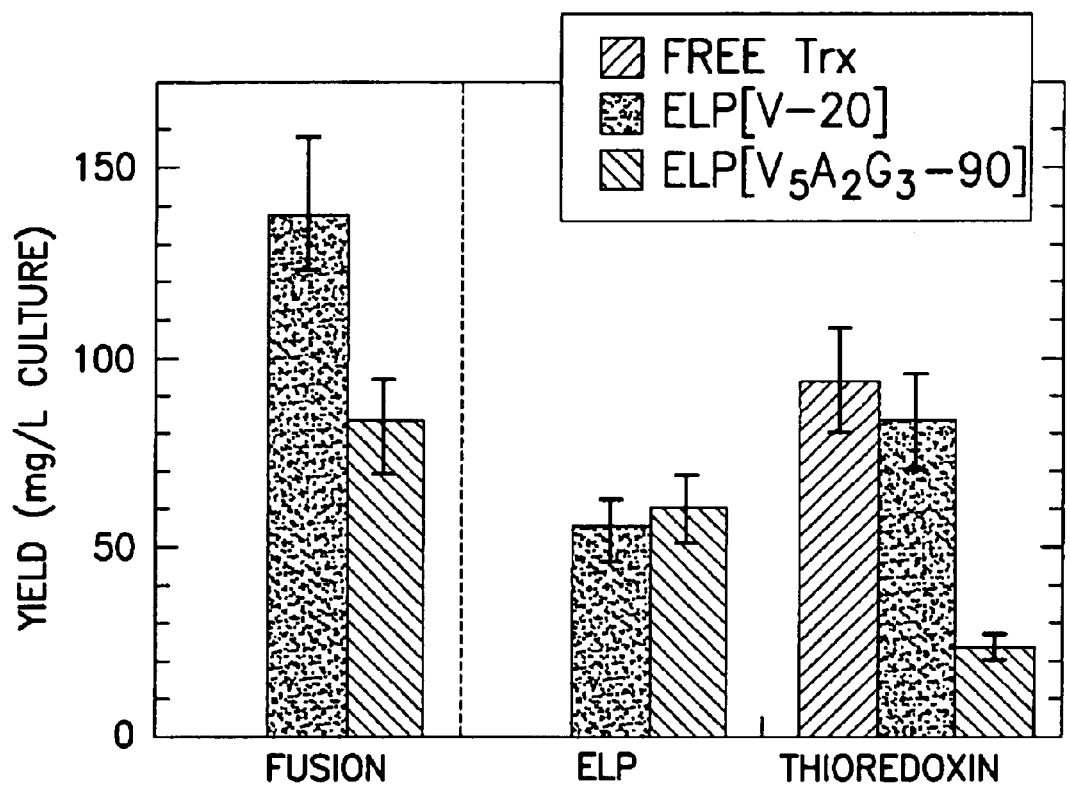

FIG. 26 is a graph of purified protein yield. The total yields of the thioredoxin(His$_6$), thioredoxin-ELP[V-20], and thioredoxin-ELP[V$_5$A$_2$G$_3$-90] from the 50 ml test cultures are shown, extrapolated to milligrams per liter of culture (mean±SD, n=4). The separate contributions of the ELP tag and thioredoxin to the yield, as calculated using their respective mass fractions of the fusion protein, are also shown for comparison.

Figure 27:
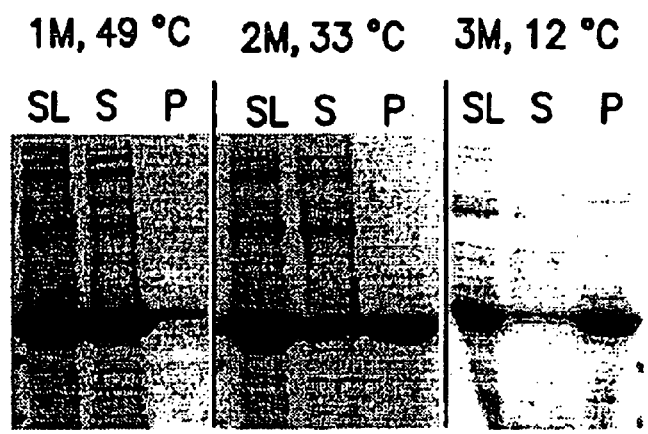

FIG. 27 shows SDS-PAGE analysis of the effect of NaCl concentration and centrifugation temperature on purification of thioredoxin-ELP[V-20] by ITC: SL=soluble cell lysate; S=supernatant after inverse transition of fusion protein and centrifugation to remove aggregated target protein; and P=redissolved pellet containing the purified fusion protein, after dissolution in PBS. The molar NaCl concentration and centrifugation temperature for each purification is noted at top.

Figure 28:
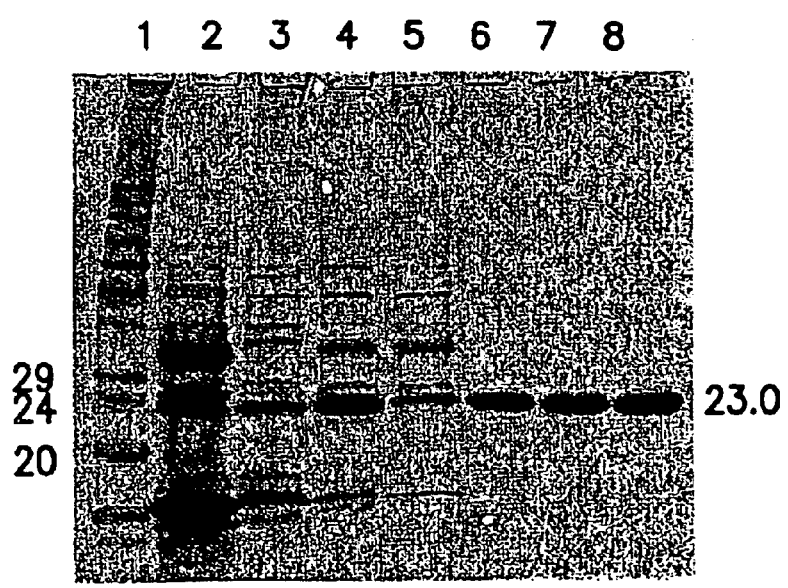

FIG. 28 is an SDS-PAGE gel of the stages of high throughput protein purification using microplates and inverse transition cycling according to the above-described procedure, in which ELP/thioredoxin fusion protein was purified (Lane 1: molecular mass markers (kDa) (Sigma, wideband; Lane 2: crude lysate; Lane 3: insoluble proteins; Lane 4: soluble lysate; Lane 5: supernatant containing contaminant proteins; Lane 6: purified ELP/thioredoxin fusion protein; and Lanes 7 and 8: purified ELP/thioredoxin fusion proteins from other wells).

Figure 29:
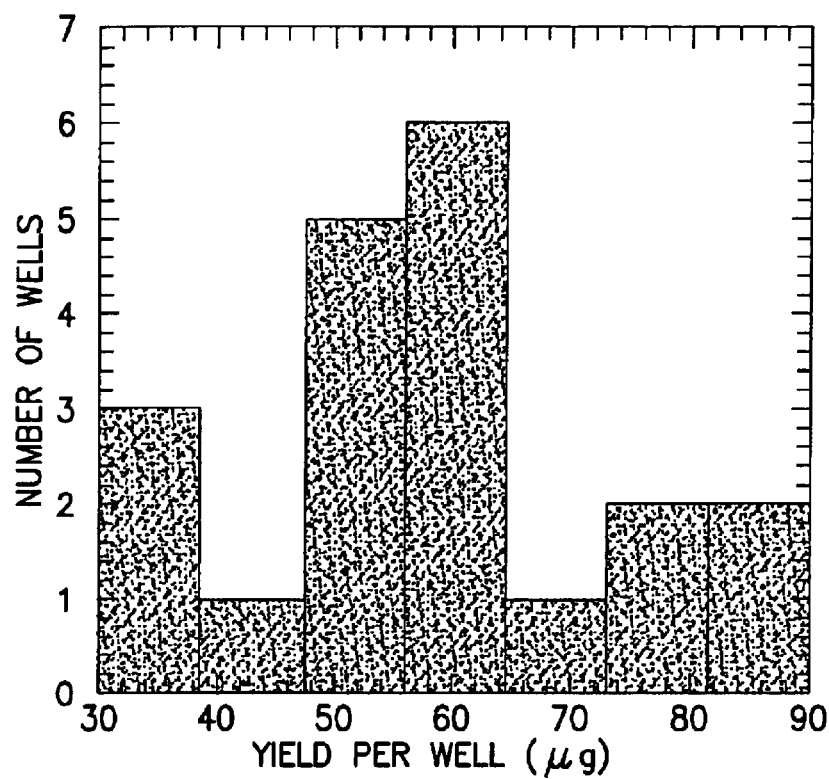

FIG. 29 is a histogram of total fusion protein per well as determined using absorbance measurements ($A_{280}$, $\epsilon$=19, 870) (n=20, $\mu$=32.97, $\sigma$=8.48).

Figure 30:
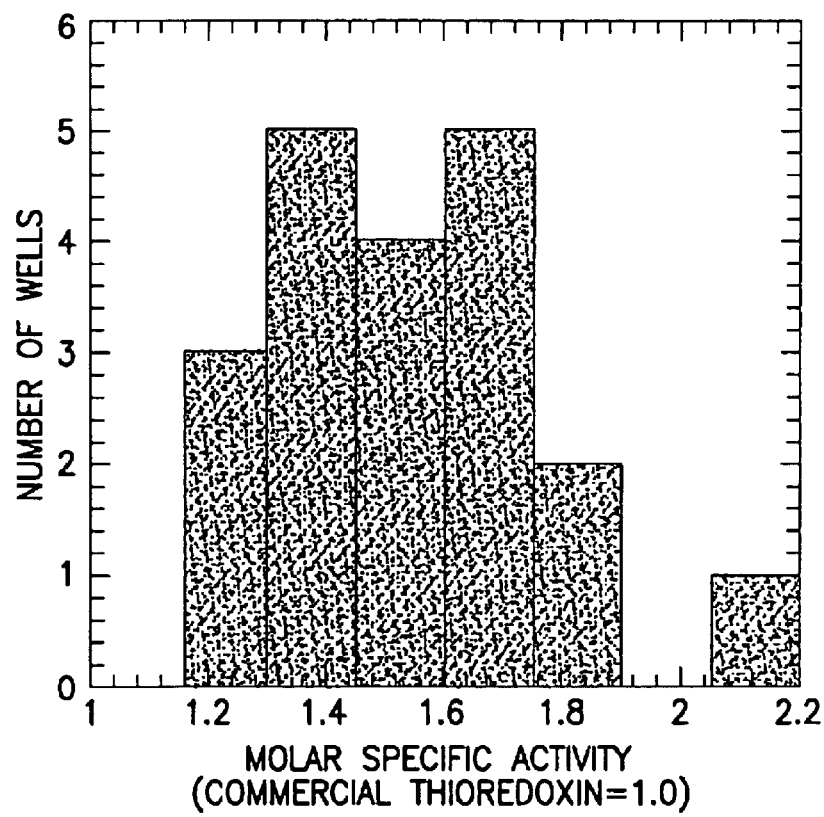

FIG. 30 is a histogram of fusion protein functionality/purity for each sample compared to commercial thioredoxin (from Sigma) (n=20, $\mu$=110.37%, $\sigma$=16.54%).

5. DETAILED DESCRIPTION OF THE INVENTION

The invention generally provides a fusion protein (FP) exhibiting a phase transition, the fusion protein comprising: (a) one or more biological molecules; (b) one or more proteins exhibiting a phase transition joined to the biologically active molecule(s); and (c) optionally, a spacer sequence separating any of the protein(s) of (b) from any of the biological molecule(s) of (a). The phase transition component of the FPs is preferably an ELP as described herein.

The invention also relates to methods of isolating and/or partially purifying the FPs and optionally, further cleaving and isolating the biological molecule component of the FPs, as well as high-throughput purification applications of the methodology of the invention.

5.1 Protein with Phase Transition Characteristics

The FPs of the invention comprise an amino acid sequence encoding a FP with phase transition characteristics.

The phase transition component of the FP may comprise a β-turn component. The β-turn component is suitably derived from pentapeptide repeats found in mammalian elastin, such as elastin-like peptides (ELPs). Examples of polypeptides suitable for use as the β-turn component are described in Urry, et al. International Patent Application PCT/US96/05186.

Preferred ELPs are oligomeric repeats of the pentapeptide Val-Pro-Gly-X-Gly, where the guest residue X is any amino acid that does not eliminate the phase transition characteristics of the ELP. X may be a naturally occurring or non-naturally occurring amino acid. For example, X may be selected from the group consisting of: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine. In one aspect of the invention X is not proline.

X may be a non-classical amino acid. Examples of non-classical amino acids include: D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general.

It will be appreciated by those of skill in the art that the ELPs need not consist of only Val-Pro-Gly-X-Gly in order to exhibit the desired phase transition. The oligomeric repeats may be separated by one or more amino acid residues that do not eliminate the phase transition characteristic of the FP. In a preferred aspect of the invention, the ratio of Val-Pro-Gly-X-Gly oligomeric repeats to other amino acid residues of the ELP is greater than about 75%, more preferably, the ratio is greater than about 85%, still more preferably, the ratio is greater than about 95%, and most preferably, the ratio is greater than about 99%.

Another preferred ELP comprises polymeric units having IPGXG Sequence ID No. 2), where X is as defined above.

Preferred ELPs are those that provide the FP with a transition temperature ($T_t$) that is within a range that permits the FP to remain soluble while being produced in a recombinant organism. It will be understood by one of skill in the art that the preferred $T_t$ will vary among organisms in respect of their temperature requirements for growth. For example, where the microbe used to culture the FP is *E. coli,* the preferred $T_t$ is from about 37.5 to about 42.5° C. in water, preferably about 40° C. in water. Useful and preferred temperatures can be readily determined by one of skill in the art for any organism on the basis of the description herein.

Preferred transition temperatures are those that permit solubility in the recombinant organism during culturing and permit aggregation of the FP by a small increase in temperature following cell lysis. For example, a preferred difference between the culture temperature and the $T_t$ is in the range of about 30 to about 40° C. In another aspect, the temperature increase is in the range of about 1 to about 7.5° C.; more preferably, the required temperature increase is in the range of about 1 to about 5° C.

Previous studies by Urry and colleagues have shown that the fourth residue (X) in the elastin pentapeptide sequence, VPGXG, can be altered without eliminating the formation of the β-turn. These studies also showed that the $T_t$ is a function of the hydrophobicity of the guest residue. By varying the identity of the guest residue(s) and their mole fraction(s), ELPs can be synthesized that exhibit an inverse transition over a 0–100° C. range.

The $T_t$ at a given ELP length can be decreased by incorporating a larger fraction of hydrophobic guest residues in the ELP sequence. Examples of suitable hydrophobic guest residues include valine, leucine, isoleucine, phenylalanine, tryptophan and methionine. Tyrosine, which is moderately hydrophobic, may also be used. Conversely, the $T_t$ can be increased by incorporating residues, such as those selected from the group consisting of: glutamic acid, cysteine, lysine, aspartate, alanine, asparagine, serine, threonine, glysine, arginine, and glutamine; preferably selected from alanine, serine, threonine and glutamic acid.

The ELP is preferably selected to provide the FP a $T_t$ ranging from about 10 to about 80° C., more preferably from about 35 to about 60° C., most preferably from about 38 to about 45° C. However, as stated above, the preferred $T_t$ varies with the required culture conditions of the organism in which the FP will be cultured.

The $T_t$ can also be varied by varying ELP chain length. The $T_t$'s of the higher molecular weight ELPs discussed in Section 6 approached 42° C. for the thioredoxin/180-mer fusion (at 25 μM in PBS). The $T_t$ increased dramatically with decreasing MW. In low ionic strength buffers, the $T_t$'s of the lower molecular weight ELPs are often too high for protein purification. A high concentration of NaCl can be used to decrease the $T_t$ to a useful temperature.

For polypeptides having a molecular weight >100,000, the hydrophobicity scale developed by Urry et al. (PCT/US96/05186) is preferred for predicting the approximate $T_t$ of a specific ELP sequence. For polypeptides having a molecular weight <100,000, the $T_t$ is preferably determined by the following quadratic function:

$$T_t = M_0 + M_1 X + M_2 X^2$$

where X is the MW of the FP, and $M_0 = 116.21$; $M_1 = -1.7499$; $M_2 = 0.010349$.

The regression coefficient for this fit is 0.99793 (see FIG. 5, discussed more fully hereinafter).

ELP chain length is also important with respect to protein yields. In addition to the decreased total yield of expressed fusion protein observed with increasing ELP MW, the weight percent of target protein versus the ELP also decreases as the MW of the ELP carrier increases. In a preferred aspect of the invention, the ELP length is from 5 to about 500 amino acid residues, more preferably from about 10 to about 450 amino acid residues, and still more preferably from about 15 to about 150 amino acid residues. ELP length can be reduced while maintaining a target $T_t$ by incorporating a larger fraction of hydrophobic guest residues in the ELP sequence.

Reduction of the size of the ELP tag may be employed to substantially increase the yield of the target protein, as shown by the results presented hereinafter, wherein reduction of the ELP tag from 36 to 9 kDa increased the expression yield of thioredoxin by a factor of four, to a level comparable to free thioredoxin expressed without an ELP tag, while still allowing efficient and effective purification.

Truncation of the ELP tag, however, results in more complex transition behavior than observed with larger tags. In the case of thioredoxin, dynamic light scattering experiments showed that for both tags, large aggregates with hydrodynamic radii of ~2 μm formed as the temperature was raised to above $T_t$. These aggregates persisted at all temperatures above the $T_t$ for the thioredoxin fusion with the larger 36 kDa ELP tag. With the 9 kDa tag, however, smaller particles with hydrodynamic radii of ~12 nm began to form at the expense of the initial larger aggregates as the temperature was raised further above the $T_t$.

Since only large aggregates can be effectively retrieved by centrifugation, efficient purification of fusion proteins with short ELP tags requires selection of solution conditions that favor the formation of the larger aggregates. Despite this additional complexity, the ELP tag can be successfully truncated to enhance the yield of a target protein without compromising purification.

5.2 Protein Component of the Fusion Protein

The FP of the invention comprises a protein of interest. The protein of interest is preferably a biologically active protein. For example, suitable proteins include those of interest in medicine, agriculture or other scientific or industrial fields. Examples of suitable proteins include enzymes utilized in replacement therapy; hormones for promoting growth in animals, or cell growth in cell culture; and active proteinaceous substances used in various applications, e.g., in biotechnology or in medical diagnostics. Specific examples include superoxide dismutase, interferon, asparaginease, glutamase, arginase, arginine deaminase, adenosine deaminase ribonuclease, trypsin, chromotrypsin, papin, insulin, calcitonin, ACTH, glucagon, somatosin, somatropin, somatomedin, parathyroid hormone, erthyropoietin, hypothalamic releasing factors, prolactin, thyroid stimulating hormones, endorphins, enkephalins, and vasopressin.

In one aspect of the invention, the protein of interest is a soluble, over-expressed protein, such as thioredoxin. Thioredoxin is expressed as soluble protein at high levels in *E. coli* and is therefore an exemplary model for verifying that the reversible, soluble-insoluble inverse transition of the ELP tag is retained in a fusion protein. Thioredoxin also exhibits useful pharmaceutical properties and other industrially useful properties, for example, as described in U.S. Pat. Nos. 5,985,261; 5,952,034; 5,919,657; 5,792,506; 5,646,016; and 5,028,419.

In another aspect of the invention, the protein of interest is an insoluble, poorly expressed protein, such as tendamistat. Tendamistat is predominately expressed as insoluble protein in inclusion bodies. Although fusion with thioredoxin is known to promote the soluble expression of target proteins, the inventor has observed that only 5–10% of over-expressed thioredoxin-tendamistat fusion protein is recovered as soluble and functionally-active protein. It was initially expected that incorporation of a hydrophobic ELP sequence in a fusion protein that exhibits a pronounced tendency to form inclusion bodies might (1) exacerbate its irreversible aggregation in vivo during culture, and (2) cause irreversible aggregation in vitro during purification by inverse transition cycling. Surprisingly, neither problem was encountered with the ELP-tendamistat fusion protein.

The tendamistat-ELP fusion protein provides a readily-isolated, active version of tendamistat for use as an α-amylase inhibitor, e.g., in the treatment of pancreatitis. This fusion is suitably provided as a component of a pharmaceutical formulation in association with a pharmaceutically acceptable carrier.

The inventors have surprisingly discovered that the protein component of the FPs (illustratively represented here by tendamistat and thioredoxin) retained some or all of the biological activity of the native protein. For example, a comparison of the activity of a thioredoxin-ELP fusion with commercially-obtained *E. coli* thioredoxin showed that the thioredoxin-ELP fusion protein retains activity without requiring cleavage of the ELP carrier.

Moreover, altering solution conditions to effect isolation of the FPs did not affect the stability and activity of the FPs after transition cycling. For example, aggregation of the ELP-thioredoxin fusion above the $T_t$ did not irreversibly denature the fusion protein. In fact, thioredoxin activity was completely retained after several rounds of inverse transition cycling.

Similarly, tendamistat fusion retained most of its α-amylase inhibition activity, and after thrombin cleavage and removal of the ELP carrier, tendamistat regained complete activity.

These results are consistent with the surprising conclusion that desolvation and aggregation of the ELP will not result in complete loss of activity of the protein of interest.

5.3 Other Components of the Fusion Protein

The β-turn and protein components of the FPs of the invention may be separated by a spacer comprising one or more amino acid residues. In one embodiment, the spacer is an amino acid sequence recognizable by a specific protease. Examples include sequences cleavable by serine, cysteine (thiol), aspartyl (carboxyl) or metallo-proteases. Such separation permits the phase transition component of the FP to be enzymatically cleaved to enable isolation and/or partial purification of the protein of interest.

The FP may be engineered to comprise a signal sequence that causes the FP to be directed to the cell surface or excreted from a recombinant organism that is used to produce the FP. The FP may be cleaved at the cell surface or may be enzymatically cleaved in solution.

The FP may also contain a sequence that permits separate purification by affinity chromatography, commonly referred to as affinity tags. Examples include (His), tag, FLAG, s-tag, etc.

The FP may also contain a "detection tag," i.e., a sequence that is retained on the protein of interest after cleavage of the phase transition component and which by virtue of binding to a reporter molecule can be used to detect the protein of interest (e.g., antibody epitopes for Western blot).

Also included within the scope of the invention are derivatives comprising FPs, which have been differentially modified during or after synthesis, e.g., by benzylation, glycosylation, acetylation, phosphorylation, amidation, PEGylation, derivatization by known protecting/blocking groups, proteolytic cleavage, linkage to an antibody molecule or other cellular ligand, etc. In one embodiment, the FPs are acetylated at the N-terminus and/or amidated at the C-terminus. In another embodiment, the FPs are conjugated to polymers, e.g., polymers known in the art to facilitate oral delivery, decrease enzymatic degradation, increase solubility of the polypeptides, or otherwise improve the chemical properties of the therapeutic polypeptides for administration to humans or other animals. The polymers may be joined to the FPs by hydrolyzable bonds. For example, in one aspect where the FPs are therapeutically active, the polymers are joined to the FPs by hydrolyzable bonds, so that the polymers are cleaved in vivo to yield the active therapeutic FPs.

5.4 Methods for Preparing the Fusion Proteins

The FPs of the invention can be obtained by known recombinant expression techniques. To recombinantly produce an FP, a nucleic acid sequence encoding a FP is operatively linked to a promoter such that the FP is produced from the sequence. Preferred promoters are those useful for expression in *E. coli*, such as the T7 promoter. In a preferred embodiment, the nucleic acid is DNA.

Any commonly used expression system may be used, e.g., eukaryotic or prokaryotic systems. Specific examples include yeast, pichia, mammalian, and bacterial systems, such as *E. coli*, and *Caulobacter*.

A vector comprising the nucleic acid sequence can be introduced into a cell for expression of the FP. The vector can remain episomal or become chromosomally integrated, as long as it can be transcribed to produce the desired RNA. Vectors can be constructed by standard recombinant DNA technology methods. Vectors can be plasmid, viral, or other types known in the art, used for replication and expression in eukaryotic or prokaryotic cells.

It will be appreciated by one of skill in the art that a wide variety of components known in the art may be included in the vectors of the present invention, including a wide variety of transcription signals, such as promoters and other sequences that regulate the binding of RNA polymerase to the promoter. The operation of promoters is well known in the art.[21]

Any promoter known to be effective in the cells in which the vector will be expressed can be used to initiate expression of the FP. Suitable promoters may be inducible or constitutive. Examples of suitable promoters include the SV40 early promoter region, the promoter contained in the 3' long terminal repeat of Rous sarcoma virus, the HSV-1 (herpes simplex virus-1) thymidine kinase promoter, the regulatory sequences of the metallothionein gene, etc., as well as the following animal transcriptional control regions, which exhibit tissue specificity and have been utilized in transgenic animals: elastase I gene control region which is active in pancreatic acinar cells; insulin gene control region which is active in pancreatic beta cells, immunoglobulin gene control region which is active in lymphoid cells, mouse mammary tumor virus control region which is active in testicular, breast, lymphoid and mast cells, albumin gene control region which is active in liver, alpha-fetoprotein gene control region which is active in liver, alpha 1-antitrypsin gene control region which is active in the liver, beta-globin gene control region which is active in erythroid cells, myelin basic protein gene control region which is active in oligodendrocyte cells in the brain, myosin light chain-2 gene control region which is active in skeletal muscle, and gonadotropin releasing hormone gene control region which is active in the hypothalamus.

In one aspect of the invention, a mammal is genetically modified to produce the FP in its milk. Techniques for performing such genetic modifications are described in U.S. Pat. No. 6,013,857, issued Jan. 11, 2000, for "Transgenic Bovines and Milk from Transgenic Bovines." The genome of the transgenic animal is modified to comprise a transgene comprising a DNA sequence encoding an FP operably linked to a mammary gland promoter. Expression of the DNA sequence results in the production of FP in the milk. The FP peptides may then be isolated by phase transition from milk obtained from the transgenic mammal. The transgenic mammal is preferably a bovine.

5.5 Method for Isolating and/or Partially Purifying Recombinant Proteins and Other Applications The invention provides a method for isolating and/or partially purifying recombinantly produced proteins. The method generally comprises preparing a nucleic acid as described in section 5.4, lysing the cells of the cell culture and isolating the FP from solution by inverse transition. Where the FP is secreted from live cells, it will not be necessary to lyse the cells.

The FPs of the invention can be separated from other contaminating proteins to high purity using a transition cycling procedure. Methods of isolation can employ the temperature-dependent solubility of the FP. The inventor has surprisingly discovered that soluble FP can be selectively aggregated by raising the solution temperature above the $T_t$ with no effect on other soluble proteins present in the cell lysate. Successive inverse phase transition cycles may be used to obtain a higher degree of purity.

Other purification techniques may also be employed in conjunction with the inverse phase transition. For example, recombinant cells may be designed to secrete the FP; the cells may be cultured in a cross-flow filter system that permits the secreted FP proteins to diffuse across a membrane. The FPs may then be purified from other contaminants by inverse phase transition.

Inverse phase transition can also be induced by depressing the $T_t$ by manipulating other solution conditions. For example, the $T_t$ can be adjusted so that soluble fusion protein can be isothermally aggregated at room temperature, for example, by the addition of salt. Because this process is reversible, altering the solution conditions back to the original conditions results in the recovery of soluble, pure, and functionally-active fusion protein.

The inverse transition of the ELP also provides a simple method for purifying the ELP tag from the target protein after cleavage at a protease recognition site encoded in the primary amino acid sequence between the target protein and the ELP carrier. After cleavage, the target protein is easily separated from free ELP by another round of inverse transition cycling.

In addition to temperature and ionic strength, other environmental variables useful for modulating the inverse transition of FPs include pH, the addition of organic solutes and solvents, side-chain ionization or chemical modification, and pressure.

Although purification of recombinant proteins is the most obvious and immediate application of the FPs of the invention, the invention provides other applications in biotechnology and medicine.

In one embodiment, the protein component of the FP is an enzyme. Such enzyme-FPs (EFPs) may be used as substitutes for immobilized enzymes in industrial biocatalysis. The EFPs may be added to a solution to facilitate biocatalysis and then reisolated from the solution. The utilization of free EFPs rather than immobilized enzymes permits substantial increases in kinetics of the biocatalysis to be achieved. Furthermore, the EFPs facilitate both separation of the enzyme from product and recycling of the enzyme for subsequent rounds of biocatalysis.[22]

In another embodiment, the protein component of the FP is an antibody. Such antibody FPs (AFPs) can be employed for capture and subsequent isolation of an analyte from a solution, such as a biological fluid, and are useful in immunoassays.[23] The antibodies can be labeled (e.g., radiolabelled, labeled with fluorescent or luminescent tags) to facilitate assays, such as immunoassays.

Another application of FPs of the invention is for targeted delivery of therapeutics and imaging agents, where in concert with targeted hyperthermia, FP conjugated to radionuclides or protein therapeutics enables precise targeting for imaging and therapy.[24,25,26]

Figure 1:
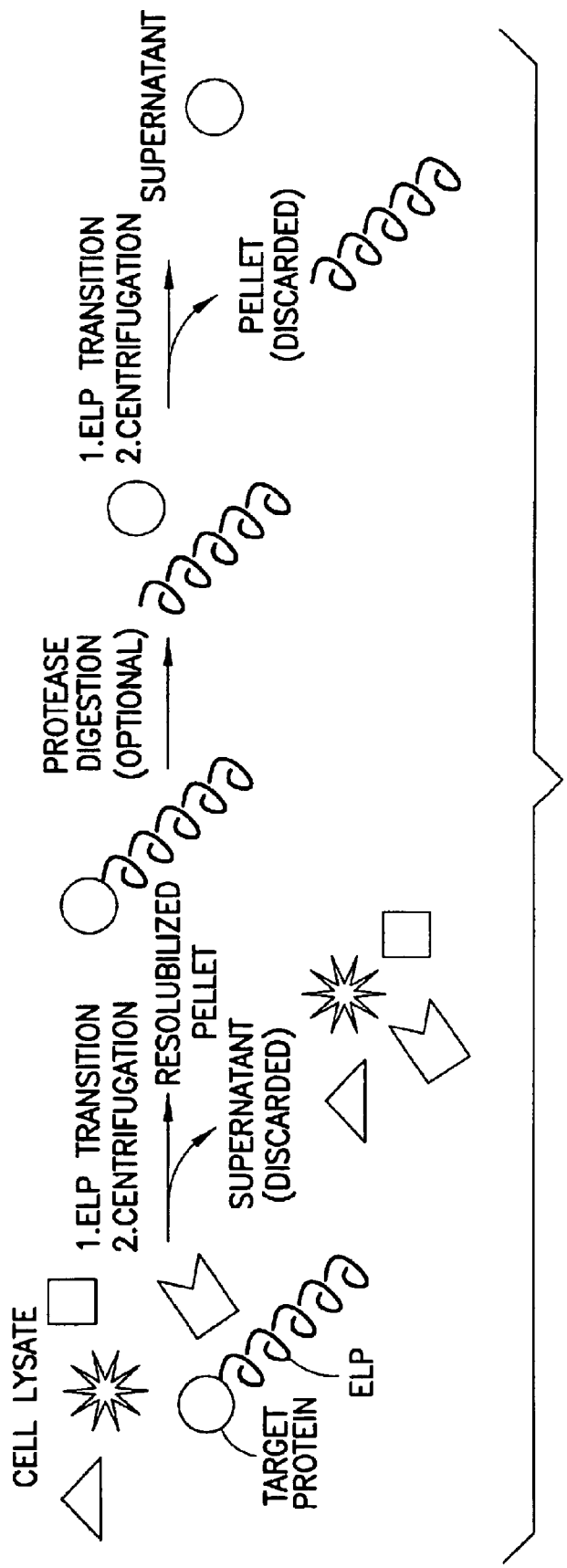
FIG. 1 shows an inverse transition cycling purification scheme, in which a target protein fused to an ELP sequence is separated from other contaminating proteins by inducing the ELP inverse phase transition.

FIG. 1 schematically shows an inverse transition cycling (ITC) purification scheme. A target protein, which is genetically fused to an ELP, is separated from other contaminating proteins in the cell lysate after inducing the ELP inverse temperature phase transition. The solution is first cycled The solution is first cycled to above the $T_t$ to selectively aggregate the target fusion protein so that it can be separated by centrifugation, and then cooled to below the $T_t$ to resolubilize the purified fusion protein. The target protein can be liberated from the fused ELP tag by cleavage at a specific protease recognition site engineered between the ELP tag and the target protein. The cleaved ELP can be removed by a final round of ITC. After centrifugation, the purified target protein is obtained in the supernatant, while the aggregated ELP is discarded in the pellet.

5.6 High Throughput Purification Using ITC

The ITC purification technique of the invention can be scaled down and multiplexed for concurrent, parallel laboratory scale purification from numerous cell cultures, to achieve simultaneous purification of proteins from multiple cultures. Such high-throughput purification application of the invention can be utilized, for example, to expedite both structure-function studies of proteins and the screening of proteins in pharmaceutical studies.

6. EXAMPLES

The principal features of the invention are more fully shown with illustrative reference to experiments involving the expression of recombinant proteins, thioredoxin and tendamistat, fused to an environmentally-responsive β-turn sequence. The results demonstrate a gentle, one-step separation of these fusion proteins from other soluble proteins by exploiting the inverse transition of the ELP sequence. Thioredoxin and tendamistat were chosen as target proteins because they exemplify two limiting scenarios of soluble protein expression: (1) the target protein over-expresses at high levels and is highly soluble (thioredoxin), and (2) the protein is expressed largely as insoluble inclusion bodies (tendamistat). It is preferable that proteins representative of this second class exhibit some level of expression as soluble protein to be purified by inverse transition cycling.

The thioredoxin-ELP fusion exhibited only a small increase in $T_t$ (1–2° C.) compared to free ELP, while the tendamistat fusion displayed a more dramatic 15° C. reduction in $T_t$. This shift was identical for both the ternary (thioredoxin-ELP-tendamistat) and binary (ELP-tendamistat) constructs, indicating that the $T_t$ shift was associated specifically with tendamistat. These observations are consistent with the conclusion that the decreased $T_t$ was due to interactions between the ELP chain and solvent-exposed hydrophobic regions in tendamistat, whereas, for the highly soluble thioredoxin, these hydrophobic interactions were negligible. Moreover, with highly soluble proteins only a small perturbation of $T_t$ relative to the free ELP is likely to be introduced upon fusion with an ELP tag.

In order to demonstrate fundamental concepts of the invention, a gene encoding an ELP sequence was synthesized and ligated into two fusion protein constructs (shown schematically in FIG. 1b). In the first construct, an ELP sequence was fused to the C-terminus of E. coli thioredoxin, a 109 residue protein that is commonly used as a carrier to increase the solubility of target recombinant proteins.[14] In the second, more complex construct, tendamistat, a 77 residue protein inhibitor of α-amylase,[27] was fused to the C-terminus of a thioredoxin-ELP fusion, forming a ternary fusion.

6.1 Preparation of the Fusion Protein

The objective in this example was to design a β-turn sequence with a predicted $T_t$ above 37° C. so that an FP would remain soluble under conditions used for E. coli culture, but which could be aggregated by a small increase in temperature. Previous studies by Urry and colleagues have shown that two ELP-specific variables, guest residue(s) composition[28] (i.e., identity and mole fraction of X in the VPGXG monomer) and chain length[29] of the ELP profoundly affect the transition temperature, and thereby provide design criteria to specify the $T_t$ for a specific application. Based on these studies, a gene was synthesized encoding an ELP sequence (Sequence ID No. 3) with guest residues valine, alanine, and glycine in the ratio 5:2:3, with a predicted $T_t$ of ~40° C. in water. The synthetic gene, which encoded 10 VPGXG pentapeptide repeats (the "10-mer"), was oligomerized up to 18 times to create a library of genes encoding ELPs with precisely-specified molecular weights (MWs) ranging from 3.9 to 70.5 kDa. To my knowledge, these are the first examples of genetically-engineered ELPs with precisely-defined chain length and amino acid sequence, which are designed to exhibit an inverse transition at a specified temperature. Thioredoxin was expressed as a N-terminal fusion with the 10-, 20-, 30-, 60-, 90-, 120-, 150-, and 180-mer ELP sequences, and tendamistat was expressed as a C-terminal fusion to thioredoxin/90-mer ELP (FIG. 1b).

The FPs were expressed in E. coli and purified from cell lysate either by immobilized metal affinity chromatography (IMAC) using a (histidine)$_6$ tag present in the fusion protein[30] or by inverse transition cycling (described below). The purified FP was cleaved with thrombin to liberate the target protein from the ELP. The ELP was then separated from the target protein by another round of inverse transition cycling, resulting in pure target protein. For each construct, the purified FP, target protein, and ELP were characterized by sodium dodecyl sulfate polyacrylamide gel electrophoresis (SDS-PAGE), which confirmed protein purity, verified completeness of thrombin cleavage, and showed that the migration of each protein was consistent with its predicted size (results not shown).

6.2 Characterization of Inverse Transition of the Fusion Proteins

The inverse transition can be spectrophotometrically-characterized by monitoring solution turbidity as a function of temperature, due to aggregation of the ELP as it undergoes the transition. As the temperature is raised up to a critical temperature, the solution remains clear. Further increase in temperature results in a sharp increase in turbidity over a ~2° C. range to a maximum value ($OD_{350}$~2.0). The $T_t$, defined as the temperature at the midpoint of the spectrophotometrically-observed transition, is a convenient parameter to describe this process.

Figure 2:
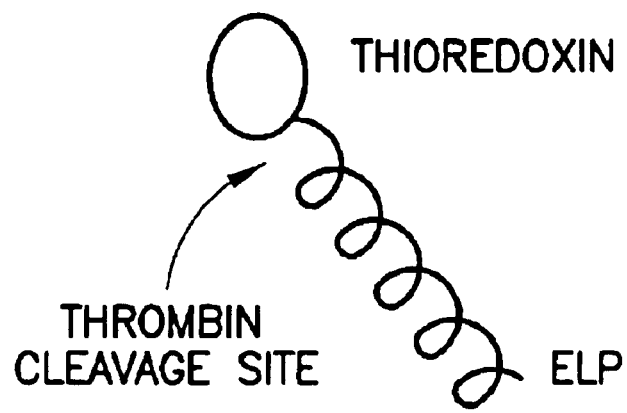
FIG. 2 is a schematic representation of the thioredoxin-ELP fusion protein showing the location of the thrombin cleavage site.

The inverse transition of free ELP, thioredoxin-ELP fusion, ELP-tendamistat fusion, and ternary thioredoxin-ELP-tendamistat fusion in PBS are shown in FIG. 2a. The $T_t$ was 51° C. for free ELP and 54° C. for the thioredoxin fusion, showing that the $T_t$ is only slightly affected by fusion to thioredoxin. Thioredoxin-ELP produced by cleavage from the ternary tendamistat fusion had a higher $T_t$ compared to thioredoxin-ELP produced directly (60° C. vs. 54° C.), presumably due to differences in the leader and trailer amino acid sequences immediately adjacent to the ELP sequence (see FIG. 5). The transition profiles of ELP-tendamistat and the thioredoxin-ELP-tendamistat were nearly identical, with a $T_t$ of 34° C. Aggregation of the FPs was reversible, and the aggregates were resolubilized completely upon lowering the temperature below the $T_t$. However, resolubilization kinetics were slower for ELP-tendamistat and thioredoxin-ELP-tendamistat fusions, typically requiring 5 to 10 minutes versus only a few seconds for free ELP and thioredoxin-ELP.

Thioredoxin and tendamistat controls exhibited no change in absorbance with increasing temperature, indicating that the thermally-induced aggregation observed for the fusion proteins was due to the inverse transition of the ELP carrier. Typically, the inverse transition of the fusion proteins was also slightly broader than that of free ELP, and small upper and lower shoulders were observed in their turbidity profiles.

Motivated by the studies of Urry and colleagues, who observed a decrease in $T_t$ with increasing chain length,[22] the effect of ELP MW on the inverse transition of FPs was also investigated. The $T_t$ of a set of thioredoxin-FPs were determined as a function of the MW of the ELP carrier, which ranged from 12.6 to 71.0 kDa (FIG. 2b). The $T_t$'s of the higher MW fusion proteins approached the design target temperature of 40° C. (42° C. for the 71 kDa ELP), while the $T_t$'s for the lower MW fusions were significantly greater (e.g., 77° C. for the 12.6 kDa ELP).

In addition to ELP-specific variables that affect the $T_t$ (i.e., guest residue composition and MW), the $T_t$ can be further modulated for a given ELP by several extrinsic factors, such as the choice of solvent, ELP concentration, and ionic strength[3]. Controlling the ionic strength, in particular, allows the $T_t$ to be tuned over a 50° C. range (FIG. 2c), and thereby provides a convenient method to optimize the $T_t$ of a given ELP for a specific application. Manipulating the solution temperature and ionic strength also provides experimental flexibility in inducing the inverse transition for a specific ELP by several methods: (1) by increasing the solution temperature above the $T_t$ at a given ionic strength, (2) by increasing the ionic strength isothermally to reduce the $T_t$ below solution temperature, or (3) by simultaneously changing the solution temperature and ionic strength.

6.3 Effect of ELP Fusion on Activity of Target Protein

The specific activity of the thioredoxin/60-mer FP, determined by an insulin reduction assay, was identical to that of commercially-available *E. coli* thioredoxin (results not shown), indicating that below the $T_t$, the ELP tag had no effect on thioredoxin activity. For the ternary thioredoxin-ELP-tendamistat fusion, an α-amylase inhibition assay showed that the thioredoxin/90-mer ELP carrier reduced the α-amylase inhibition activity of tendamistat by 2-fold (results not shown). However, after thrombin cleavage and purification of tendamistat from the thioredoxin-ELP carrier, the activity of purified tendamistat was indistinguishable from recombinant tendamistat, which was independently purified by IMAC.

6.4 Effect of Thermal Cycling on Activity of Target Proteins

The application of inverse transition cycling for protein purification requires that the phase transition of the ELP does not denature the target protein. We therefore monitored aggregation, resolubilization, and functional activity upon thermally cycling the thioredoxin/60-mer ELP fusion in 1.5 M NaCl (FIG. 3). 1.5 M NaCl was added to the buffer simply to lower the $T_t$ (from 62° C. in water to 27° C.) so that the FP would undergo its inverse transition in each thermal cycle between the experimentally-convenient temperatures of 24 and 35° C. Before commencing thermal cycling, the solution temperature of 24° C. was below the $T_t$ of the thioredoxin-FP, and the protein solution exhibited no detectable turbidity. The thioredoxin activity of the fusion protein was initially assayed at this temperature to establish a baseline. Upon increasing the temperature to 35° C., the fusion protein aggregated, resulting in increased turbidity ($OD_{350}$~2.0). After lowering the temperature to 24° C., the solution cleared completely, indicating that the fusion protein had resolubilized. An aliquot was removed and assayed for thioredoxin activity, which was found to be identical to the initial value. This thermal cycling process was repeated twice. No change in activity was observed at 24° C. after each thermal cycle, which confirmed that the small temperature change and the resulting aggregation/resolubilization had no effect on protein stability and function. In addition, resolubilization and recovery of the aggregated fusion protein was quantitative and complete after lowering the temperature to 24° C.

6.5 Purification of Fusion Proteins by Inverse Transition Cycling

Six thioredoxin-FPs, where each fusion protein contained a C-terminal 30-, 60-, 90-, 120-, 150-, or 180-mer ELP tag, and the thioredoxin/90-mer ELP/tendamistat fusion protein were purified from cell lysate by inverse transition cycling, achieved by repeated centrifugation at conditions (i.e., NaCl concentration and temperature) alternating above and below the transition temperature. Typical SDS-PAGE results are shown in FIG. 4a for two rounds of inverse transition purification of thioredoxin/90-mer ELP (lanes 1–5) and for one round of purification of thioredoxin/90-mer ELP/tendamistat (lanes 7–9).

Before purification, the induced *E. coli* were harvested from culture media by centrifugation, resolubilized in a low salt buffer (typically PBS), and lysed by ultrasonic disruption. After high-speed centrifugation to remove insoluble matter, polyethylenimine was added to the lysate to precipitate DNA, yielding soluble lysate (lanes 1 and 7, FIG. 4a). Inverse transition cycling was then initiated by adding NaCl and/or increasing the solution temperature to induce the inverse transition of the FP, causing the solution to become turbid as a result of aggregation of the FP. The aggregated fusion protein was separated from solution by centrifugation at a temperature greater than the $T_t$, and a translucent pellet formed at the bottom of the centrifuge tube. The supernatant, containing contaminating *E. coli* proteins, was decanted and discarded (lanes 2 and 8). The pellet was redissolved in a low ionic strength buffer at a temperature below the $T_t$ of the ELP, and centrifuged at low temperature to remove any remaining insoluble matter (lanes 3 and 9). Although additional rounds of inverse transition cycling were undertaken (lanes 4 and 5), the level of contaminating proteins was below the detection limit of SDS-PAGE after a single round of inverse transition cycling.

FIG. 4b shows the thioredoxin specific activity at each stage of purification of the thioredoxin/ELP fusion, as well as the total protein as estimated by BCA assay. Approximately 20% of the total protein in the soluble lysate (1) was precipitated in the first round of inverse transition purification (3), and the remaining soluble protein was decanted and discarded (2). The low thioredoxin activity measured in the supernatant, a portion of which is contributed by native *E. coli* thioredoxin, confirmed that this fraction primarily contained contaminating host proteins. The thioredoxin specific activity of the resolubilized protein approached that of commercially-available thioredoxin (data not shown), which confirmed that one round of inverse transition cycling resulted in complete purification. A second round of purification resulted in no detectable increase in thioredoxin specific activity (data not shown). The total thioredoxin activity after several rounds of inverse transition purification was experimentally-indistinguishable from that of the cell lysate (1, 3, and 5), indicating negligble loss of target protein in the discarded supernatant. These results quantitatively confirmed the high purity and efficient recovery of the thioredoxin-FP, and further demonstrated that functional activity of thioredoxin is fully retained after undergoing several rounds of inverse transition cycling.

Protein yields for the thioredoxin fusion constructs were typically greater than 50 milligrams of purified fusion protein per liter culture. We found that the total gravimetric yield of fusion protein decreased with increasing ELP length, with the 30-mer (MW=12.6 kDa) averaging ~70 mg/L and the 180-mer (MW=71.0 kDa) averaging ~50 mg/L. Expression levels of soluble tendamistat were slightly larger for the ternary thioredoxin-ELP-tendamistat fusion (45 mg/L ternary fusion, or 7 mg/L tendamistat) compared to its fusion with thioredoxin only (10 mg/L thioredoxin-tendamistat fusion, 4 mg/L tendamistat).

6.6 Discussion

Two recombinant proteins, thioredoxin and tendamistat, fused to an environmentally-responsive ELP sequence, were expressed and a gentle, one-step separation of these fusion proteins from other soluble $E.\ coli$ proteins was achieved by exploiting the inverse transition of the ELP sequence. Thioredoxin and tendamistat were selected as target proteins because they exemplify two limiting scenarios of soluble protein expression: (1) the target protein over-expresses at high levels and is highly soluble (thioredoxin), and (2) the protein is expressed largely as insoluble inclusion bodies (tendamistat). However, proteins representative of this latter class must exhibit some level of expression as soluble protein to be purified by inverse transition cycling.

Thioredoxin is expressed as soluble protein at high levels in $E.\ coli$,[14,31] and is a therefore a good first test of whether the reversible, soluble-insoluble inverse transition of the ELP tag would be retained in a fusion protein. In contrast, tendamistat was selected as the other test protein because it is largely expressed as insoluble protein in inclusion bodies. Although fusion with thioredoxin is known to promote the soluble expression of target proteins,[14] only 5–10% of over-expressed thioredoxin-tendamistat fusion protein was recovered as soluble and functionally-active protein. There was initial concern that incorporation of a hydrophobic ELP sequence in a fusion protein that exhibits a pronounced tendency to form inclusion bodies might (1) exacerbate its irreversible aggregation in vivo during culture, and (2) cause irreversible aggregation in vitro during purification by inverse transition cycling. Contrariwise, however, neither problem was encountered with the ELP-tendamistat fusion protein.

Design of ELP Carrier. The polypeptide carrier used for thermally-induced, phase separation of the target recombinant protein was derived from pentapeptide repeats found in mammalian elastin.[2,3] Because the phase transition of ELPs is the fundamental basis of protein purification by inverse transition cycling, specifying the transition temperature is the primary objective in the design of an ELP carrier. Previous studies by Urry and colleagues have shown that the fourth residue (X) in the elastin pentapeptide sequence, VPGXG, can be altered without eliminating the formation of the β-turn, a structure key to the inverse transition.[15] These studies also showed that the $T_t$ is a function of the hydrophobicity of the guest residue. Therefore, by varying the identity of the guest residue(s) and their mole fraction(s), ELP copolymers can be synthesized that exhibit an inverse transition over a 0–100° C. range.[32] Based on these results, an amino acid sequence was selected to result in a predicted $T_t$ of ~40° C. in water, so that the ELP carrier would remain soluble in $E.\ coli$ during culture but could be aggregated by a small increase in temperature after cell lysis.

In addition to the amino acid sequence, it is known that $T_t$ also varies with ELP chain length.[33] The design therefore incorporated precise control of molecular weight by a gene oligomerization strategy so that a library of ELPs with systematically varied molecular weight could be synthesized. The $T_t$'s of the higher molecular weight ELPs approached the target temperature, with an experimentally-observed $T_t$ of 42° C. for the thioredoxin/180-mer fusion (at 25 µM in PBS). However, the $T_t$ increased dramatically with decreasing MW. In low ionic strength buffers, the $T_t$'s of the lower molecular weight ELPs are too high for protein purification, and would consequently require a high concentration of NaCl to decrease the $T_t$ to a useful temperature. ELP chain length is also important with respect to protein yields. In addition to the decreased total yield of expressed fusion protein observed with increasing ELP MW, the weight percent of target protein versus the ELP also decreases as the MW of the ELP carrier increases. Therefore, the design of our next generation ELP carriers for purification will maximize target protein expression by minimizing the ELP molecular weight, while retaining a target $T_t$ near 40° C. through the incorporation of a larger fraction of hydrophobic guest residues in the ELP sequence.

The thioredoxin-ELP fusion exhibited only a small increase in $T_t$ (1–2° C.) compared to free ELP, while the tendamistat fusion displayed a more dramatic 15° C. reduction in $T_t$. This shift was identical for both the ternary (thioredoxin-ELP-tendamistat) and binary (ELP-tendamistat) constructs, indicating that the $T_t$ shift is associated specifically with tendamistat. Based on these observations, it was hypothesize that the decreased $T_t$ was due to interactions between the ELP chain and solvent-exposed hydrophobic regions in tendamistat, whereas, for the highly soluble thioredoxin, these hydrophobic interactions were negligible. Although this shift in $T_t$ added complexity to the design of ELP carriers for inverse transition purification of proteins containing a significant fraction of exposed hydrophobic area, for highly soluble proteins only a small perturbation of $T_t$ relative to the free ELP is likely to be introduced upon fusion with an ELP tag.

6.7 Methods

6.7.1 Gene Synthesis

Standard molecular biology protocols were used for gene synthesis and oligomerization.[34] The synthetic gene for the 10 polypentapeptide ELP was constructed from four 5'-phosphorylated, PAGE-purified synthetic oligonucleotides (Integrated DNA Technologies, Inc.), ranging in size from 86 to 97 bases. The oligonucleotides were annealed to form double-stranded DNA spanning the ELP gene with EcoRI and HindIII compatible ends (FIG. 5a). The annealed oligonucleotides were then ligated, using T4 DNA ligase, into EcoRI/HindIII linearized and dephosphorylated pUC-19 (NEB, Inc.). Chemically competent $E.\ coli$ cells (XL1-Blue) were transformed with the ligation mixture, and incubated on ampicillin-containing agar plates. Colonies were initially screened by blue-white screening, and subsequently by colony PCR to verify the presence of an insert. The DNA sequence of a putative insert was verified by dye terminator DNA sequencing (ABI 370 DNA sequencer).

6.7.2 Gene Oligomerization

First, a 20-mer ELP gene was created by ligating a 10-mer gene into a vector containing the same 10-mer gene. The 20-mer gene was similarly combined with the original 10-mer gene to form a 30-mer gene. This combinatorial process was repeated to create a library of genes encoding ELPs ranging from 10 to 180 pentapeptides. For a typical oligomerization, the vector was linearized with PflMI and enzymatically dephosphorylated. The insert was doubly digested with PflMI and BglI, purified by agarose gel electrophoresis (Qiaex II Gel Extraction Kit, Qiagen Inc.), ligated into the linearized vector with T4 DNA ligase, and transformed into chemically competent E. coli cells. Transformants were screened by colony PCR, and further confirmed by DNA sequencing.

6.7.3 Fusion Protein Construction

For the thioredoxin fusions, pET-32b expression vector (Novagen Inc.) was modified to include an SfiI restriction site and a transcriptional stop codon downstream of the thioredoxin gene (FIG. 5b). For the ternary tendamistat fusion, a previously constructed pET-32a based plasmid containing a gene for a thioredoxin-tendamistat fusion was modified to contain an SfiI restriction site in two alternate locations, upstream or downstream of the thrombin recognition site (FIG. 5c). ELP gene segments, produced by digestion with PflMI and BglI, were then ligated into the SfiI site of each modified expression vector. Cloning was confirmed by colony PCR and DNA sequencing.

6.7.4 Protein Expression

The expression vectors were transformed into the expression strains BLR(DE3) (thioredoxin fusions) or BL21-trxB (DE3) (tendamistat fusion) (Novagen, Inc.). Shaker flasks with 2×YT media, supplemented with 100 μg/ml ampicillin, were inoculated with transformed cells, incubated at 37° C. with shaking (250 rpm), and induced at an $OD_{600}$ of 0.8 by the addition of isopropyl α-thiogalactopyranoside (IPTG) to a final concentration of 1 mM. The cultures were incubated an additional 3 hours, harvested by centrifugation at 4° C., resolubilized in low ionic strength buffer (~1/30 culture volume), and lysed by ultrasonic disruption at 4° C. The lysate was centrifuged at ~20,000×g at 4° C. for 15 minutes to remove insoluble matter. Nucleic acids were precipitated by the addition of polyethylenimine (0.5% final concentration), followed by centrifugation at ~20,000×g at 4° C. for 15 minutes. Soluble and insoluble fractions of the cell lysate were then characterized by sodium-dodecyl sulfate polyacrylamide gel electrophoresis (SDS-PAGE).[20]

6.7.5 Fusion Protein Purification

The thioredoxin fusions, which contained a $(His)_6$ tag, were purified by immobilized metal ion affinity chromatography (IMAC) using a nickel-chelating nitrilotriacetic derivatized resin (Novagen Inc.)[30] or, alternatively by inverse transition cycling. The tendamistat fusion was purified exclusively by inverse transition cycling. For purification by inverse transition cycling, FPs were aggregated by increasing the temperature of the cell lysate to ~45° C. and/or by adding NaCl to a concentration ~2 M. The aggregated fusion protein was separated from solution by centrifugation at 35–45° C. at 10–15,000×g for 15 minutes. The supernatant was decanted and discarded, and the pellet containing the fusion protein was resolubilized in cold, low ionic strength buffer. The resolubilized pellet was then centrifuged at 4° C. to remove any remaining insoluble matter.

6.7.6 Inverse Transition Temperature

The optical absorbance at 350 nm of ELP fusion solutions were monitored in the 4–80° C. range on a Cary 300 UV-visible spectrophotometer equipped with a multi-cell thermoelectric temperature controller. The $T_t$ was determined from the midpoint of the change in optical absorbance at 350 nm due to aggregation of FPs as a function of temperature at a heating or cooling rate of 1.5° C. $min^{-1}$.

6.7.7 Characterization of the Fusion Proteins

SDS-PAGE analysis used precast Mini-Protean 10–20% gradient gels (BioRad Inc.) with a discontinuous buffer system.[20] The concentration of the fusion proteins was determined spectrophotometrically using calculated extinction coefficients. Total protein concentrations were determined by BCA assay (Pierce).[35] Thioredoxin activity was determined by a calorimetric insulin reduction assay.[36] Tendamistat activity was determined by a calorimetric α-amylase inhibition assay (Sigma).

6.7.8 Other Data

The inventor has also synthesized ELP-GFP fusion proteins, where the ELP 90-mer and 180-mer were fused either N-terminal or C-terminal to green fluorescent protein (GFP) or its variant—blue fluorescent protein (BFP). All fusion polypeptides exhibited a reversible inverse transition as characterized by UV-vis spectrophotometric measurement of turbidity as a function of temperature, as well as temperature dependent fluorescence measurement. The inverse transition of the GFP-ELP and BFP-ELP fusions, was used to purify these fusion proteins to homogeneity by ITC, and was verified by SDS-PAGE and Coomassie staining.

6.8 Effect of Reduced ELP Molecular Weight on the Expression/Purification of Thioredoxin-ELP Fusion Protein

6.8.1 Gene Synthesis

Standard molecular biology protocols were used for synthesis and oligomerization of the ELP genes (Ausubel, et al.[32]). Monomer genes for two ELP sequences were utilized in this example. The first, ELP[$V_5A_2G_3$-10] encoding ten Val-Pro-Gly-Xaa-Gly repeats where Xaa was Val, Ala, and Gly in a 5:2:3 ratio, respectively, had been synthesized previously[37]. The second monomer, ELP[V-5] (Sequence ID No. 4), encoded five Val-Pro-Gly- al-Gly pentapeptide (i.e., Xaa was exclusively Val). The coding sequence for the ELP[V-5] monomer ene was: 5'-GTGGGTGT-TCCGGGCGTAGGTGTCCCAGGTGTGGGCGTA-CCGGGCGTTGGTGTTCCTG GTGTCGGCGTG-CCGGGC-3' (Sequence ID No. 5). The monomer genes were assembled from chemically synthesized, 5'-phosphorylated oligonucleotide (Integrated DNA Technologies, Coralville, Iowa), and ligated into a pUC19-based cloning vector. A detailed description of the monomer gene synthesis is presented elsewhere[38].

6.8.2 Gene Oligomerization

The monomer genes for both ELP sequences, ELP[$V_5A_2G_3$-10] and ELP[V-5], were seamlessly oligomerized by tandem repetition to encode libraries of increasing ELP molecular weight. A detailed description of the gene oligomerization, using a methodology termed "recursive directional ligation", is presented elsewhere[36]. Briefly, an ELP gene segment (the monomer gene initially and larger multiples of the monomer in later rounds) is excised by restriction digest from its vector, purified, and ligated into a second cloning vector containing the same or a different ELP gene segment, thereby concatenating the two gene segments.

This process can be repeated recursively, doubling the gene length with each round.

Different ELP constructs are distinguished here using the notation ELP[$X_iY_j$-n], where the bracketed capital letters are single letter amino acid codes and their corresponding subscripts designate the frequency of each guest residue in the repeat unit, and n describes the total length of the ELP in number of pentapeptides. The two ELP construct central to the present example are ELP[$V_5A_2G_3$-90](35.9 kDa) (Sequence ID No. 6) and ELP[V-20] (9.0 kDa) (Sequence ID No. 7).

6.8.3 Expression in E. coli

To produce the thioredoxin fusion proteins, genes encoding ELP[$V_5A_2G_3$-90] and ELP[V-20] were excised from their respective cloning vectors and separately ligated into a pET-32b expression vector (Novagen, Madison, Wis.), which had been previously modified to introduce a unique Sfi I site located 3' to the thioredoxin gene, a (His)$_6$ tag, and a thrombin protease cleavage site[37]. The modified pET32b vector encoding free thioredoxin with no ELP tag ("thioredoxin(His$_6$)") and the two expression vectors encoding each fusion protein ("thioredoxin-ELP[$V_5A_2G_3$-90]" and "thioredoxin-ELP[V-20]") were transformed into the BLR(DE3) E. coli strain (Novagen).

For quantitative comparison of the protein expression levels and purification yields, the three constructs were each expressed and purified in parallel. For each sample (four samples each of thioredoxin(His$_6$), thioredoxin-ELP[V-20], and thioredoxin-ELP[$V_5A_2G_3$-90]), a 2 ml starter culture (CircleGrow media, Qbiogene, Carlsbad, Calif., supplemented with 100 µg/ml ampicillin) was inoculated with a stab taken from a single colony on a freshly streaked agar plate, and incubated overnight at 37° C. with shaking at 300 rpm. To remove β-lactamase from the media, the cells were then pelleted from 500 µl of the confluent overnight culture by centrifugation (2000×g, 4° C., 15 min), resuspended in fresh media wash, and repelleted. After a second resuspension in fresh media, the cells were used to inoculate 50 ml expression cultures in 250 ml flasks (CircleGrow media with 100 µg/ml ampicillin).

The culture flasks were incubated at 37° C. with shaking at 300 rpm. Growth was monitored by the optical density at 600 nm, and protein expression was induced at OD$_{600}$=1.0 by the addition of isopropyl β-thiogalactopyranoside (IPTG) to a final concentration of 1 mM. After a further 3 hours of culture, the cells were harvested from 40 ml by centrifugation (2,000×g, 4° C., 15 min), resuspended in 2 ml of IMAC binding buffer (5 mM imidazole, 500 mM NaCl, 20 mM Trix-HCl, pH 7.9) for thioredoxin(His$_6$) or PBS (137 mM NaCl, 2.7 mM KCl, 4.2 mM Na$_2$HPO$_4$, 1.4 mM KH$_2$PO$_4$, pH 7.3) for thioredoxin-ELP[V-20] and thioredoxin-ELP [$V_5A_2G_3$-90], and stored frozen at −20° C. until purified. The culture density at harvest was measured by OD$_{600}$, after 1:10 dilution in fresh buffer. The amount of plasmid DNA at harvest was quantified by UV-visible spectrophotometry following plasmid isolation (plasmid miniprep spin kit, Qiagen, Valencia, Calif.).

6.8.4 Thioredoxin (His$_6$) Purification by Immobilized Metal Affinity Chromatography (IMAC)

As a control for ITC purification of the thioredoxin-ELP fusion proteins, free thioredoxin was purified using standard IMAC protocols[39]. Briefly, the thawed cells were transferred to iced 15 ml centrifuge tubes and lysed by ultrasonic disruption (Fisher Scientific 550 Sonic Dismembrator using a microtip). After transferring to 1.5 ml micro centrifuge tubes, the E. coli lysate was centrifuged (16,000×g, 4° C., 30 min) to remove the insoluble cellular debris. 1 ml of the soluble cell lysate was loaded by gravity flow onto a column packed a 1 ml bed of nitrilotriacetic acid resin that had been charged with 5 ml of 50 mM NiSO$_4$.

After the column was washed with 15 ml of IMAC binding buffer, thioredoxin(His$_6$) was eluted in 6 ml of IMAC binding buffer supplemented with 250 mM imidazole. Imidazole was removed from the eluent by dialysis against a low salt buffer (25 mM NaCl, 20 mM Tris-HCl, pH 7.4) overnight using a 3,500 MWCO membrane. The IMAC purification was monitored by SDS-PAGE using precast 10–20% gradient gels (BioRad Inc., Hercules, Calif.) with a discontinuous buffer system[20].

The yield of the purified thioredoxin(His$_6$) was determined by spectrophotometry, using a molar extinction coefficient of thioredoxin modified to include the absorption of the single Trp residue present in the C-terminal tag ($\epsilon_{280}$= 19870 M$^{-1}$ cm$^{-1}$ for thioredoxin(His$_6$) and all thioredoxin-ELP fusion proteins, independent of ELP molecular weight[31].

6.8.5 Fusion Protein Purification by ITC

In a typical purification by ITC, the thawed cells were transferred to iced 15 ml centrifuge tubes and lysed by ultrasonic disruption (Fisher Scientific 550 Sonic Dismembrator with a microtip). After transferring to 1.5 ml micro centrifuge tubes, the E. coli lysate was centrifuged at 4° C. for 30 min to remove the insoluble cellular debris. (All centrifugation steps during purification by ITC were performed at 16,000×g in Eppendorf 5415C microcentrifuges.)

Polyethylenimine was added (to 0.5% w/v) to the decanted supernatant of the cell lysate to precipitate nucleic acids, which were removed by an additional 20 min centrifugation at 4° C. The supernatant was retained, and the ELP phase transition was induced by increasing the NaCl concentration by 1.3 M. The aggregated fusion protein was separated from solution by centrifugation at 33° C. for 5 min, which resulted in the formation of translucent pellet at the bottom of the tube.

The supernatant was decanted and discarded, and the pellet containing the fusion protein was redissolved in an equal volume of PBS at 4° C. Any remaining insoluble matter was removed by a final centrifugation step at 4° C. for 15 min, and the supernatant containing the purified fusion protein was retained. The progression of fusion protein purification was monitored by SDS-PAGE, and the protein concentrations were determined by spectrophotometry, as described above for IMAC purification.

Thioredoxin was liberated from its ELP fusion partner using thrombin protease (Novagen), which cleaved the fusion protein at a recognition site located between thioredoxin and the ELP tag[37]. The thrombin proteolysis reaction was allowed to proceed overnight at room temperature in PBS using ~10 units of thrombin per µmol of fusion protein, which was typically at a concentration of ~100 µM. Free ELP was then separated from the cleaved thioredoxin by another round of ITC, this time retaining the supernatant that contained the product thioredoxin.

6.8.6 Characterization of the Phase Transition

The temperature-dependent aggregation behaviors of the thioredoxin-ELP fusion proteins were characterized by measuring the optical density at 350 nm as a function of temperature. Fusion proteins at concentrations typical of those found in the *E. coli* lysate during protein purification (160 μM for thioredoxin-ELP[V-20] and 40 μM for thioredoxin-ELP[$V_5A_2G_3$-90]) were heat or cooled at a constant rate of 1° C. min$^{-1}$ in a Cary Bio-300 UV-visible spectrophotometer (Varian Instruments, Walnut Creek, Calif.), which was equipped with a thermoelectric temperature-controlled multicell holder. The experiments were performed in PBS variously supplemented with additional NaCl. The ELP $T_t$ was defined as the temperature at which the optical density reached 5% of the maximum optical density at 350 nm.

6.8.7 Particle Size Measurement

Dynamic light scattering (DLS) was used to monitor the particle size distribution of the thioredoxin-ELP fusion proteins as a function of temperature and NaCl concentration. Samples were prepared to reflect the protein and solvent compositions used in the turbidity measurements described above, and were centrifuged at 4° C. and 16,000×g for 10 minutes to remove air bubbles and insoluble debris. Prior to particle size measurement, samples were filtered through a 20 nm Whatman Anodisc filter at a temperature below the $T_t$.

Autocorrelation functions were collected using a DynaPro-LSR dynamic light scattering instrument (Protein Solutions, Charlottesville, Va.) equipped with a Peltier temperature control unit. Analysis was performed using Protein Solutions' Dynamics software version 5.26.37 using its regularization analysis for spherical particles. Light scattering data were collected at regular temperature intervals (either 1 or 2° C.) as solutions were heated from 20° to 60° C. Data were collected at each temperature by ramping the cell up to the temperature of interest, allowing the sample temperature equilibrate for at least 1 minute, and collecting 10 measurements, each with a 5 second collection time.

6.8.8 Characterization of Phase Transition by Turbidimetry

The inverse transition of each thioredoxin-ELP fusion protein in solution was characterized by monitoring the optical density at 350 nm as a function of temperature. Because different NaCl solutions are routinely used during ITC purification to depress the $T_t$ or isothermally trigger the inverse transition, turbidity profiles were obtained for 40 μM thioredoxin-ELP[$V_5A_2G_3$-90] and 160 μM thioredoxin-ELP [V-20] in PBS and in PBS with an additional 1M, 2M, and 3M NaCl (FIG. 13).

FIG. 13 is a graph of optical density at 350 nm as a function of temperature for solutions of the thioredoxin-ELP fusion proteins. The turbidity profiles were obtained for thioredoxin-ELP[V-20] (solid lines) and thioredoxin-ELP [$V_5A_2G_3$-90] (dashed lines) in PBS, and in PBS supplemented with 1, 2, and 3 M NaCl, while heating at a rate of 1° C. min$^{-1}$. The concentration of thioredoxin-ELP [$V_5A_2G_3$-90] was 40 μM in each of the four PBS solutions, and that of thioredoxin-ELP[V-20] was 160 μM, which matched the typical concentration of each protein in the soluble cell lysate during ITC purification. All solutions showed a rapid rise in turbidity as they were heated through the $T_t$, but with continued heating beyond the $T_t$, the thioredoxin-ELP[V-20] solutions eventually became less turbid while the thioredoxin-ELP[$V_5A_2G_3$-90] solutions remained consistently turbid. All solutions of thioredoxin-ELP[$V_5A_2G_3$-90] cleared fully upon cooling the solution to below the $T_t$. However, solutions of ELP[V-20] cleared reversibly only if the solutions were not heated to above ~55° C., suggesting thermal denaturation of the thioredoxin fusion protein occurred above this temperature. For clarity, only the heating profiles are shown.

The protein concentrations shown in FIG. 13 were chosen because they are typical of the concentrations obtained for each fusion protein in the soluble fraction of *E. coli* lysate, the stage at which the ELP inverse transition is first induced during ITC purification. Turbidity profiles obtained directly in the *E. coli* soluble cell lysate, supplemented with 1 and 2 M NaCl, were indistinguishable from the corresponding profiles in FIG. 13 (data not shown). (Turbidity profiles were not routinely obtained in *E. coli* lysate because of the potential for turbidity arising from thermal denaturation of *E. coli* proteins, which could not be differentiated from turbidity arising from aggregation of the ELP fusion protein.) Turbidity profiles were also obtained for each fusion protein in PBS with 1.3 M salt (FIG. 14), which matches the conditions used for the ITC purification described below.

FIG. 14 is a graph showing the heating and cooling turbidity profiles for the solution conditions used in ITC purification, for solutions of thioredoxin-ELP[V-20] (solid lines) and thioredoxin-ELP[$V_5A_2G_3$-90] (dashed lines) at lysate protein concentrations in PBS with 1.3 M NaCl, corresponding to ITC conditions used for the quantitative comparison of expression and purification (FIGS. 25 and 26). These conditions were chosen so that the maximum turbidity of the thioredoxin-ELP[V-20] solution occurred at the centrifugation temperature of 33° C. The solutions were heated and cooled at 1° C. min$^{-1}$. The slight path differences between the heating and cooling curves were primarily due to slow settling of the aggregates over time at temperatures above $T_t$, and to the slower kinetics of disaggregation versus aggregation as the solutions are cooled to below $T_t$.

The thermally induced aggregation behavior of thioredoxin-ELP[$V_5A_2G_3$-90] was similar to that of free ELPs. All four salt concentrations, as the temperature of the thioredoxin-ELP[$V_5A_2G_3$-90] solutions was increased, remain clear until they reach the ELP $T_t$, at which point the turbidity sharply increased. This occurred at 51, 31, 15, and 4° C. in PBS with 0, 1, 2, and 3 M added NaCl, respectively. A free thioredoxin control solution exhibited no change in turbidity with increasing temperature over this temperature range, indicating that the thermally induced aggregation observed was due to the inverse transition of the ELP tag (results not shown). As these solutions were heated further beyond the $T_t$, the turbidity level remained essentially constant, and was only slightly reduced by settling of the aggregates over time. Upon cooling to below the $T_t$, the aggregates resolubilize and the optical density returned to zero, showing that the inverse transition of the ELP [$V_5A_2G_3$-90] fusion protein was completely reversible (for clarity, cooling traces are not shown in FIG. 13; however, an example of reversibility upon cooling is shown in FIG. 14). While increasing the NaCl concentration markedly decreases the $T_t$, salt has no measurable effect on the maximum optical density, on the general shape of the turbidity profiles, or on the reversibility of the aggregation.

Figure 3:
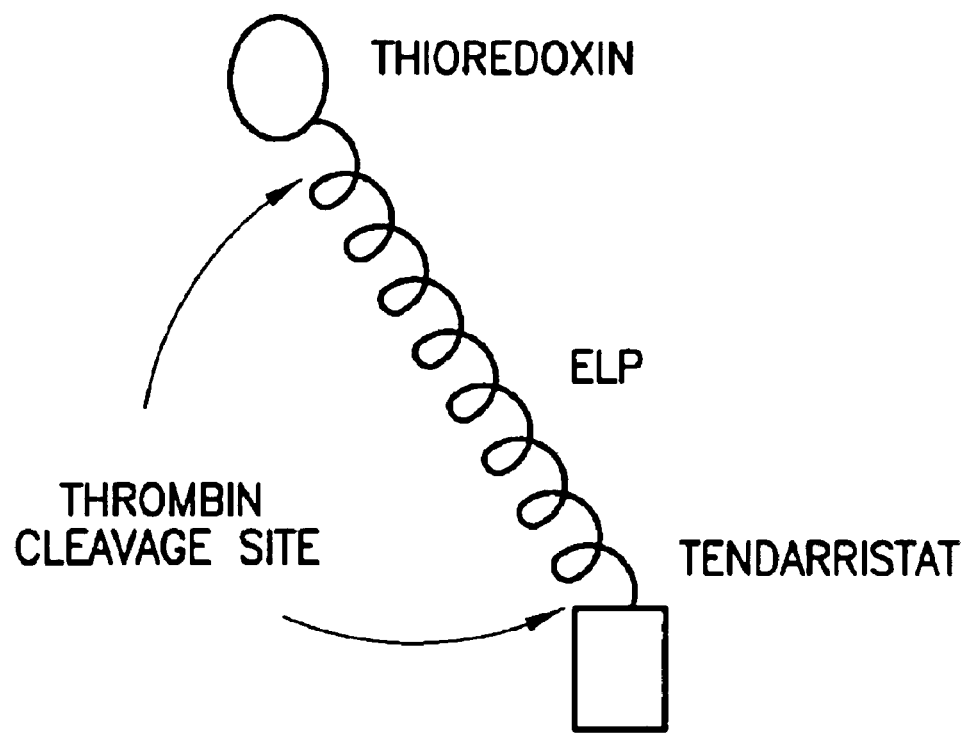
FIG. 3 is a schematic representation of a thioredoxin-ELP-tendamistat fusion protein showing the location of thrombin cleavage sites, one being between thioredoxin and the ELP, and the other being between the ELP and tendamistat.

In contrast, the phase transition behavior of thioredoxin-ELP[V-20] was considerably more complex than for the thioredoxin-ELP[$V_5A_2G_3$-90] fusion protein and free ELPs. Although the initial rapid rise in turbidity at the $T_t$ (33, 17, and 4° C. in PBS supplemented with 1, 2, and 3 M NaCl, respectively) was similar to the other ELP constructs, the maximum turbidity observed with each of the thioredoxin-ELP[V-20] solutions increased with increasing salt concentration. Furthermore, increases in temperature beyond the $T_t$ eventually resulted in a significant decrease in turbidity. This decrease was reversible; if the solution was cooled after heating to the point of decreased turbidity, the turbidity again increased (as illustrated in FIG. 3). Because the clearing phenomenon is a reversible function of temperature, it was concluded that a second, thermodynamically driven molecular rearrangement occurs with increasing temperature after the initial ELP aggregation event at $T_t$.

Another unique feature of the thioredoxin-ELP[V-20] turbidity profiles was a second increase in turbidity beginning at ~55° C. (FIG. 13), which may have been due to aggregation arising from the irreversible thermal denaturation of thioredoxin. Samples heated to less than 55° C. reversibly cleared upon cooling to below the $T_t$ (e.g., as in FIG. 14), whereas samples that are heated to above 55° C., for salt concentrations of 1 M and greater, remained turbid even upon cooling to below the $T_t$ (not shown). This phenomenon appeared to be unique to the thioredoxin-ELP [V-20] fusion protein, as solutions of free thioredoxin and of its fusion proteins to larger ELPs were stable to much higher temperatures (results not shown). No inverse transition was observed for thioredoxin-ELP[V-20] in PBS below 60° C., however, with added salt the $T_t$ was depressed so that it occured below the denaturation temperature in the PBS+1, 2, and 3 M NaCl solutions.

6.8.9 Temperature-Controlled Dynamic Light Scattering

The sizes of the fusion protein particles were measured using DLS as a function of temperature. FIGS. 15–20 show the effect of temperature and salt on the particle size distribution (radius of hydration, $R_h$) of 40 μM thioredoxin-ELP[$V_5A_2G_3$-90] in PBS (FIGS. 15 and 16), PBS+1 NaCl (FIGS. 17 and 18), and PBS+2 M NaCl (FIGS. 19 and 20). FIGS. 15, 17 and 19 show the effect of temperature on particle sizes of monomers (diamonds) and aggregates (squares). Analysis artifacts (stars) and network contributions (triangles), which may result from the coordinated slow movements of a network of smaller particles, are also shown (see text for discussion). FIGS. 16, 18 and 20 show the percentage of the scattered intensity attributed to each type of particle as a function of temperature. The appearance of the large aggregates closely coincided with the rise in turbidity observed in FIG. 13.

The sizes of thioredoxin-ELP[$V_5A_2G_3$-90] particles in PBS (FIG. 15), PBS with 1M added NaCl (FIG. 17), and PBS with 2M added NaCl (FIG. 19) indicate that the sharp increase in turbidity at the $T_t$ resulted from the conversion of monomers with hydrodynamic radii ($R_h$) of 5.9±3.9 nm to aggregates with $R_h$ of 180±62 nm. These aggregates grew with temperature until reaching a stable $R_h$ of 2.2±3.8 μm approximately 6° C. above the onset of the transition. Although the $T_t$ was depressed by the addition of NaCl, the sizes of both monomers and fully formed aggregates were not significantly affected by either the salt concentration or the temperature (outside the range immediately adjacent to the $T_t$), providing a rationale for the steady-state turbidity above the inverse $T_t$. The temperature at the onset of large aggregate formation closely matched the $T_t$ determined by the turbidity measurements for corresponding solution conditions.

The corresponding quantitative breakdown of scattered intensity attributed to each type of particle is also shown for each of the salt concentrations investigated (FIG. 16, 18 and 20). When two or more phases coexist over a given temperature range, these data show shifts in the relative particle populations. It should be noted that the intensity attributed to a particular population was not linearly correlated with the mass of that population, and that calculating the relative masses of multiple particles was complicated by changes in packing density that would likely accompany the inverse phase transition. Without a more detailed understanding of how temperature affects the packing density of ELPs and ELP fusion proteins, it was not possible to make a reasonable estimate for the mass attributed to each type of particle. Given these quantitative limitations, this data nonetheless shows that at the $T_t$ the amount of scattered light attributed to the aggregate dramatically increased at the expense of the monomer.

FIGS. 15–20 also shows the occasional presence of both an unidentified small particle (with apparent $R_h$=17+31 nm, albeit highly variable) and an extremely large aggregate (with apparent $R_h$=74±55 μm) coexisting with the 2 μm aggregates. It is unlikely that the small particle is a true component of the aggregate suspension; rather, its presence reflects an artifact in the regularization algorithm resulting from noise in the autocorrelation function. Assignment as an analysis artifact is supported by the small particle's highly variable size and by its inconsistent presence at temperatures above the transition. Likewise, because its apparent size is much larger than can be discerned by the DLS instrument, it is also unlikely that the extremely large aggregate predicted from the data analysis represented a true species in suspension. Rather, the scattering attributed to this species may result from the coordinated slow movements of a network of smaller particles.

In contrast to thioredoxin-ELP[$V_5A_2G_3$-90], the smaller thioredoxin-ELP[V-20] fusion protein showed a more complicated temperature-dependent particle size distribution, which was consistent with its more complex turbidity profile.

FIGS. 21–24 show the effect of temperature on the particle size distribution of ELP[V-20] in PBS+1 M NaCl (FIGS. 21 and 22) and PBS+2 M NaCl (FIGS. 23 and 24). FIGS. 21 and 23 show the effect of temperature on particle sizes of monomers (diamonds), 12 nm particles (circles), and larger aggregates (squares). Network contributions are also shown (triangles). FIGS. 22 and 24 show the percentage of the scattered intensity attributed to each type of particle as a function of temperature. The clearing in turbidity when the temperature is increased beyond $T_t$, as seen in FIG. 13, coincided with the shifting of mass from large aggregates to a new, smaller particle ($R_h$=12 nm).

Specifically, FIGS. 21–24 show the effects of salt and temperature on the distribution of the particle $R_h$ and the corresponding contribution of each particle population to scattered intensity of 160 μM thioredoxin-ELP[V-20] in PBS with 1M and 2M added NaCl. For thioredoxin-ELP[V-20] with 1M added salt (FIG. 21) monomers with $R_h$ of 5.9±5.1 nm were converted to aggregates with $R_h$ of 140±79 nm at 30° C., corresponding in FIG. 13 to a small shoulder that precedes the rapid increase in turbidity at $T_t$. Above 30° C., aggregates grew with increasing temperature (up to $R_h$=1.5±0.98 μm at 40° C.), which was consistent with the rapid increase in turbidity observed starting at 33° C. in FIG. 13. Similar to the aggregation behavior of the large fusion protein, at temperatures greater than 40° C. thioredoxin-ELP [V-20] in PBS with 1M added NaCl showed the presence of very large aggregates (apparent $R_h$=64±67 μm) that may reflect the coordinated slow movements of a network of smaller particles.

However, unlike the larger fusion protein, thioredoxin-ELP[V-20] also showed the consistent presence of a previously unobserved small particle at temperatures above 40° C. This particle had a $R_h$ of 12±4.9 nm, which was roughly twice that of the monomer. Yet, relative to its mean $R_h$, its variability was only one half that of the monomer. The size, consistency, and continuous presence of this particle above 40° C. indicated that it was neither an analysis artifact resulting from noise in the autocorrelation function nor was it resolvated monomer. The 12 nm particle appeared to form at the expense of mass in the aggregates initially present above $T_t$, as evidenced by the reduction in size and scattering intensity of the larger aggregates ($R_h$=200±210 nm) when the 12 nm particles were present.

A similar 12 nm particle was observed when the NaCl concentration was increased to 2 M (FIGS. 23 and 24). At this NaCl concentration, the $T_t$ was lowered to 17° C. as determined by the turbidity measurements. This temperature range was limited at lower temperatures by the condensation of water vapor on the sample cuvette. Therefore, between 20° C. and 30° C., the thioredoxin-ELP[V-20] had already transitioned into stable aggregates with average $R_h$ of 2.4±1.7 μm. As the samples was heated beyond ~36° C., the $R_h$ of the aggregates gradually decreased in size to 230±170 nm and 12 nm particles ($R_h$=12±4.7 nm) appeared. The percentage of scattered light attributable to the 12 nm particles also gradually increased at the expense of the shrinking larger aggregates.

6.8.10 Effect of ELP Size on Expression and Purification by ITC

Thioredoxin-ELP[V-20] and thioredoxin-ELP[$V_5A_2G_3$-90] were each purified by ITC from the soluble fraction of lysed *E. coli* cultures[35], and thioredoxin(His$_6$) was purified by IMAC as a control having no ELP tag. Representative SDS-PAGE results for the purification of each protein are shown in FIG. 25 (showing only the first round of ITC for the two ELP fusion proteins).

Lane A shows a molecular weight marker, labeled in kDa. Lanes B–D show IMAC purification of free thioredoxin (His$_6$), and Lanes E–H and I–L show ITC purification of thioredoxin-ELP[V-20] and thioredoxin-ELP[$V_5A_2G_3$-90], respectively. Lanes B, E, and I are the soluble cell lysate. Lanes C and D are the IMAC column flow-through and elution product, respectively. For ITC purification, lanes F and J are the supernatant after inverse transition and centrifugation; lanes G and K are the pellet containing the target protein, after redissolving in PBS; and lanes H and L are the purified target protein thioredoxin, after cleavage with thrombin and separation from its ELP tag by a second round of ITC. The inverse transition was induced by the addition of 1.3 M NaCl, and the centrifugation was carried out at 33° C. The smaller ELP[V-20] tag was successfully used to purify the fusion protein by ITC to homogeneity, with a yield and purity similar to that of the free thioredoxin purified by a conventional affinity chromatography method.

Note that the ELP tag was not stained by Coomassie[40], and therefore only the thioredoxin portion of the fusion protein was visible in the stained gels. Qualitative comparison of the expression levels in the soluble cell lysate for thioredoxin-ELP[V-20] (lane E) and thioredoxin-ELP [$V_5A_2G_3$-90] (lane I) clearly showed that truncating the size of the ELP tag from 36 kDa to 9 kDa greatly enhanced the expression yield of the thioredoxin. Furthermore, FIG. 25 shows that thioredoxin-ELP[V-20] was expressed to a level qualitatively comparable to that of free thioredoxin (lane B). SDS-PAGE analysis also showed that there was no detectable loss to the insoluble fraction of the cell lysate for any the target proteins (results not shown).

For the ITC purifications, the ELP phase transition was triggered by adding 1.3 M additional NaCl and increasing the solution temperature to above ~33° C. The cell lysates became turbid as a result of aggregation of the thioredoxin-ELP fusion proteins, which were then separated from solution by centrifugation at ~33° C. to form a translucent pellet at the bottom of the centrifuge tube. SDS-PAGE showed that most contaminating *E. coli* proteins were retained in the decanted supernatant (FIG. 25, lanes F and J). The pellets were dissolved in PBS at ~4° C., and centrifuged at low temperature (~12° C.) to remove any remaining insoluble matter. The supernatants containing purified thioredoxin-ELP fusion proteins were retained (FIG. 25, lanes G and K). Finally, purified, free thioredoxin was obtained after cleavage of each fusion protein by thrombin at the encoded recognition site located between thioredoxin and the ELP tag, followed by a second round of ITC to remove the ELP tag from solution (FIG. 25, lanes H and L). Here, thrombin was retained with the target thioredoxin in the supernatant (although it was below the detection limit of Coomassie staining), however a thrombin-ELP fusion could be developed that would be removed after cleavage along with the free ELP.

These SDS-PAGE results clearly showed that thioredoxin can be purified by ITC to homogeneity, as ascertained by Coomassie staining, using the shorter, 9 kDa ELP[V-20]. However, differences were observed in the purification efficiency of the two ELP fusion proteins under these conditions, as qualitatively ascertained by SDS-PAGE. Lanes I through K show that recovery of thioredoxin-ELP [$V_5A_2G_3$-90] by ITC from the soluble cell lysate was essentially complete, whereas lanes E though G show that a small but significant fraction of thioredoxin-ELP[V-20] remained in the discarded supernatant (lane G). The level of purity obtained by ITC with the ELP[V-20] tag was qualitatively as good or better than that obtained by IMAC purification of the free thioredoxin, although with IMAC purification there was no detectable loss of the target protein in the column flow-through (lane C).

Using UV-visible spectrophotometry, the yield of each protein recovered by ITC or IMAC purification was quantified (FIG. 26). Although these data described the amount of protein recovered after purification, the SDS-PAGE results in FIG. 25 suggested that this quantity was nearly equal to expression yield in the soluble lysate. For this analysis, four cultures were grown in parallel under identical conditions for each of the three protein constructs. For experimental convenience, these data were obtained for 50 ml cultures, and extrapolated to yield per liter of culture. Purification of separate 1 liter cultures confirmed that the actual yields closely matched the extrapolated values (data not shown).

FIG. 26 is a graph of purified protein yield. The total yields of the thioredoxin(His$_6$), thioredoxin-ELP[V-20], and thioredoxin-ELP[$V_5A_2G_3$-90] from the 50 ml test cultures are shown, extrapolated to milligrams per liter of culture (mean±SD, n=4). The separate contributions of the ELP tag and thioredoxin to the yield, as calculated using their respective mass fractions of the fusion protein, are also shown for comparison. With all other experimental conditions identical, reducing the ELP tag from 36 (thioredoxin-ELP [$V_sA_2G_3$-90]) to 9 kDa (thioredoxin-ELP[V-20]) resulted in a near four-fold increase in the yield of the target thioredoxin.

The data in FIG. 26 show that decreasing the molecular weight of the ELP tag can dramatically increase the yield of thioredoxin. Under experimentally identical conditions of *E. coli* culture, decreasing the ELP tag size from 36 kDa in thioredoxin-ELP[V$_5$A$_2$G$_3$-90] to 9 kDa in thioredoxin-ELP [V-20] increased the yield of fusion protein by 70% (82±12 mg/L versus 137±21 mg/L, respectively; P<0.005, unpaired t test). Furthermore, since truncating the size of the ELP tag reduced its mass fraction in the fusion protein, the target protein thioredoxin (i.e., if separated from the fusion protein at the thrombin cleavage site) constituted a larger fraction of the mass in the fusion protein yield. Thus, the yield of thioredoxin was 365% greater using the smaller tag (23±3.3 mg/L versus 83±12 mg/L for the larger and smaller tags, respectively; P<0.0001). This yield of thioredoxin obtained by ITC using the 9 kDa tag was statistically indistinguishable from that obtained for thioredoxin expressed without an ELP tag and purified using IMAC (93±13 mg/L; P>0.25).

These results corroborated the SDS-PAGE results since the relative yields of thioredoxin (FIG. 26) correlated with the expression levels observed in the cell lysate (FIG. 25). The yield of the ELP tag was the same for both fusion proteins (59±8.6 mg/L for thioredoxin-ELP[V$_5$A$_2$G$_3$-90] and 54±8.1 mg/L for thioredoxin-ELP[V-20]; P>0.4). This was consistent with previous observations that the gravimetric yield of the ELP tag in thioredoxin fusion proteins was essentially constant with respect to ELP molecular weight within the ELP[V$_5$A$_2$G$_3$-90]] family of polypeptides ranging from 24 to 72 kDa.

To demonstrate the relationship between purification efficiency and ITC solution conditions, we repeated ITC purification of the thioredoxin-ELP[V-20] fusion protein using different combinations of salt concentration and centrifugation temperature (FIG. 27).

FIG. 27 shows SDS-PAGE analysis of the effect of NaCl concentration and centrifugation temperature on purification of thioredoxin-ELP[V-20] by ITC: SL=soluble cell lysate; S=supernatant after inverse transition of fusion protein and centrifugation to remove aggregated target protein; and P=redissolved pellet containing the purified fusion protein, after dissolution in PBS. The molar NaCl concentration and centrifugation temperature for each purification is noted at top. Although a high level of purity was achieved in each case, selection of an appropriate NaCl concentration and centrifugation temperature is critical to achieve complete purification efficiency.

When PBS with 1 M NaCl combined with centrifugation at 49° C. was used for ITC purification, the majority of the target fusion protein was lost in the discarded supernatant (FIG. 27, left panel). When PBS plus 2 M NaCl and a centrifugation temperature of 33° C. was used (FIG. 27, center panel), more than half of the target protein was captured by centrifugation. Finally, using PBS with 3 M NaCl and centrifugation at 12° C. (FIG. 27, right panel), the vast majority of the target protein was successfully purified. Although the target protein was purified to homogeneity in each of these examples, these results showed that selection of salt concentration and temperature was an important factor influencing the efficiency of ITC purification.

6.8.11 Results

The objective of the foregoing example was to produce an ELP tag for ITC purification that was reduced in size relative to those previously reported[35], and to characterize the effect of this reduction on expression levels and on purification efficiency. In the previously reported effort, a first generation of ELP purification tags was developed based on a ELP [V$_5$A$_2$G$_3$-10] monomer sequence. This sequence was recursively oligomerized to create a library of synthetic genes encoding ELPs with molecular weights ranging from 4 kDa (ELP[V$_5$A$_2$G$_3$-10]) to 71 kDa (ELP[V$_5$A$_2$G$_3$-180]). This particular guest residue composition was selected based on previous studies of Urry et al., and ELPs with this composition were predicted to exhibit a T$_t$ of ~40° C. for molecular weights of ~100 kDa in water[2,3,29]. A 40° C. T$_t$ was targeted so that the fusion proteins would remain soluble during culture at 37° C., but could be induced to reversibly aggregate through the ELP phase transition by a modest increase in salt concentration or solution temperature.

Although the T$_t$'s of the higher molecular weight constructs approached 40° C. (T$_t$=42° C. for the thioredoxin-ELP[V$_5$A$_2$G$_3$-180], with MW$_{ELP}$=71 kDa, in PBS at 25 $\mu$M), the T$_t$ of the thioredoxin-ELP[V$_5$A$_2$G$_3$] fusion proteins increased dramatically with decreasing molecular weight (T$_t$=77° C. for thioredoxin-ELP[V$_5$A$_2$G$_3$-30], with MW$_{ELP}$=13 kDa, under the same conditions)[35]. The high T$_t$'s of the lower molecular weight ELPs required the addition of a very high concentration of NaCl (>3 M) to reduce their T$_t$ to a useful temperature (e.g., 20–40° C.), which precluded their general use for purification by ITC because of the potential for salt-induced denaturation of target proteins. Although the larger ELP[V$_5$A$_2$G$_3$] polypeptides were successfully used to purify thioredoxin and second model target protein, tendamistat, we observed that the yield of the fusion protein was significantly decreased as the ELP[V$_5$A$_2$G$_3$] chain length was increased[35].

These observations motivated the redesign of the ELP expression tag in the above experiment to reduce the size of the ELP expression tag while also depressing its T$_t$, so that lower molecular weight ELP tags would exhibit a T$_t$ near 40° C. at more moderate NaCl concentrations. The second monomer gene, which was newly synthesized for this study, encoded a five pentamer ELP sequence where the fourth guest residue was exclusively Val (ELP[V-5]). Because the Val present in ELP[V] was more hydrophobic than the Ala and Gly present in ELP[V$_5$A$_2$G$_3$], thioredoxin-ELP[V] fusion proteins were predicted to have a T$_t$ of 40° C. at smaller ELP molecular weights than for thioredoxin-ELP [V$_5$A$_2$G$_3$] fusions[28,35].

The ELP[V-20] sequence (four tandem repeats of the ELP[V-5] gene) was selected from a library of ELP[V-5] oligomers for further characterization at a ITC purification tag due to the empirical observation of its T$_t$ near 40° C. at lysate protein concentration with moderate (1 M) NaCl. In the present example, the thioredoxin-ELP[V-20] construct (MW$_{ELP}$=9 kDa) was compared to the previously described thioredoxin-ELP[VsA$_2$G$_3$-90] construct (MW$_{ELP}$=36 kDa) because the two fusion proteins had very similar T$_t$'s in lysate conditions for varying NaCl concentrations, as can be seen in FIG. 13. That is, they are thermal analogs from each of the two libraries that meet the above-described desired T$_t$ characteristics for ITC purification tags.

Although previous observations suggested that decreasing the size of the ELP was likely to enhance the overall expression level of the fusion protein, it was not obvious, a priori, whether the decreased size of the tag would adversely affect purification of ELP fusion proteins by ITC. Therefore, in addition to its effect on the expression level of the target protein, the effect of the ELP tag length on the purification efficiency (i.e., degree of recovery) and on the purity of the target protein after ITC purification was explored.

The SDS-PAGE and spectrophotometry results (FIGS. 25–27) show that decreasing the ELP molecular weight from 36 kDa to 9 kDa enhanced expression of the fusion protein by nearly four-fold, and did not adversely affect the purity of the final protein under any of the solution conditions (i.e., NaCl concentration and temperature) used to induce the inverse transition. The level of expression with the ELP[V-20] tag was comparable to that of free thioredoxin, indicating that further reduction of the ELP tag would not be expected to increase the thioredoxin yield.

One possible explanation for the observed increase in thioredoxin yield as the ELP tag length was reduced is that, for given culture conditions, the mass of ELP that can be expressed by the cells is limited independent of ELP chain length. This is supported by the results in FIG. 26, as well as by observations with other ELPs of various molecular weight. Such a limitation would likely be engendered by a metabolic factor, perhaps by an insufficient tRNA pool and/or by amino acid depletion due to the highly repetitious ELP sequence. If the mass yield of ELP is a limiting factor, then this provides a rationale for the increased thioredoxin yields with the ELP[V-20] tag. For a given gravimetric yield of ELP, decreasing the ELP chain length increases the molar yield of the fusion protein, and hence, the target protein. Furthermore, this also suggests that increasing the gravimetric yield of ELP, e.g., through supplementation of specific, ELP-related amino acids during culture, offers another potential route for improvement of the fusion protein yield.

Although the yield of the target protein was increased with the shorter ELP[V-20] tag, this benefit entailed a more complicated transition behavior. The efficiency of recovery with this tag depends on the solution conditions used for ITC (FIG. 27), whereas, with the larger ELP[$V_5A_2G_3$-90] tag, recovery of the fusion protein was complete under all solution conditions (results not shown). Thus, although the truncated ELP[V-20] tag enabled thioredoxin to be purified to homogeneity by ITC, the efficiency of purification was sensitive to the specific conditions chosen to induce the inverse transition.

The turbidity and DLS data (FIGS. 13–24) provide insights into the sensitivity of purification efficiency for the smaller ELP[V-20] tag on solution conditions. While solutions of thioredoxin-ELP[$V_5A_2G_3$-90] remained turbid at all temperatures above $T_t$, the turbidity profiles for thioredoxin-ELP[V-20], after an initial rapid rise at $T_t$, began to clear with further heating at a temperature above $T_t$. This phenomenon of clearing with increasing temperature has not been previously observed, to my knowledge, with other ELPs or ELP fusion proteins. To study this complex aggregation behavior, the sizes of the fusion protein particles were measured using dynamic light scattering as a function of temperature to determine the structural basis for the markedly different turbidity profiles of the two fusion proteins.

With increasing temperature, monomers of thioredoxin-ELP[$V_5A_2G_3$-90] went through an abrupt, discontinuous phase transition to form aggregates that persisted at all temperatures above $T_t$ with a steady state $R_h$ of ~2 μm. Because the aggregates were stable above the $T_t$, the aggregated protein was able to be completely recovered by centrifugation at any temperature above its $T_t$ (or at any NaCl concentration for which the $T_t$ was depressed to below the solution temperature).

Although thioredoxin-ELP[V-20] also exhibited an abrupt phase transition to form aggregates, these aggregates were not stable at all temperatures above its phase transition. As the temperature was increased beyond the $T_t$, small aggregates with $R_h$ of ~12 nm formed at the expense of mass in the larger aggregates, which also showed a decrease in size with increasing temperature. This provides a structural rationale for the decrease in turbidity observed above the $T_t$ of thioredoxin-ELP[V-20]. Upon heating to temperatures greater than $T_t$ (beginning ~10° C. above $T_t$ for PBS with 1 M NaCl, and ~15° C. above $T_t$ for PBS with 2 M NaCl), larger scattering centers were converted to small particles that scatter light less effectively. The formation of these 12 nm particles at the expense of the larger aggregates resulted in incomplete recovery by centrifugation of the fusion protein from the soluble lysate. Thus, when ELP[V-20] (and potentially other small ELP tags) were used for purification of fusion proteins, it was imperative for complete protein recovery that a NaCl concentration and complimentary solution temperature be chosen such that only the larger aggregates, which are easily separable by centrifugation, were present in suspension.

On the basis of size alone, the precise structure of the 12 nm particle was not able to be predicted. However, the particle may be a micelle-like structure containing a small number of fusion protein molecules (perhaps on the order of 40 to 60) that are aggregated such that solvated thioredoxin domains encase the collapsed, hydrophobic ELP domains in the particle's core. The size of the observed particle ($R_h$≈12 nm) would be consistent with such a structure, as the hydrophilic thioredoxin "head" was ~3 nm in diameter and the hydrophobic 20 pentamer ELP "tail" was ~7 nm in length.

The proximity of the thioredoxin molecules required in such a micellular structure may also explain the irreversible aggregation that is observed at temperatures greater than ~55° C. Denaturation at this low temperature was only observed for thioreoxin fused to ELP[V-20], and only for NaCl concentrations of 1 M and greater. And, it is only for these conditions that the 12 nm particle was observed. An extremely high effective concentration of thioredoxin in the solvated, hydrophilic shell of the micelle, with little ELP buffering between thioredoxin molecules, is consistent with the observed decrease in thermal stability.

The examples in FIG. 27 illustrate the importance of appropriate selection of NaCl concentration and solution temperature during ITC. The three centrifugation temperatures were selected for experimental convenience: 12° C. when a microcentrifuge was placed in a 4° C. refrigerated laboratory cabinet, 33° C. when placed on a laboratory bench top at 22° C., and 49° C. when placed in a 37° C. static incubator (all sample temperatures were measured directly by thermocouple after a 10 minute centrifugation). The NaCl concentrations were selected in 1 M increments to depress the $T_t$ to some point below each centrifugation temperature.

For the first two examples (FIG. 27, left and center), recovery was incomplete because at these combinations of centrifugation temperature and NaCl concentration, thioredoxin-ELP[V-20] showed a two phase behavior where larger aggregates coexisted with the 12 nm particles. Because of their small mass, these particles remained suspended during centrifugation, and only the fraction of fusion protein contained in the larger aggregate phase was removed by centrifugation and recovered in the resolubilized pellet. At 49° C., the thioredoxin-ELP[V-20] turbidity profile in PBS with 1 M NaCl was significantly decreased from its maximum value (FIG. 13), and data showed that a majority of the scattering intensity came from the 12 nm particles (FIGS. 21 and 22). Correspondingly, the SDS-PAGE data in FIG. 27 shows that only a small fraction of the fusion protein present was captured by centrifugation during ITC purification. At 33° C. in PBS with 2 M NaCl, although still below its maximum value, the turbidity of thioredoxin-ELP[V-20] was closer to its peak value (FIG. 13), and the data shows that the scattering intensity attributed to the 12 nm particle was much smaller (FIGS. 23 and 24). Consistent with these observations, a majority of fusion protein was captured by ITC purification as ascertained by SDS-PAGE in FIG. 25, although loss in the supernatant due to the 12 nm particles was still significant.

Using a centrifugation temperature of 12° C. in PBS with 3 M NaCl, recovery of the fusion protein in the resolubilized pellet was nearly complete (FIG. 27, right). Under these conditions, the solution turbidity was very near its maximum value (FIG. 13). The degree of turbidity, combined with the trends in particle size distribution established for lower salt concentrations in FIGS. 21–24, suggest that the complete recovery obtained by ITC with these conditions is explained by the presence of only the larger aggregates for these solution conditions.

These examples illustrate that for efficient ITC purification of thioredoxin-ELP[V-20], and potentially for other soluble fusion proteins with small ELP tags, the NaCl concentration and centrifugation temperature should be selected to achieve the maximum point in the turbidity profile. For microcentrifuges without temperature control, this is most practically achieved by determining the centrifuge sample temperature, and then adjusting the $T_t$ of the fusion protein by the precise addition of salt. For larger centrifuges that are equipped with refrigeration systems, recovery efficiency can be maximized by the combined alteration of NaCl concentration and centrifugation temperature. The required precision in controlling solution conditions during ITC for thioredoxin-ELP[V-20] versus that for thioredoxin-ELP[$V_5A_2G_3$-90], which can be fully recovered using any combination of temperature and salt concentration that induces the inverse transition, is the price paid for the four-fold increase in yield of the target protein.

Decreasing the length of the ELP purification tag from 36 to 9 kDa produced a four-fold increase in the expression levels of *E. coli* thioredoxin, a model target protein. The expression level with the 9 kDa tag was similar to that of free thioredoxin expressed without an ELP tag, and therefore further reduction of the ELP tag size is not likely to provide any additional benefit. Although truncation of the ELP did not adversely affect the purity of the final protein product, it is important to select an appropriate combination of salt concentration and solution temperature to favor the formation of larger aggregates during ITC purification.

6.9 High-Throughput Purification of Recombinant Proteins Using ELP Tags

6.9.1 Fusion Protein Construction

The gene for the 5 - polypentapeptide ELP sequence was constructed by annealing two 5'-phosphorylated synthetic oligonucleotides (Integrated DNA Technologies, Coralville, Iowa) to yield double stranded DNA with PflMI and HinDIII compatible ends. This gene was inserted into a PflMI/HinDIII linearized and dephosphorylated modified pUC-19 (New England Biolabs, Beverly, Mass.) vector and polymerized using recursive directional ligation with PflMI and BglI (Meyer, 1999; Meyer, 2000) to generate the gene for the 20- polypentapeptide ELP sequence. This ELP gene was then excised with PflMI and BglI, gel purified (QIAquick Gel Extraction Kit, Qiagen, Valencia, Calif.), and inserted into a SfiI linearized and dephosphorylated modified pET32b vector (Novagen, Madison, Wis.; Meyer, 1999). This expression vector was then transformed into the BLR (DE3) (Novagen) *E. coli* expression strain.

6.9.2 Protein Expression

The aforementioned cells were taken from frozen (DMSO) stock and streaked onto agar plates supplanted with 100 μg/ml ampicillin and allowed to grow overnight. Two hundred microliters of growth media (100 μg/ml ampicillin in CircleGrow media; Qbiogene, Inc., Carlsbad, Calif.) were injected into each well of a standard 96 well microplate (Costar, Corning Inc., Corning, N.Y.) using a multichannel pipetter. Using 200 μl pipet tips, each well of the microplate was inoculated with a pinhead-sized aggregation of cells from colonies on the aforementioned agar plates. With the lid on, the microplate was incubated at 37° C. and shaken at 275 r.p.m. The microplate was held in place in the shaker using an ad hoc microplate holder. The cultures were induced by adding isopropyl α-thiogalactopyranoside to a final concentration of 1 mM when the $OD_{650}$ reached 0.65 for a majority of the cultures as measured using a microplate reader (Thermomax; Molecular Devices Co., Sunnyvale, Calif.)—this optical density corresponds to an $OD_{650}$ of 2.0 as measured using an UV-visible spectrophotometer (UV-1601, Shimadzu Scientific Instruments, Inc.). The cultures were incubated and shaken for 4 hours post-induction and then harvested by centrifugation at 1100 g for 40 minutes at 4° C. using matched-weight microplate carrier adaptors (Beckman Instruments, Inc., Palo Alto, Calif.). The media was discarded and the cell pellets were frozen in the microplates at −80° C. until they were ready to be purified.

6.9.3 Protein Purification

The ELP4-20/thioredoxin protein was purified from cell cultures in the microplates as follows. The cells were lysed by adding 1 μl of lysozyme solution (25 mg/ml; Grade VI; Sigma, St. Louis, Mo.) and 25 ul of lysis buffer (50 mM NaCl, 5% glycerol, 50 mM Tris-HCl, pH 7.5) to each well. The microplate was then shaken using an orbital shaker at 4° C. for 20 minutes. Two μl of 1.35% (by mass) sodium doxycholate solution were added to each well and the microplate was shaken at 4° C. for 5 minutes. Two μl of deoxyribonuclease I solution (100 units/ul; Type II; Sigma, St. Louis, Mo.) were added to each well and the microplate was shaken at 4° C. for 10 minutes. The microplate was then centrifuged at 1100 g for 20 minutes at 4° C. using matched-weight microplate carrier adaptors (Beckman Instruments, Inc., Palo Alto, Calif.) to pellet cell particulates and insoluble proteins. Two μl of 10% (by mass) polyethylenimine solution was added to each well and the microplate was shaken at 4° C. for 15 minutes. The microplate was then centrifuged at 1100 g for 20 minutes at 4° C. to pellet DNA. The supernatants were transferred to wells on a new microplate and the old microplate was discarded. To induce ELP4-20/thioredoxin aggregation, 20 μl of saturated NaCl solution was added to each well; a marked increase in turbidity indicated aggregation of the target protein. To pellet the aggregated proteins, the microplate was centrifuged at 1100 g for 40 minutes at 30° C. The protein pellets were resolubilized in 30 μl of phosphate buffer solution after which the microplate was centrifuged at 1100 g for 20 minutes at 4° C. to remove insoluble lipids. Finally, the purified protein supernatents were transferred to wells of a new microplate and stored at 4° C.

6.9.4 Protein Quantitization

Protein concentration was determined by measuring $A_{280}$ (UV- 1601, Shimadzu Scientific Instruments, Inc.) and using the molar extinction coefficient for ELP4-20/Thioredoxin (ϵ=19,870); this assumes that the ELP4-20/Thioredoxin protein samples are pure of protein and DNA impurities. Thioredoxin activity was determined using an insulin reduction assay (Holmgren, 1984).

6.9.5 Results and Discussion

For the construction of the fusion protein, a small ELP tag was designed with a $T_t$ of around 70° C., using previously published theoretical $T_t$ data (Urry, 1991). Characterization of the ELP tag showed that the $T_t$ was 76.2° C., confirming that it is possible to rationally design ELP tags with specified $T_t$. For the ELP/thioredoxin fusion protein, the $T_t$ in low salt buffer, 1 M, and 2 M salt solutions were 68° C., 37° C. and 18° C., respectively, confirming that fusion of a soluble protein to an ELP tag minimally affects its $T_t$ and showing that the $T_t$ can be manipulated over a wide range by adjusting the salt concentration.

Based on the foregoing, the creation of a family of plasmid expression vectors that contain an ELP sequence and a polylinker region (into which the target protein is inserted) joined by a cleavage site can be employed to facilitate the expression of a variety of proteins. The ELP sequences embedded in such family of plasmids can have different transition temperatures (by varying the identity of the guest residue). The expression vector for a particular target protein is desirably selected based on the protein's surface hydrophobicity characteristics. The salt concentration of the solution then is adjusted during purification to obtain the desired $T_t$.

For protein expression involving growth of cell cultures in microplate wells, the cell cultures can be desirably induced at $OD_{600} \approx 2$ and grown for 4 hours post-induction. The cell density at induction for the microplate growths is two to three times that achieved by conventional protein expression protocols. Even at these high cell densities, rapid and healthy cell growth can be maintained in the microplate wells by aeration of the cultures, which as grown in the wells are characterized by a high surface area to volume ratio. Cell cultures that are grown longer post-induction yielded minimally more target protein, and growth using a hyper expression protocol (Guda, 1995) had much more contaminant protein (around tenfold) with minimally more fusion protein. In order to avoid evaporation of the cell media in the high surface area to volume ratio cell growth in the microplate wells, it was necessary to cover the microplate with an appropriate lid during growth and to infuse the cell growth with additional media during induction. On a per liter basis, cultures grown in the microplate wells had a higher level of fusion protein expression than cultures grown with conventional protocols.

High throughput protein purification utilizing ITC was successful when cells were lysed with commercial nonionic protein extraction formulations. After cell lysis, addition of polyethylenimine removed nucleic acids and high molecular mass proteins from the soluble fraction of the crude lysate upon centrifugation. At the fusion protein and salt concentrations of the soluble lysate, the $T_t$ of the fusion protein was approximately 65° C. Heating the soluble lysate above this temperature to induce fusion protein aggregation denatures and precipitates soluble contaminant proteins as well as the target protein itself. Furthermore, this temperature could not be maintained within the centrifuge chamber during centrifugation. Therefore, salt was added to the soluble lysate to approximately 2 M; this depressed the $T_t$ of the fusion protein to approximately 18° C., allowing for aggregation of the fusion protein at room temperature. This salt concentration did not precipitate any contaminant proteins nor did it alter the functionality of the final purified protein product.

High throughput protein purification using ITC was both effective and efficient. About 15% of the expressed fusion protein was lost in the insoluble protein fraction of the cell lysate. Centrifugation of the sample after fusion protein aggregation effectively separated the proteins: 90% of the fusion protein was pelleted while 10% of the fusion protein remained in the supernatant along with all soluble contaminant proteins. Overall, about 75% of the expressed protein was abstracted using ITC purification and *E. coli* contaminant protein levels in the purified products were below those detectable by SDS-PAGE. The purification process can be expedited and purification efficiency increased by increasing the centrifugation speeds; higher centrifugation speeds allow for reduced centrifugation times and at higher centrifugation speeds (5000 g), all of the fusion protein is pelleted during centrifugation post aggregation. Addition of thrombin completely cleaved the fusion protein and a second round of ITC separated the ELP tag from the thioredoxin target protein with no loss of thioredoxin.

The average amount of fusion protein purified per well determined using absorbance measurements ($A_{280}$, $\epsilon=19,870$) was 33 $\mu$g with a standard deviation of 8.5 $\mu$g. Values were dispersed evenly between 19.7 and 48.3 $\mu$g per well. The large variation in yield of purified protein was due more to the different amounts of protein expressed in the different wells than to a variation in the purification efficiency of the ITC process. Varying amounts of protein were expressed in the different cell cultures because 1) the imprecision of the inoculation meant that cell cultures had varying amounts of cells to begin with and 2) due in all likelihood to more abundant aeration, the cell cultures in peripheral wells tended to have faster growth and reach a higher stationary phase cell density. For simplicity of effort, all of the cell cultures were induced and then harvested at the same times as opposed to induction and harvesting of individual cell cultures.

The enzymatic activity of the thioredoxin target protein was measured using an insulin reduction assay. The average amount of fusion protein per well, determined on the basis of such enzymatic activity, was 35.7 $\mu$g with a standard deviation of 8.0 $\mu$g. Again, values were dispersed evenly, between a minimum of 24.6 and a maximum of 50.8 $\mu$g per well. It is important to note that thioredoxin was enzymatically active though still attached to the ELP tag. The thioredoxin expressed and purified using this high throughput ITC technique had, on average, 10.3% greater enzymatic activity per unit mass than that of commercial thioredoxin (Sigma), a testament to the gentleness of and purity achieved by the ITC process.

On average, high throughput ELP/thioredoxin protein expression and purification produced around 160 mg of protein per liter of growth. This is comparable to ELP/thioredoxin yields obtained using conventional protein expression and ITC purification methods (140–200 mg protein/L of growth).

FIG. 28 is an SDS-PAGE gel of the stages of high throughput protein purification using microplates and inverse transition cycling according to the above-described procedure, in which ELP/thioredoxin fusion protein was purified (Lane 1: molecular mass markers (kDa) (Sigma, wideband; Lane 2: crude lysate; Lane 3: insoluble proteins; Lane 4: soluble lysate; Lane 5: supernatant containing contaminant proteins; Lane 6: purified ELP/thioredoxin fusion protein; and Lanes 7 and 8: purified ELP/thioredoxin fusion proteins from other wells). The ELP/thioredoxin fusion protein was purified using the documented protocol. Gel samples were denatured with SDS, reduced with beta-mercaptoethanol, and run at 200 V for 45 minutes on a 10–20% gradient Tris-HCl gel.

FIGS. 29–30 show histograms for quantitization of purified protein samples. FIG. 29 is a histogram of total fusion protein per well as determined using absorbance measurements ($A_{280}$, $\epsilon$=19,870) (n=20, $\mu$=32.97, $\sigma$=8.48). FIG. 30 is a histogram of fusion protein functionality/purity for each sample compared to commercial thioredoxin (from Sigma) (n=20, $\mu$=10.37%, $\sigma$=16.54%).

Considering the high throughput protein expression and purification method of the invention, it is noted that whereas nickel-chelated multiwell plates can purify only 1 ng of His-tagged protein per well, the capacity of high throughput purification using ITC is limited only by the amount of the protein that can expressed by cultures grown in the well; for ELP tagged proteins, the level of protein expression is in the tens of microgram range.

High throughput purification using ITC thus provides high yields, producing sufficient protein for multiple assays and analyses. Milligram levels of purified protein can be obtained by growing cell cultures in other vessels and transferring the resuspended cell pellet to the multiwell plate for the purification process. Finally, such high throughput purification technique is technically simpler and less expensive than current conventional commercial high throughput purification methods as it requires only one transfer of purification intermediates to a new multiwell plate.

7. References

Throughout this specification various patent and non-patent references have been cited. The entire disclosure of each of these references is incorporated herein by reference, specifically including without limitation the following references:

1 Urry, D. W. Entropic elastic processes in protein mechanisms. I. Elastic structure due to an inverse temperature transition due to internal chain dynamics. J. Prot. Chem. 7:1–34 (1988).
2. Urry, D. W. Free energy transduction in polypeptides and proteins based on inverse temperature transitions. Prog. Biophys. Molec. Biol. 57:23–57 (1992).
3. Urry, D. W. Physical chemistry of biological free energy transduction as demonstrated by elastic protein-based polymers J. Phys. Chem. B 101: 11007–11028 (1997).
4. McPherson, D. T., Xu, J., and Urry, D. W. Product purification by reversible phase transition following Escherichia coli expression of genes encoding up to 251 repeats of the elastomeric pentapeptide GVGVP. Protein Expr Purif 7: 51–57 (1996).
5. Hoffman. A. S. Applications of thermally-reversible polymers and hydrogels in therapeutics and diagnostics. J. Controlled Release 6:297–305 (1987).
6. Chen, J. P. and Hoffman A. S. Protein-polymer conjugates II. Affinity precipitation separation of immunogammaglobulin by a poly(N-isopropylacrylamide)-protein A conjugate. Biomaterials 11:631–634 (1990).
7. Chilkoti, A., Chen, G-H., Stayton, P. S. and Hoffman, A. S. Site-specific conjugation of a temperature-sensitive polymer to a genetically-engineered protein. Bioconj. Chem. 5:504–507 (1994).
8. Nilsson, B., Forsberg, G., Moks, T., Hartmanis, M. and Uhlén, M. Fusion proteins in biotechnology and structural biology. Curr. Opin. Struct. Biol. 2:569:575 (1992).
9. Uhlén, M. and Moks, T. Gene fusions for purpose of expression: An introduction. Meth. Enzymol. 195:129–143 (1990).
10. Maina, C. V., Riggs, P. D., Grandea, A. G., III, Slatko, B. E., Moran, L. S., Tagliamonte, J. A., McReynolds, L. A. and diGuan, C. An *Escherichia coli* vector to express and purify foreign proteins by fusion to and separation from maltose binding protein. Gene 74:365–373 (1988).
11. Smith, D. B. and Johnson, K. S. Single-step purification of polypeptides expressed in Escherichia coli as fusions with glutathione S-transferase. Gene 67:31–40 (1988).
12. Tsao, K. W., deBarbieri, B., Hanspeter, M. and Waugh, D. W. A versatile plasmid expression vector for the production of biotinylated proteins by site-specific, enzymatic modification in *Escherichia coli*. Gene 169: 59–64 (1996).
13. Smith, P. A., Tripp, B. C., DiBlasio-Smith, E. A., Lu, Z., LaValle, ER. and McCoy, J. A. A plasmid expression system for quantitative in vivo biotinylation of thioredoxin fusion proteins in *Escherichia coli*. Nucl. Acid. Res. 26:1414–1420 (1998).
14. LaVallie, E. R., DiBlasio, E. A., Kovacic, S., Grant, K. L., Schendel, P. F. and McCoy, J. M. A thioredoxin gene fusion expression system that circumvents inclusion body formation in the E. coli cytoplasm. Bio/Technology 11:187–193 (1993).
15. Ong, E., Greenwood, J. M., Gilkes, N. R., Kilburn, D. G., Miller, R. C. Jr. and Warren, R. A. The cellulose-binding domains of cellulases: tools for biotechnology. Trends. Biotechnol. 7:239–243 (1989).
16. Smith, M. C., Furman, T. C., Ingolia, T. D. and Pidgeon, C. Chelating peptide-immobilized metal ion affinity chromatography. J. Biol. Chem. 263:7211–7215 (1988).
17. Kim, J-S. and Raines, R. T. Ribonuclease S-peptide as a carrier in fusion proteins. Prot. Sci. 2:348–356 (1993).
18. Su, X., Prestwood, A. K. and McGraw, R. A. Production of recombinant porcine tumor necrosis factor alpha in a novel E. coli expression system. Biotechniques 13:756–762 (1992).
19. Nilsson, J., Ståhl, S., Lundeberg, J., Uhlén, M., and Nygren, P. A. Affinity Fusion Strategies for Detection, Purification, and Immobilization of Recombinant Proteins. Protein Expr Purif 11: 1–16 (1997).
20. coligan, J. E., Dunn, B. M., Ploegh, H. L., Speicher, D. W. and Wingfield, P. T. Current protocols in protein science, John Wiley, (1995).
21. See Doi, Regulation of Gene Expression, Modem Microbial Genetics pages 15–39 (1991).
22. Hartmeier, W. Immobilized biocatalysts, Springer-Verlag, Berlin (1988).
23. Diamandis, E. P. and Christopoulos, T. K. Immunoassay, Academic Press, San Diego (1996).
24. Dehwirst, M. W. and Samulski, T. V. Hyperthermia in the treatment of cancer. Current Concepts 1–48 (1988).
25. Hauck, M. L., Dewhirst, M. W., Bigner, D. D. and Zalutsky, M. R. Local hyperthermia improves uptake of a chimeric monoclonal antibody in a subcutaneous xenograft model. Clin. Cancer Res. 3:63–70 (1997).
26. Cope, D. A., Dewhirst, M. W., Friedman, H. S., Bigner, D. D. and Zalutsky, M. R. Enhanced delivery of a monoclonal antibody F(ab')2 fragment to subcutaneous human glioma xenografts using local hyperthermia. Cancer Res. 50:1803–1809 (1990).
27. Vertesy, L., Oeding, V., Bender, R., Zepf, K., and Nesemann, G. Tendamistat (HOE 467), a tight-binding alpha-amylase inhibitor from *Streptomyces tendae* 4158. Eur. J. Biochem 141:505–512 (1984).
28. Urry, D. W., Luan, C H., Parker, T. M., Gowda, D. C., Prasad, K. U., Reid, M. C. and Safavy A. Temperature of polypeptide inverse temperature transition depends on mean residue hydrophobicity. J. Am. Chem. Soc. 113:4346–4348 (1991).
29. Urry, D. W., Trapane, T. L., and Prasad, K. U. Phase-structure transitions of the elastin polypentapeptide-water system within the framework of composition-temperature studies. Biopolymers 24:2345–2356 (1985).

30. Porath, J. Immobilized metal ion affinity chromatography. Prot. Expr. Purif. 3:262–282 (1992).
31. Holmgren, A. Thioredoxin. Annu. Rev. Biochem. 54:237–271 (1985).
32. Ausubel, F. M., Brent, R., Kingston, R. E., Moore, D. H., Seidman, J. G., Smith, J. A. and Struhl, K. Current protocols in molecular biology, John Wiley, New York (1995).
33. Smith, P. K., Krohn, R. I., Hermanson, G. T., Mallia, A. K., Gartner, F. H., Provenzano, M. D., Fujimoto, E. K., Goeke, N. M., Olson, B. J. and Klenk, D. C. Measurement of protein using bicinchonic acid. Anal. Biochem. 150:76–85 (1986).
34. Holmgren, A. and Bjornstedt, M. Enzymatic reduction-oxidation of protein disulfides by thioredoxin. Methods Enzymol. 107:295–300 (1984).
35. Meyer, D. and Chilkoti, A. Purification of Recombinant Proteins by Fusion with Thermally Responsive Polypeptides. Nat. Biotechnol. 17. 1112–1115 (1999)
36. Meyer, D. and Chilkoti, A. Genetically Encoded Synthesis of Protein-Based Polymers with Precisely Specified Molecular Weight and Sequence by Recursive Directional Ligation. Biomacromolecules (2001).
37. McPherson, D., Morrow, C., Minhan, D. Wu, J., Hunter, E., Urry, D. Production and purification of a recombinant elastomeric polypeptide, G-(VPGVG)$_{19}$-VPGV from *Eschericia coli*. Biotechnol. Prog. 8: 347–352 (1992).

What is claimed is:

1. A fusion protein comprising:

(a) one or more biological molecules selected from the group consisting of peptides and proteins;

(b) one or more phase transition proteins that exhibit an inverse phase transition wherein the one or more phase transition proteins are joined to the biological molecule(s) of (a); and (c) optionally, a spacer sequence separating any of the phase transition protein(s) of (b) from any of the biological molecule(s) of (a), wherein the fusion protein retains the inverse phase transition behavior of the phase transition protein(s) of (b) and wherein said phase transition protein(s) has a molecular weight of at least 9,000 Daltons, and wherein the one or more phase transition protein(s) of (b) comprises oligomeric repeats of the pentapeptide Val- Pro-Gly-X-Gly, wherein X is any natural or non-natural amino acid residue, and wherein X optionally varies among oligomeric repeats.

2. The fusion protein of claim 1 wherein the biological molecule of 1(a) comprises a peptide.

3. The fusion protein of claim 1 wherein the biological molecule of 1(a) comprises a biologically active protein.

4. The fusion protein of claim 1 wherein the biological molecule of 1(a) comprises a therapeutic protein.

5. The fusion protein of claim 1 wherein the biological molecule of 1(a) comprises an enzyme useful in industrial biocatalysis.

6. The fusion protein of claim 1 wherein the biological molecule of 1(a) comprises an antibody or antibody fragment.

7. The fusion protein of claim 6 wherein the antibody or antibody fragment has complex forming affinity for an antigenic protein of interest, and wherein upon binding to the antigenic protein of interest, the fusion protein retains its phase transition character.

8. The fusion protein of claim 1 wherein the phase transition is mediated by one or more means selected from the group comprising:

changing temperature;

changing pH;

addition of solutes and/or solvents, side-chain ionization or chemical modification; and changing pressure.

9. The fusion protein of claim 1 wherein the phase transition is mediated by means comprising raising temperature.

10. The fusion protein of claim 1 wherein the X component(s) of the oligomeric repeats comprise(s) a naturally-occurring amino acid residue.

11. The fusion protein of claim 1 wherein the X component(s) of the oligomeric repeats comprise(s) a non-naturally-occurring amino acid residue.

12. The fusion protein of claim 1 wherein X varies among said oligomeric repeats.

13. The fusion protein of claim 1 wherein any two or more of the oligomeric repeats are separated by one or more amino acid residues which do not eliminate the phase transition characteristic of the fusion protein.

14. The fusion protein of claim 1 wherein the ratio of Val-Pro-Gly-X-Gly oligomeric repeats to other amino acid residues of the phase transition protein(s) of 1(b) is greater than about 75%.

15. The fusion protein of claim 1 wherein the ratio of Val-Pro-Gly-X-Gly oligomeric repeats to other amino acid residue of the phase transition protein(s) of 1(b) is greater than about 85%.

16. The fusion protein of claim 1 wherein the ratio of Val-Pro-Gly-X-Gly oligomeric repeats to other amino acid residues of the phase transition protein(s) of 1(b) is greater than about 95%.

17. The fusion protein of claim 1 wherein the spacer sequence comprises a proteolytic cleavage site.

18. The fusion protein of claim 1 wherein the fusion protein further comprises a signal peptide.

19. The fusion protein of claim 18 wherein the signal peptide is cleavable from the fusion protein by enzymatic cleavage.

20. The fusion protein of claim 18 wherein the signal peptide directs secretion of the fusion protein from the cell.

21. The fusion protein of claim 1 wherein the fusion protein is recombinantly produced.

22. The fusion protein of claim 1 wherein any of the biological molecule(s) of 1(a), phase transition protein(s) of 1(b), or spacer sequence of 1(c) (when present) is recombinantly produced.

23. A fusion protein comprising:

(a) one or more biological molecules selected from the group consisting of peptides and proteins;

(b) one or more phase transition protein(s) that exhibit an inverse phase transition, wherein the one or more phase transition protein(s) are joined to the biological molecule(s) of (a); and (c) optionally, a spacer sequence separating any of the phase transition protein(s) of (b) from any of the biological molecules of (a), wherein the fusion protein retains the inverse phase transition behavior of the phase transition proteins of (b) and wherein said phase transition protein(s) comprises at least thirty repeats of the pentapeptide Val-Pro-Gly-X-Gly, in which X is any natural or non-natural amino acid residue.

24. The fusion protein of claim 23 wherein the phase transition is mediated by means comprising raising temperature.

25. A fusion protein comprising:

(a) one or more biological molecules selected from the group consisting of peptides and proteins;

(b) one or more phase transition proteins that exhibit an inverse phase transition, wherein the one or more phase transition proteins are joined to the biological molecule(s) of (a); and (c) optionally, a spacer sequence separating any of the phase transition protein(s) of (b) from any of the biological molecule(s) of (a), wherein the fusion protein retains the inverse phase transition behavior of the phase transition proteins of (b), wherein said phase transition protein(s) comprises oligomeric repeats of the pentapeptide Val-Pro-Gly-X-Gly, in which X is any natural or non-natural amino acid residue, and wherein said phase transition protein(s) has a molecular weight of at least 9,000 Daltons, wherein the one or more biological molecules of (a) is proteolytically cleavable from the fusion protein; and wherein the phase transition is mediated by one or more means selected from the group comprising: changing temperature; changing pH; addition of solutes and/or solvents, side-chain ionization or chemical modification; and changing pressure.

26. The fusion protein of claim 25 wherein the phase transition is mediated by raising temperature.

27. The fusion protein of claim 8, wherein the phase transition is mediated by addition of solute.

28. The fusion protein of claim 27, wherein the solute comprises an organic solute.

29. The fusion protein of claim 27, wherein the solute comprises an ionic solute.

30. The fusion protein of claim 29, wherein the ionic solute comprises a salt.

31. The fusion protein of claim 30, wherein the salt comprises NaCl.

32. An elastin-like polypeptide (ELP) fusion protein comprising a protein of interest and an elastin-like polypeptide component coupled by a cleavage site in a composition comprising a solvent medium in which the ELP fusion protein exhibits an inverse phase transition wherein the phase transition is mediated by at least one change selected from the group consisting of:

(a) changing temperature;

(b) changing pH;

(c) addition of solutes and/or solvents;

(d) side-chain ionization or chemical modification; and (e) changing pressure, wherein the elastin-like polypeptide component comprises oligomeric repeats of the pentapeptide Val-Pro-Gly-X-Gly, in which X is any natural or non-natural amino acid residue, and wherein said phase transition protein(s) has a molecular weight of at least 9,000 Daltons.

33. The ELP fusion protein of claim 32, wherein the protein of interest is cleavable from the elastin-like polypeptide component at the cleavage site to yield the protein of interest and the elastin-like polypeptide component as cleavage products.

34. The fusion protein of claim 1, wherein said one or more biological molecules of (a) is cleavable from the fusion protein by a cleavage agent.

35. The ELP fusion protein of claim 33, wherein said cleavage agent is a proteolytic agent for proteolytically cleaving the cleavage site of the fusion protein.

36. The fusion protein of claim 1 wherein the phase transition protein(s) comprise a β-turn structure.

37. The fusion protein of claim 23, having a phase transition temperature in a range of from about 35 to about 60° C.

38. The fusion protein of claim 1 wherein the phase transition protein(s) of (b) are joined to the N-terminus of the biological molecule(s) of (a).

39. The fusion protein of claim 17 wherein the proteolytic cleavage site is cleavable by a protease agent selected from the group consisting of serine, cysteine, aspartyl and metallo-proteases.

40. A fusion protein comprising:

(a) one or more biological molecules selected from the group consisting of peptides, therapeutic proteins and antibodies or antibody fragments;

(b) one or more phase transition proteins that exhibit an inverse phase transition, wherein the one or more phase transition proteins are joined to the biological molecule(s) of (a); and (c) optionally, a spacer sequence separating any of the phase transition protein(s) of (b) from any of the biological molecule(s) of (a), wherein the one or more phase transition proteins of (b) comprises at least thirty repeats of the pentapeptide Val-Pro-Gly-X-Gly, in which X is any natural or non-natural amino acid residue, wherein the phase transition is mediated by one or more means selected from the group comprising: changing temperature; changing pH; addition of solutes and/or solvents, side-chain ionization or chemical modification; and changing pressure, wherein the fusion protein retains the inverse phase transition behavior of the one or more phase transition proteins of (b).

41. A fusion protein comprising:

(a) one or more biological molecules selected from the group consisting of superoxide dismutase, interferon, asparaginease, glutamase, arginase, arginine deaminase, adenosine deaminase ribonuclease, trypsin, chromotrypsin, papin, insulin, calcitonin, adrenocorticotropic hormone (ACTH), glucagon. somatosin, somatropin, somatomedin, parathyroid hormone, erthyropoietin, hypothalamic releasing factors, prolactin, thyroid stimulating hormones, endorphins, enkephalins, and vasopressin;

(b) one or more phase transition proteins that exhibit an inverse phase transition, wherein the one or more phase transition proteins are joined to the biological molecule(s) of (a), and wherein said phase transition protein(s) comprises oligomeric repeats of the pentapeptide Val-Pro-Gly-X-Gly, in which X is any natural or non-natural amino acid residue; and (c) optionally, a spacer sequence separating any of the phase transition protein(s) of (b) from any of the biological molecule(s) of (a), wherein the fusion protein retains the inverse phase transition behavior of the phase transition proteins of (b).

* * * * *

UNITED STATES PATENT AND TRADEMARK OFFICE
CERTIFICATE OF CORRECTION

PATENT NO. : 6,852,834 B2
DATED : February 8, 2005
INVENTOR(S) : Ashutosh Chilkoti It is certified that error appears in the above-identified patent and that said Letters Patent is hereby corrected as shown below:

Column 1,
Line 29, "polypeptide" should be -- polypeptides$^4$. --

Column 9,
Line 37, "Sequence ID No. 2)," should be -- (Sequence ID No. 2), --

Column 30,
Line 61, "[VsA$_2$G$_3$-90]" should be -- [V$_5$A$_2$G$_3$-90] --

Column 40,
Line 38, "Modem" should be -- Modern --

Signed and Sealed this

Seventh Day of June, 2005

JON W. DUDAS
*Director of the United States Patent and Trademark Office*

SEQUENCE LISTING

<160> NUMBER OF SEQ ID NOS: 7

<210> SEQ ID NO 1
<211> LENGTH: 5
<212> TYPE: PRT
<213> ORGANISM: Artificial Sequence
<220> FEATURE:
<223> OTHER INFORMATION: pentapeptide monomer
<221> NAME/KEY: UNSURE
<222> LOCATION: (4)..(4)
<223> OTHER INFORMATION: X can be any amino acid, natural or non-natural.

<400> SEQUENCE: 1

Val Pro Gly Xaa Gly
1               5

<210> SEQ ID NO 2
<211> LENGTH: 5
<212> TYPE: PRT
<213> ORGANISM: Artificial Sequence
<220> FEATURE:
<223> OTHER INFORMATION: Pentapeptide monomer
<221> NAME/KEY: UNSURE
<222> LOCATION: (4)..(4)
<223> OTHER INFORMATION: X can be any amino acid, natural or non-natural.

<400> SEQUENCE: 2

Ile Pro Gly Xaa Gly
1               5

<210> SEQ ID NO 3
<211> LENGTH: 50
<212> TYPE: PRT
<213> ORGANISM: ELP[V5A2G3-10]

<400> SEQUENCE: 3

Val Pro Gly Val Gly Val Pro Gly Val Gly Val Pro Gly Val Gly Val
1               5                   10                  15

Pro Gly Val Gly Val Pro Gly Val Gly Val Pro Gly Ala Gly Val Pro
            20                  25                  30

Gly Ala Gly Val Pro Gly Gly Gly Val Pro Gly Gly Gly Val Pro Gly
        35                  40                  45

Gly Gly
    50

<210> SEQ ID NO 4
<211> LENGTH: 25
<212> TYPE: PRT

-continued

<213> ORGANISM: ELP[V-5]

<400> SEQUENCE: 4

Val Pro Gly Val Gly Val Pro Gly Val Gly Val Pro Gly Val Gly Val
1               5                   10                  15

Pro Gly Val Gly Val Pro Gly Val Gly
            20                  25

<210> SEQ ID NO 5
<211> LENGTH: 75
<212> TYPE: DNA
<213> ORGANISM: ELP[V-5]

<400> SEQUENCE: 5
gtgggtgttc cgggcgtagg tgtcccaggt gtgggcgtac cgggcgttgg tgttcctggt      60
gtcggcgtgc cgggc                                                      75

<210> SEQ ID NO 6
<211> LENGTH: 450
<212> TYPE: PRT
<213> ORGANISM: ELP[V5A2G3-90]

<400> SEQUENCE: 6

Val Pro Gly Val Gly Val Pro Gly Val Gly Val Pro Gly Val Gly Val
1               5                   10                  15

Pro Gly Val Gly Val Pro Gly Val Gly Val Pro Gly Ala Gly Val Pro
            20                  25                  30

Gly Ala Gly Val Pro Gly Gly Val Pro Gly Gly Val Gly Val Pro Gly
        35                  40                  45

Gly Gly Val Pro Gly Val Gly Val Pro Gly Val Gly Val Pro Gly Val
    50                  55                  60

Gly Val Pro Gly Val Gly Val Pro Gly Val Gly Val Pro Gly Ala Gly
65                  70                  75                  80

Val Pro Gly Ala Gly Val Pro Gly Gly Val Pro Gly Gly Gly Val
                85                  90                  95

Pro Gly Gly Gly Val Pro Gly Val Gly Val Pro Gly Val Gly Val Pro
            100                 105                 110

Gly Val Gly Val Pro Gly Val Gly Val Pro Gly Val Gly Val Pro Gly
        115                 120                 125

Ala Gly Val Pro Gly Ala Gly Val Pro Gly Gly Val Pro Gly Gly
    130                 135                 140

Gly Val Pro Gly Gly Gly Val Pro Gly Val Gly Val Pro Gly Val Gly
145                 150                 155                 160

Val Pro Gly Val Gly Val Pro Gly Val Gly Val Pro Gly Val Gly Val
                165                 170                 175

Pro Gly Ala Gly Val Pro Gly Ala Gly Val Pro Gly Gly Gly Val Pro
            180                 185                 190

Gly Gly Gly Val Pro Gly Gly Val Pro Gly Val Gly Val Pro Gly
        195                 200                 205

Val Gly Val Pro Gly Val Gly Val Pro Gly Val Gly Val Pro Gly Val
    210                 215                 220

Gly Val Pro Gly Ala Gly Val Pro Gly Ala Gly Val Pro Gly Gly Gly
225                 230                 235                 240

Val Pro Gly Gly Gly Val Pro Gly Gly Gly Val Pro Gly Val Gly Val
                245                 250                 255

Pro Gly Val Gly Val Pro Gly Val Gly Val Pro Gly Val Gly Val Pro

```
                        260                 265                 270
Gly Val Gly Val Pro Gly Ala Gly Val Pro Gly Ala Gly Val Pro Gly
            275                 280                 285
Gly Gly Val Pro Gly Gly Val Pro Gly Gly Val Pro Gly Val
        290                 295                 300
Gly Val Pro Gly Val Gly Val Pro Gly Val Gly Val Pro Gly Val Gly
305                 310                 315                 320
Val Pro Gly Val Gly Val Pro Gly Ala Gly Val Pro Gly Ala Gly Val
                325                 330                 335
Pro Gly Gly Gly Val Pro Gly Gly Val Pro Gly Gly Gly Val Pro
            340                 345                 350
Gly Val Gly Val Pro Gly Val Gly Val Pro Gly Val Gly Val Pro Gly
            355                 360                 365
Val Gly Val Pro Gly Val Gly Val Pro Gly Ala Gly Val Pro Gly Ala
        370                 375                 380
Gly Val Pro Gly Gly Val Pro Gly Gly Val Pro Gly Gly Gly
385                 390                 395                 400
Val Pro Gly Val Gly Val Pro Gly Val Gly Val Pro Gly Val Gly Val
            405                 410                 415
Pro Gly Val Gly Val Pro Gly Val Gly Val Pro Gly Ala Gly Val Pro
            420                 425                 430
Gly Ala Gly Val Pro Gly Gly Gly Val Pro Gly Gly Gly Val Pro Gly
        435                 440                 445
Gly Gly
    450

<210> SEQ ID NO 7
<211> LENGTH: 100
<212> TYPE: PRT
<213> ORGANISM: ELP[V-20]

<400> SEQUENCE: 7

Val Pro Gly Val Gly Val Pro Gly Val Gly Val Pro Gly Val Gly Val
1               5                   10                  15
Pro Gly Val Gly Val Pro Gly Val Gly Val Pro Gly Val Gly Val Pro
            20                  25                  30
Gly Val Gly Val Pro Gly Val Gly Val Pro Gly Val Gly Val Pro Gly
        35                  40                  45
Val Gly Val Pro Gly Val Gly Val Pro Gly Val Gly Val Pro Gly Val
    50                  55                  60
Gly Val Pro Gly Val Gly Val Pro Gly Val Gly Val Pro Gly Val Gly
65                  70                  75                  80
Val Pro Gly Val Gly Val Pro Gly Val Gly Val Pro Gly Val Gly Val
                85                  90                  95
Pro Gly Val Gly
            100
```